United States Patent
Acton, III et al.

(10) Patent No.: US 9,353,101 B2
(45) Date of Patent: May 31, 2016

(54) CYCLIC AMINE SUBSTITUTED HETEROCYCLIC CETP INHIBITORS

(71) Applicant: Merck Sharp & Dohme Corp., Rahway, NJ (US)

(72) Inventors: John J. Acton, III, Cranford, NJ (US); Feng Ye, Scotch Plains, NJ (US); Petr Vachal, Summit, NJ (US); Deyou Sha, Yardley, PA (US); James F. Dropinski, Colts Neck, NJ (US); Lin Chu, Scotch Plains, NJ (US); Debra Ondeyka, Fanwood, NJ (US); Alexander J. Kim, Morganville, NJ (US); Vincent J. Colandrea, North Brunswick, NJ (US); Yi Zang, Princeton Junction, NJ (US); Fengqi Zhang, Edison, NJ (US); Guizhen Dong, Cranford, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/398,165

(22) PCT Filed: Apr. 26, 2013

(86) PCT No.: PCT/US2013/038498
§ 371 (c)(1),
(2) Date: Oct. 31, 2014

(87) PCT Pub. No.: WO2013/165854
PCT Pub. Date: Nov. 7, 2013

(65) Prior Publication Data
US 2015/0111866 A1  Apr. 23, 2015

Related U.S. Application Data

(60) Provisional application No. 61/641,489, filed on May 2, 2012.

(51) Int. Cl.
| | | |
|---|---|---|
| C07D 417/14 | (2006.01) | |
| C07D 413/14 | (2006.01) | |
| A61K 31/506 | (2006.01) | |
| A61K 31/5377 | (2006.01) | |
| A61K 31/444 | (2006.01) | |
| A61K 45/06 | (2006.01) | |

(52) U.S. Cl.
CPC ............ *C07D 417/14* (2013.01); *A61K 31/444* (2013.01); *A61K 31/506* (2013.01); *A61K 31/5377* (2013.01); *A61K 45/06* (2013.01); *C07D 413/14* (2013.01)

(58) Field of Classification Search
CPC .. C07D 417/14; C07D 413/14; A61K 31/506; A61K 31/5377; A61K 31/444; A61K 45/06
See application file for complete search history.

(56) References Cited

U.S. PATENT DOCUMENTS

| | | |
|---|---|---|
| 5,574,030 A | 11/1996 | Masaki et al. |
| 7,915,271 B2 | 3/2011 | Ali et al. |
| 8,440,702 B2 | 5/2013 | Ali et al. |
| 2006/0040999 A1 | 2/2006 | Ali et al. |
| 2009/0042892 A1 | 2/2009 | Ali et al. |

FOREIGN PATENT DOCUMENTS

| | | | |
|---|---|---|---|
| WO | 2007/081569 | * | 7/2007 |
| WO | 2011/028395 | * | 3/2011 |
| WO | 2011028395 A1 | | 3/2011 |
| WO | WO2012058187 A1 | | 5/2012 |

OTHER PUBLICATIONS

Office Action for U.S. Appl. No. 13/881,896, issued Mar. 12, 2015, 13 pages.
Notice of Allowance, U.S. Appl. No. 13/881,896, mailed Aug. 4, 2015.
International Search Report of PCT/US2013/038498 mailed Sep. 18, 2013, 8 pages.

* cited by examiner

*Primary Examiner* — James O Wilson
*Assistant Examiner* — Ebenezer O Sackey
(74) *Attorney, Agent, or Firm* — Eric A. Meade; Anna L. Cocuzzo

(57) ABSTRACT

Compounds having the structure of Formula I, including pharmaceutically acceptable salts of the compounds, are CETP inhibitors and may be useful for raising HDL-cholesterol and reducing LDL-cholesterol in human patients and for treating or preventing atherosclerosis.

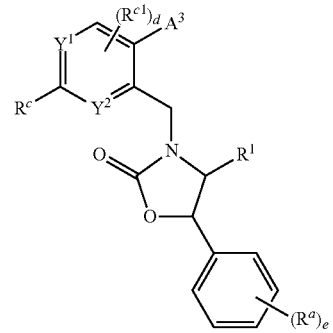

17 Claims, No Drawings

CYCLIC AMINE SUBSTITUTED HETEROCYCLIC CETP INHIBITORS

CROSS REFERENCE TO RELATED APPLICATIONS

This application is a U.S. National Phase application under 35 U.S.C. §371 of PCT Application No. PCT/US13/38498, filed Apr. 26, 2013, which claims priority from U.S. Provisional Application Ser. No. 61/641,489, filed May 2, 2012, which is incorporated by reference in its entirety into this application.

FIELD OF THE INVENTION

This invention relates to chemical compounds that inhibit cholesterol ester transfer protein (CETP) and may have utility in raising HDL-C, lowering LDL-C, and in the treatment or prevention of atherosclerosis.

BACKGROUND OF THE INVENTION

Atherosclerosis and its clinical consequences, including coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA reductase inhibitors, especially the statins, in reducing coronary events is based on the reduction of circulating low density lipoprotein cholesterol (LDL-C), levels of which correlate directly with an increased risk for atherosclerosis. More recently, epidemiologic studies have demonstrated an inverse relationship between high density lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoprotein and transports cholesterol ester from HDL to the apoB lipoprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S. and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering LDL-C.

Despite the significant therapeutic advance that statins such as simvastatin and atorvastatin represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin provides an effective therapy for raising HDL-C but suffers from patient compliance issues, due in part to side effects such as flushing. Drugs that inhibit CETP (CETP inhibitors) have been under development with the expectation that they will effectively raise HDL cholesterol levels and also reduce the incidence of atherosclerosis in patients. Torcetrapib was the first drug that was tested in a long-term outcomes clinical trial. The clinical trial of torcetrapib was terminated early due to a higher incidence of mortality in patients to whom torcetrapib and atorvastatin were administered concomitantly compared with patients who were treated with atorvastatin alone. The cause of the increased mortality is not completely understood, but it is not believed to be associated with the CETP inhibiting effects of the drug.

Two other drug candidates, dalcetrapib and anacetrapib, are currently being tested in Phase III clinical trials, including large scale outcomes trials. Data from the recently completed DEFINE Phase III trial of anacetrapib are promising. Patients who were treated with anacetrapib along with baseline statin therapy showed an increase of HDL-C of 138% and a decrease of LDL-C of 40% compared with patients who were treated with just a statin. See: *N. Engl. J. Med.* 2010: 363: 2406-15. The data in the DEFINE trial were sufficient to indicate that an increase in mortality for patients treated with anacetrapib is unlikely. Additional drug candidates are still being sought that may have properties that are advantageous compared with the CETP inhibitors that have so far been studied or are currently being studied. Such properties may include, for example, higher potency, reduced off-target activity, better pharmacodynamics, higher bioavailability, or a reduced food effect compared with many of the highly lipophilic compounds that have so far been studied. "Food effect" refers to the variability in exposure to the active drug that occurs depending on when the patient had last eaten, whether or not the drug is administered with food, and the fat content of the food.

SUMMARY OF THE INVENTION

The compound of Formula I, or a pharmaceutically acceptable salt thereof, is a potent CETP inhibitor:

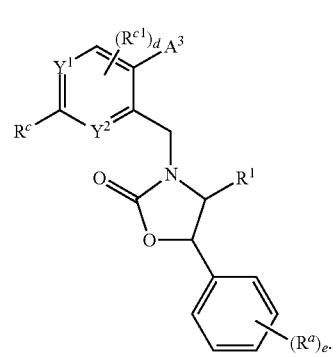

In Formula I, $A^3$ is represented by Formula II or Formula III, or is a 5-6 membered heteroaromatic group other than oxazole or thiazole that has 1-3 heteroatoms which are each independently O, S, or N, wherein the 5-6-membered heteroaromatic group is optionally substituted with 1-3 substituents which are independently halogen, $C_{1-3}$ alkyl or —$OC_{1-3}$ alkyl, wherein $C_{1-3}$ alkyl and —$OC_{1-3}$ alkyl are optionally substituted with 1-6 halogens;

$Y^1$ and $Y^2$ are each N or —CH—, at least one of $Y^1$ and $Y^2$ is N, and —CH— is optionally substituted with $R^{c1}$ in place of H;

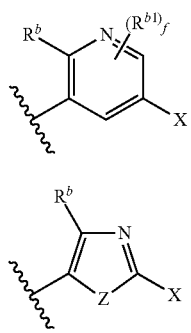

Z is O or S;

$R^1$ is H, $CF_3$, or $C_{1-3}$ alkyl;

Each $R^a$ is independently $C_{1-3}$ alkyl optionally substituted with 1-6 halogens; —$OC_{1-3}$ alkyl optionally substituted with 1-6 halogens; halogen; —CN; or $C_{3-4}$ cycloalkyl optionally substituted with 1-3 halogens;

$R^c$ is (a) a 4-7 membered monocyclic heterocycle comprising one N which is bonded to the heteroaromatic ring to which $R^c$ is connected, wherein the monocyclic heterocycle optionally comprises 1-3 double bonds, one carbonyl, and 1-3 additional heteroatom groups which are each independently N, O, S, S(O), or $S(O)_2$; or (b) a 5-8 membered bicyclic heterocycle comprising one N which is bonded to the heteroaromatic ring to which $R^c$ is connected, wherein the bicyclic heterocycle optionally comprises 1-3 double bonds, one carbonyl, and 1-3 additional heteroatom groups which are each independently N, O, S, S(O), or $S(O)_2$, wherein $R^c$ as defined in (a) or (b) is optionally substituted with 1-3 substituent groups which are independently halogen, —OH, —CN, $C_{1-3}$ alkyl, or —$OC_{1-3}$ alkyl, wherein $C_{1-3}$ alkyl and —$OC_{1-3}$ alkyl are optionally substituted with 1-6 halogens;

Each $R^{c1}$ is independently $C_{1-3}$ alkyl, —$OC_{1-3}$ alkyl, or halogen, wherein alkyl in either case is optionally substituted with 1-6 halogens;

$R^b$ is H, $C_{1-4}$ alkyl, —$OC_{1-4}$ alkyl, —$OC_{3-6}$ cycloalkyl, halogen, —CN, —$NO_2$, or —OH, wherein $C_{1-4}$ alkyl and —$OC_{1-4}$ alkyl are optionally substituted with 1-6 halogens, and —$OC_{3-6}$ cycloalkyl is optionally substituted with 1-3 halogens;

Each $R^{b1}$ is independently $C_{1-3}$ alkyl, —$OC_{1-3}$ alkyl, or halogen, wherein $C_{1-3}$ alkyl and —$OC_{1-3}$ alkyl are optionally substituted with 1-6 halogens;

X is:
(a) (i) halogen, (ii) —$C_{1-4}$ alkyl, (iii) —$C_{3-6}$cycloalkyl-Y, or $C_{1-3}$ alkyl-Y, wherein Y is —CN, —OH, or —$OCH_3$, (iv) —$C_{3-6}$ cycloalkyl, or (v) -phenyl which is optionally substituted with 1-3 groups which are independently halogen, —CN, —OH, —$C_{1-4}$ alkyl, —$OC_{1-4}$ alkyl, or —$C(=O)C_{1-2}$ alkyl, and optionally one group —$C_{1-4}$alkyl-OH, wherein alkyl in all uses is optionally substituted with 1-6 halogens, and cycloalkyl in all uses is optionally substituted with 1-3 groups which are independently halogen or —$C_{1-3}$ alkyl which are optionally substituted with 1-6 halogens;

(b) $D^1$, wherein $D^1$ is —$CO_2H$, —$CO_2C_{1-4}$ alkyl, or —$C(=O)NR^2R^3$;

(c) —$C_{1-3}$ alkyl-$D^1$, wherein —$C_{1-3}$alkyl is optionally substituted with 1-6 halogens;

(d) —$C_{3-6}$cycloalkyl-$D^1$, wherein cycloalkyl is optionally substituted with 1-2 groups which are independently —$C_{1-3}$ alkyl or halogen, wherein —$C_{1-3}$ alkyl is optionally substituted with 1-6 halogens;

(e) —$C_{3-6}$cycloalkyl-$CH_2$-$D^1$, wherein cycloalkyl is optionally substituted with 1-2 groups which are independently —$C_{1-3}$ alkyl or halogen, wherein —$C_{1-3}$ alkyl is optionally substituted with 1-6 halogens;

(f) -phenyl-$D^2$, wherein $D^2$ is $D^1$, HET, or —$C(=O)NH$—HET, wherein phenyl is optionally substituted with 1-3 substituents which are independently halogen, —CN, —OH, —$C_{1-3}$alkyl optionally substituted with 1-6 halogens, or —$OC_{1-3}$alkyl optionally substituted with 1-6 halogens;

(g) -HET-$D^1$, wherein HET is a 5-6-membered heteroaromatic ring having 1-4 heteroatom groups which are each independently N, O, S, S(O), $S(O)_2$, or C(=O), wherein HET is optionally substituted with 1-3 groups which are independently halogen, —$CH_3$, —$CF_3$, —$OCH_3$, or —$OCF_3$; or (h) —$(C_{1-2}$alkyl$)_{0-2}$-HET, wherein HET is optionally substituted with 1-3 groups which are independently halogen, —OH, —$NH_2$, —$C_{1-4}$alkyl optionally substituted with 1-6 halogens, or —$OC_{1-3}$alkyl optionally substituted with 1-6 halogens, and optionally one group which is —$C_{1-3}$alkyl-CN or —$CH_2C(=O) NR^2R^3$;

$R^2$ and $R^3$ are each independently H or —$C_{1-3}$alkyl, or $R^2$ and $R^3$ are optionally joined to form a bridging group having 3-5 carbons, thereby yielding a 4-6 membered cyclic amide group;

d is an integer from 0-2;
e is an integer from 0-3; and
f is an integer from 0-2.

In the compound of Formula I, and in subgroups and other embodiments of the invention, alkyl groups and substituents based on alkyl groups, such as alkoxy, may be linear or branched unless otherwise indicated.

In general, references to the compound(s) of formula I or to the compound(s) of the invention herein are meant to also include subsets of compounds of formula I as may be defined herein, and specifically also are meant to include the specific numbered examples provided herein.

DETAILED DESCRIPTION OF THE INVENTION

In further embodiments of the invention, the substituent groups defined above may have alternative values independent of one another, as written below. Such embodiments include pharmaceutically acceptable salts when such salts are possible.

In many embodiments of the compound of Formula I,
$A^3$ is represented by Formula II or Formula III as defined above or is a 5-membered heteroaromatic group other than oxazole or thiazole that has 1-3 heteroatoms which are each independently O, S, or N, wherein the 5-membered heteroaromatic group is optionally substituted with 1-3 substituents which are independently halogen, —$CH_3$, —$CF_3$, —$OCH_3$, or —$OCF_3$.

Alternatively, $A^3$ is represented by Formula II or Formula III as defined above or is isoxazole which is optionally substituted with 1-2 substituents which are independently halogen, —$CH_3$, —$CF_3$, —$OCH_3$, or —$OCF_3$.

Alternatively, $A^3$ is represented by Formula II or Formula III as defined above or is isoxazole which is optionally substituted with 1-2 substituents which are —$CH_3$.

In embodiments of the compound of Formula I, $R^1$ is H or $C_{1-3}$alkyl. Alternatively, $R^1$ is $CH_3$.

In embodiments of the compound of Formula I, each $R^a$ is independently $CF_3$, —$OCF_3$, $CH_3$, —$OCH_3$, halogen, —CN, or cyclopropyl which is optionally substituted with 1-3 halogens. Alternatively, each $R^a$ is independently F, —$CF_3$, or —$OCF_3$.

In embodiments of the compound of Formula I, $R^c$ is (a) a 4-6 membered monocyclic amine comprising one N which is bonded to the heteroaromatic ring to which $R^c$ is connected, wherein the monocyclic amine optionally comprises one O in the ring and optionally 1-2 double bonds, wherein $R^c$ is optionally substituted with 1-2 groups which are each independently halogen, —OH, $CH_3$, —$OCH_3$, $CF_3$, or —$OCF_3$.

Alternatively, $R^c$ is (1) a 4-5 membered saturated monocyclic amine comprising one N which is bonded to the heteroaromatic ring to which $R^c$ is connected and which is optionally substituted with 1-2 groups which are independently F, $CH_3$, or —OH, (2) morpholino in which the N of the morpholino group is connected to the heteroaromatic ring to which $R^c$ is connected, or (3) imidazolyl in which the N of the imidazolyl group is connected to the heteroaromatic ring to which $R^c$ is connected.

In embodiments of the compound of Formula I, each $R^{c1}$ is independently $CH_3$, $CF_3$, —$OCH_3$, —$OCF_3$ or halogen. Alternatively, Each $R^{c1}$ is independently —$CH_3$ or Br.

In embodiments of the compound of Formula I, $R^b$ is H, $C_{1-4}$ alkyl, —$OC_{1-4}$ alkyl, —$OC_{3-6}$ cycloalkyl, or halogen, wherein $C_{1-4}$ alkyl and —$OC_{1-4}$ alkyl are optionally substituted with 1-6 halogens, and —$OC_{3-6}$ cycloalkyl is optionally substituted with 1-3 halogens. Alternatively, $R^b$ is $C_{1-4}$ alkyl or —$OC_{1-4}$ alkyl, wherein $C_{1-4}$ alkyl and —$OC_{1-4}$ alkyl are optionally substituted with 1-6 halogens. Alternatively, $R^b$ is —$C_{1-4}$ alkyl or —$OC_{1-2}$ alkyl, wherein —$C_{1-4}$ alkyl and —$OC_{1-2}$ alkyl are optionally substituted with 1-6 halogens.

In embodiments of the compound of Formula I, each $R_{b1}$ is independently halogen, $CF_3$, or $CH_3$. Alternatively, $R^{b1}$ is F.

In embodiments of the compound of Formula I, X may be:
(a) (i) halogen, or alternatively Cl.

In embodiments of the compound of Formula I, X may be:
(ii) —$C_{1-4}$ alkyl which is optionally substituted with 1-6 halogens.

In embodiments of the compound of Formula I, X may be:
(iii) $C_{1-3}$alkyl-Y, wherein $C_{1-3}$alkyl is optionally substituted with 1-6 halogens and Y is —CN, —OH, or —$OCH_3$; or alternatively, X may be $C_{1-3}$alkyl-Y, wherein $C_{1-3}$alkyl is optionally substituted with 1-6 halogens and Y is —OH.

In embodiments of the compound of Formula I, X may be:
(iv) —$C_{3-6}$cycloalkyl optionally substituted with 1-3 groups independently selected from halogen and —$CH_3$, or alternatively, —$C_{3-6}$cycloalkyl which is unsubstituted.

In embodiments of the compound of Formula I, X may be:
(b) $D^1$, where $D^1$ is —$CO_2H$, —$CO_2C_{1-4}$alkyl, or —C(=O)$NR^2R^3$.

In embodiments of the compound of Formula I, X may be:
(c) —$C_{1-3}$alkyl-$D^1$, wherein alkyl is optionally substituted with 1-6 halogens.

In embodiments of the compound of Formula I, X may be:
(d) —$C_{3-6}$cycloalkyl-$D^1$, wherein cycloalkyl is optionally substituted with 1-2 groups which are independently —$CH_3$, $CF_3$, or halogen.

In embodiments of the compound of Formula I, X may be:
(e) —$C_{3-6}$cycloalkyl-$CH_2$-$D^1$, wherein cycloalkyl is optionally substituted with 1-2 groups which are independently —$CH_3$, $CF_3$, or halogen.

In embodiments of the compound of Formula I, X may be:
(f) -phenyl-$D^2$, wherein $D^2$ is $D^1$, 1,3,4-oxadiazol-2(3H)-one, tetrazole, or —C(=O)NH-tetrazole, wherein phenyl is optionally substituted with 1-3 substituents which are independently halogen, —$CH_3$, —$CF_3$, —$OCH_3$, or —$OCF_3$; or alternatively, phenyl in -phenyl-$D_2$ is optionally substituted with 1-3 substituents which are independently halogen, —$CH_3$, or —$CF_3$;

In alternative embodiments of the compound of Formula I, X may be:
(g) HET, wherein HET is a 5-membered heteroaromatic ring having 1-3 heteroatoms groups which are each independently N, O, or S and is optionally substituted with 1-3 groups which are independently halogen, —$C_{1-3}$ alkyl optionally substituted with 1-6 halogens, or —$OC_{1-3}$ alkyl optionally substituted with 1-6 halogens, and is optionally substituted with one group which is —$C_{1-3}$alkyl-CN or —$CH_2C$(=O)$NR^2R^3$.

In embodiments of the compound of Formula I, $R^2$ and $R^3$ are independently H or —$CH_3$.

In embodiments of the compound of Formula I, d is 0 or 1. In other embodiments, d is 0.

In embodiments of the compound of Formula I, e is an integer from 1-3. In other embodiments, e is an integer from 1-2.

In embodiments of the compound of Formula I, f is 0 or 1. In other embodiments, f is 0.

DEFINITIONS AND ABBREVIATIONS

"Ac" is acetyl, which is $CH_3C$(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, n-butyl, sec-butyl, tert-butyl, pentyl, hexyl, heptyl, octyl, nonyl, and the like.

"Alkylene" groups are alkyl groups that are difunctional rather than monofunctional. For example, methyl is an alkyl group and methylene (—$CH_2$—) is the corresponding alkylene group. Alkyl groups that are shown as difunctional are alkylene groups, even if they are referred to as alkyl groups.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated. The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" when used to describe a substituent or group in a structure means a monocyclic or bicyclic compound in which the rings are aromatic and which contain only carbon ring atoms. The term "aryl" can also refer to an aryl group that is fused to a cycloalkyl or heterocycle. Preferred "aryls" are phenyl and naphthyl. Phenyl is generally the most preferred aryl group.

"Heterocycle" or "heterocyclic" means a fully or partially saturated or aromatic cyclic compound containing 1 or more heteroatom groups which may be one or more of N, S, O, S(O), S(O)$_2$, or (N)R, and may have one or more double bonds, where R is H or a substituent group. In general, when heterocycles are defined herein, the definition will include the number of ring members, the number of double bonds (if any), and the specific heteroatoms. The heterocycles in some cases will be aromatic, depending on the number of double bonds (e.g. 6-membered ring with 3 double bonds). S(O), S(O)$_2$, and N(R) are referred to as heteroatom groups, and each heteroatom group is counted as one ring member, as is also the case for N, S, and O.

"Benzoheterocycle" represents a phenyl ring fused to a heterocyclic ring. Examples include indole, benzofuran, 2,3-dihydrobenzofuran and quinoline.

"Boc" is tert-butoxycarbonyl.
"n-BuLi" is n-butyl lithium.
"Cbz" is carboxybenzyl.
"Celite®" is a trade name for diatomaceous earth.
"DBU" is 1,8-diazabicyclo[5.4.0]undec-7-ene.
"DIEM" is diisopropylethylamine.
"DCM" is dichloromethane.
"DMA" is N,N-dimethylacetamide
"DMF" is N,N-dimethylformamide.
"DMAP" is 4-dimethylaminopyridine
"DMSO" is dimethyl sulfoxide.
"EDC" is 1-ethyl-3-(3-dimethylaminopropyl)carbodiimide hydrochloride.
"EDTA" is ethylenediaminetetraacetic acid.
"ETOAc" is ethyl acetate.
"Halogen" includes fluorine, chlorine, bromine and iodine.
"HOBt" is hydroxybenzotriazole.
"HPLC" is high pressure liquid chromatography.
"IPA" is isopropyl alcohol.
"LiHMDS" is lithium hexamethyldisilazide.
"Me" represents methyl.
"MeCN" is acetonitrile.
"MeOH" is methanol.
"MsCl" is methanesulfonyl chloride.
"mCPBA" is meta-chloroperoxybenzoic acid.
"NaHMDS" is sodium hexamethyldisilazide.
"NCS" is N-chlorosuccinimide.
"NMP" is N-methyl-2-pyrrolidone.
"PEG" is poly(ethylene glycol).
"RBF" is a round bottom flask.
"RT" is an abbreviation for room temperature.
"SFC" is supercritical fluid chromatography.
"SM" is starting material
"TEA" is triethylamine.
"TFA" is trifluoroacetic acid.
"THF" is tetrahydrofuran.
"TLC" is thin layer chromatography.

The term "composition," as in pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers-Diastereomers-Geometric Isomers-Tautomers

The compounds disclosed herein generally have at least two asymmetric centers, and can thus occur as pure stereoisomers and as mixtures of stereoisomers, including racemates, racemic mixtures, single enantiomers, mixtures of enantiomers, diastereomeric mixtures and individual diastereomers. Different stereoisomers having the same 2-dimensional chemical structure may have different levels of activity with respect to CETP inhibition, so that some stereoisomers may have higher activity than others. The compounds that are potent inhibitors of CETP may have utility in patients for raising HDL-C, lowering LDL-C, treating dyslipidemia, or for preventing, treating or delaying the onset of conditions that are related to atherosclerosis. Both potent stereoisomers and stereoisomers that have little or no activity may have utility as research tools for better understanding CETP inhibition. All stereoisomers of the claimed compounds thus have utility. The compounds of Formula I may also occur as atropisomers (rotamers) due to hindered rotation, which may be observable by NMR spectroscopy, and in some cases are stable enough with respect to conversion by bond rotation to other atropisomers that they can be isolated and assayed.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, triethanolamine, trimethylamine, tripropylamine, tromethamine, and the like.

When the compound of the present invention is basic, salts may be prepared from pharmaceutically acceptable non-toxic acids, including inorganic and organic acids. Such acids include acetic, adipic, ascorbic, benzenesulfonic, benzoic, camphorsulfonic, citric, diethylacetic, ethanesulfonic, formic, fumaric, gluconic, glutamic, hydrobromic, hydrochloric, isethionic, isonicotinic, lactic, maleic, malic, malonic, mandelic, methanesulfonic, mucic, naphthalenedisulfonic, nitric, oxalic, pamoic, pantothenic, phenylpropionic, phosphoric, pimelic, pivalic, propionic, salicylic, succinic, sulfuric, sulfaminic, tartaric, p-toluenesulfonic acid, trifluoroacetic and the like. Particularly preferred are citric, hydrobromic, hydrochloric, maleic, phosphoric, sulfuric, and tartaric acids. Other acid salts may include bicarbonate, bisulfate, bitartrate, borate, hydrobromide, camsylate, carbonate, clavulanate, edisylate, estolate, esylate, gluceptate, hydroxynaphthoate, iodide, lactobionate, laurate, mesylate, napsylate, oleate, palmitate, polygalacturonate, stearate, subacetate, tannate, valerate, ascorbate, butyrate, camphorate, and camphorsulfonate.

It will be understood that, as used herein, references to the compounds of the invention are also meant to be references to the compounds of Formula I and to the examples, and are meant to also include the pharmaceutically acceptable salts, where such salts are possible.

Prodrugs

Prodrugs, which are compounds that are converted to the compound of Formula I as they are being administered to a patient or after they have been administered to a patient, are also compounds of this invention in the sense that they provide the claimed pharmaceutically active drug moiety to the patient.

Utilities

The compounds disclosed herein, including pharmaceutically acceptable salts thereof, are inhibitors of CETP. The compounds may therefore be useful in treating mammalian patients, preferably human patients, having diseases and conditions that are treated by inhibition of CETP.

One aspect of the present invention provides a method for treating a disease or condition that may be treated or prevented by inhibition of CETP by administering a therapeutically effective amount of the compound of Formula I to a patient in need of treatment. A further aspect provides a method for reducing the risk of developing a disease or condition that may be treated or prevented by inhibition of CETP by administering a therapeutically effective amount of the compound of Formula I to a patient in need of treatment. The patient is a human or mammal, but is most often a human. A "therapeutically effective amount" is the amount of compound that is effective in obtaining a desired clinical outcome in the treatment of a specific disease.

Diseases or conditions that may be treated with the compounds of this invention, or which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome.

The compounds disclosed herein may be particularly effective in raising HDL-C and/or increasing the ratio of HDL-C to LDL-C. The compounds may also be effective in reducing LDL-C, and may be effective in treating dyslipidemia. These changes in HDL-C and LDL-C may be beneficial in treating atherosclerosis, reducing or reversing the development of atherosclerosis, reducing the risk of developing atherosclerosis, or preventing atherosclerosis. The compounds disclosed herein thus may be beneficial in treating atherosclerosis, reducing or reversing the development of atherosclerosis, reducing the risk of developing atherosclerosis, and preventing atherosclerosis.

Potential indications for atherosclerosis and dyslipidemia using the compounds described herein are written below, where the drug product is titled "CETP inhibitor:"

Atherosclerosis.

In patients at high risk of cardiovascular events because of existing coronary, cerebrovascular, or peripheral vascular disease, CETP inhibitor co-administered with an HMG-CoA reductase inhibitor is indicated to reduce the risk of coronary mortality, myocardial infarction, coronary revascularization procedures, ischemic stroke, and cardiovascular death.

Dyslipidemia.

CETP inhibitor co-administered with a statin is indicated to reduce elevated LDL-C, apolipoprotein B (ApoB), lipoprotein a (Lp(a)), non-HDL-C, and total cholesterol; and increase HDL-C and apolipoprotein A-1 (Apo A-1) in patients with mixed or primary dyslipidemia.

As used herein, "treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. The term "treating" as used herein refers to administering a compound after the onset of clinical symptoms As used herein "preventing" or "prevention" refers to a reduction in risk of acquiring or developing a disease or disorder (i.e., causing at least one of the clinical symptoms of the disease not to develop in a subject that may be exposed to a disease-causing agent, or predisposed to the disease in advance of disease onset). The term "preventing" as used herein refers to administering a compound before the onset of clinical symptoms.

Administration and Dose Ranges

Any suitable route of administration may be employed for providing a mammal, especially a human, with an effective dose of the compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably, the compound of Formula I is administered orally.

When treating the diseases for which the compound of Formula I is indicated, generally satisfactory results are expected when the compound of the present invention is administered at a daily dosage of from about 0.1 milligram to about 1000 milligram in one dose daily or divided into more than one dose per day.

Oral administration will usually be carried out using tablets. Examples of doses in tablets include 0.1 mg, 0.5 mg, 1 mg, 2 mg, 5 mg, 10 mg, 25 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 300 mg, 350 mg, 400 mg, 450 mg, 500 mg, and 1000 mg. Other oral forms can also have the same dosages (e.g. capsules). A preferred dose is in the range of 50-200 mg.

Pharmaceutical Compositions

Another aspect of the present invention provides pharmaceutical compositions which comprise the compound of Formula I and a pharmaceutically acceptable carrier. The pharmaceutical compositions of the present invention comprise the compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. A pharmaceutical composition may also consist essentially of the compound of Formula I, or a pharmaceutically acceptable salt of the compound, and a pharmaceutically acceptable carrier, without other therapeutic ingredients.

Pharmaceutical compositions may be formulated to be suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compound of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compound can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye, and a flavoring such as cherry or orange flavor.

The Compound of formula I may also be administered parenterally. Solutions or suspensions of the compound can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

The compound of Formula I, including pharmaceutically acceptable salts, may be used in combination with other drugs that may also be useful in the treatment or amelioration of the diseases or conditions for which the compound of Formula I is useful. Such other drugs may be administered, by a route and in an amount commonly used therefor, contemporaneously or sequentially with the compound of Formula I. When the compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered concomitantly, on the same or different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®), rivastatin, pitavastatin, and other statins), (ii) bile acid sequestrants (cholestyramine, colestipol, dialkylaminoalkyl derivatives of a cross-linked dextran, Colestid®, LoCholest®, (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate, bezafibrate, ciprofibrate, and etofibrate, (v) cholesterol absorption inhibitors, such as stanol esters, beta-sitosterol, sterol glycosides such as tiqueside; and azetidinones, such as ezetimibe, (vi) acyl CoA:cholesterol acyltransferase (ACAT) inhibitors, such as avasimibe and melinamide, and including selective ACAT-1 and ACAT-2 inhibitors and dual inhibitors, (vii) phenolic anti-oxidants, such as probucol, (viii) microsomal triglyceride transfer protein (MTP)/ApoB secretion inhibitors, (ix) anti-oxidant vitamins, such as vitamins C and E and beta carotene, (x) thyromimetics, (xi) LDL (low density lipoprotein) receptor inducers, (xii) platelet aggregation inhibitors, for example glycoprotein IIb/IIIa fibrinogen receptor antagonists and aspirin, (xiii) vitamin B12 (also known as cyanocobalamin), (xiv) folic acid or a pharmaceutically acceptable salt or ester thereof, such as the sodium salt and the methylglucamine salt, (xv) FXR and LXR ligands, including both inhibitors and agonists, (xvi) agents that enhance ABCA1 gene expression, and (xvii) ileal bile acid transporters.

Preferred classes of therapeutic compounds that may be used with the compounds of this invention for uses described above, such as improving a patient's lipid profile (i.e. raising HDL-C and lowering LDL-C) and for treating, preventing, or reducing the risk of developing atherosclerosis, include one or both of statins and cholesterol absorption inhibitors. Particularly preferred are combinations of the compounds of this invention with a statin, with ezetimibe, or with both a statin and ezetimibe. Statins that may be used in these combinations include simvastatin, lovastatin, rosuvastatin, pravastatin, fluvastatin, atorvastatin, rivastatin, and pitavastatin. Preferred statins for use in combination therapy include simvastatin, atorvastatin, and rosuvastatin. Preferred combinations include combinations of a CETP inhibitor as disclosed herein and one or more cholesterol reducing agents, such as (a) atorvastatin; (b) simvastatin; (c) rosuvastatin; (d) ezetimibe; (e) atorvastatin and ezetimibe; (f) simvastatin and ezetimibe; or (g) rosuvastatin and ezetimibe.

Finally the compound of this invention can be used with compounds that are useful for treating other diseases, such as diabetes, hypertension and obesity, as well as other anti-atherosclerotic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these diseases, allowing for the possibility of administering reduced doses of active ingredients, such as doses that otherwise might be sub-therapeutic.

Examples of other active ingredients that may be administered in combination with a compound of this invention include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818);

(b) biguanides such as metformin and phenformin;

(c) protein tyrosine phosphatase-1B (PTP-1B) inhibitors;

(d) dipeptidyl peptidase IV (DP-IV) inhibitors, including sitagliptin, vildagliptin, saxagliptin, alogliptin, linagliptin, dutogliptin, and gemigliptin;

(e) insulin or insulin mimetics, such as for example insulin lispro, insulin glargine, insulin zinc suspension, and inhaled insulin formulations;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 analogs, such as exendins, such as for example exenatide (Byetta); and non-peptidyl GLP-1 receptor agonists;

(l) GIP-1; and (m) Non-sulfonylurea insulin secretagogues, such as the meglitinides (e.g. nateglinide and rapeglinide).

Preferred combinations with antidiabetic compounds include combinations of the compounds disclosed herein with DP-IV inhibitors (sitagliptin, alogliptin, vildagliptin, saxagliptin, linagliptin, dutogliptin, or gemigliptin), combinations with biguanides, and combinations with both a DP-IV inhibitor and a biguanide. The preferred DP-IV inhibitor is sitagliptin, and the preferred biguanide is metformin.

These other active ingredients that may be used in combination with the current invention also include antiobesity compounds, including 5-HT (serotonin) inhibitors, neuropeptide Y5 (NPY5) inhibitors, melanocortin 4 receptor (Mc4r) agonists, cannabinoid receptor 1 (CB-1) antagonists/inverse agonists, and β₃ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compounds of this invention. Examples of antihypertensive compounds that may be used with the compounds of this invention include (1) angiotensin II antagonists, such as candesartan, eprosartan, irbesartan, losartan, olmesartan, telmisartan, and valsartan; (2) angiotensin converting enzyme inhibitors (ACE inhibitors), such as alacepril, benazepril, captopril, ceronapril, cilazapril, delapril, enalapril, enalaprilat, fosinopril, imidapril, lisinopril, moexepril, moveltipril, perindopril, quinapril, ramipril, spirapril, temocapril, or trandolapril; (3) calcium channel blockers such as nifedipine and diltiazam; and (4) endothelin antagonists.

Preferred antihypertensives that may be used in combination with the CETP inhibitors disclosed herein include one or more of an angiotensin II antagonist (losartan), an ACE inhibitor (enalapril or captopril), and hydrochlorothiazide.

Anti-obesity compounds may be administered in combination with the compounds of this invention, including: (1) growth hormone secretagogues and growth hormone secretagogue receptor agonists/antagonists, such as NN703 and hexarelin; (2) protein tyrosine phosphatase-1B (PTP-1B) inhibitors; (3) cannabinoid receptor ligands, such as cannabinoid CB' receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, amrinone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6,beta-Ala11,Phe13,Nle14]Bn(6-14) and [D-Phe6, Phe13]Bn(6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2 (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) aminorex; (81) amphechloral; (82) amphetamine; (83) benzphetamine; and (84) chlorphentermine.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

ASSAYS

Protocol: Scintillation Proximity Assay (SPA) for CETP Activity

First, low density lipoprotein (LDL) (Meridian) was biotinylated by incubating LDL with biotin for 1 hour on ice, after which it was dialyzed to remove free biotin. Then compounds at varying concentrations were incubated with 15 nM CETP (reagent production group, In Vitro Pharmacology, MRL Rahway) and 50 ug/ml of the biotinylated LDL in 50 mM HEPES, 150 mM NaCl, pH 7.4, for 1 hour at 37° C. The reaction was started by adding $^3$H-cholesterol ester high density lipoprotein (HDL) (American Radiochemicals Corp) at a concentration of ~0.6 nM. The reaction proceeded for 2 hours at 37° C., after which time it was quenched by the addition of 12% acetic acid. PVT streptavadin-coated scintillation proximity beads, which had been brought to room temperature, were then added at a concentration of 4 mg/ml. The assay was then mixed and counted after one half hour in a Microbeta plate reader.

In Vitro Radioactive Assays of CETP-Catalyzed CE and TG Transfer (RTA Assay)

Reagents and sources are: [3H] cholesteryl oleate (GE #TRK.886), [3H] Triolein (Perkin-Elmer NET-431), Butylated hydroxyl toluene (Aldrich, #D4740-4), DOPC (Sigma, # P6354), Sodium Bromide (Fisher scientific #S255-500), PEG 8000 (Fisher, #BP233-1), and human HDL (Intracel Corp #RP-036).

An in vitro assay for determining $IC_{50}$'s to identify compounds that inhibit CETP transfer activity is performed based on a modification of a published method (Morton and Zilversmit, (1981) A plasma inhibitor of triglyceride and cholesteryl ester transfer activities, J. Biol. Chem. 256(23), 11992-11995). The ability of inhibitors to alter CETP activity is performed using two different assays: one using recombinant CETP and one using an endogenous plasma source of CETP. Both assays measure the transfer of [3H] cholesteryl oleate or [3H] triolein from exogenous LDL to HDL.

Radiolabeled donor particles are generated by first combining 100 μl of 200 μM butylated hydroxyl toluene in $CHCl_3$, 216 μL of 21.57 mM DOPC in EtOH, and either 500 μCi [3H]-triolein (Perkin Elmer #NET-431) or 500 μCi [3H]-cholesteryl oleate (GE #TRK886) in a glass tube. Reagents are mixed, dried under nitrogen, and then resuspended in 2 mL of 50 mM Tris, 27 μM EDTA at pH 7.4. After a brief vortex, the solution is sonicated until clear and mixed with 20 mL of fresh human serum. The mixture is incubated overnight at 37° C. The [3H] labeled LDL substrate is separated at 1.063 g/ml density by sequential ultracentrifugal flotation in NaBr according to the method by (Havel, Eder et al. 1955; Chapman, Goldstein et al. 1981). Once isolated the particles are dialyzed 3× in CETP buffer (50 mM Tris, pH 7.4, 100 mM NaCl, 1 mM EDTA). Human HDL is purchased from Intracel and used as the acceptor particles.

Transfer assays are performed in a 96 or 384-well v-bottom polypropylene plate. For the RTA using recombinant CETP (2% RTA), an assay cocktail is prepared with the final concentrations 128 μg/mL HDL, 20 nM rCETP, 2% human serum, and 1×CETP buffer. 1 μL of each test compound diluted in DMSO is added to 47 μL of assay cocktail per well and incubated at 37° C. for 1 hour. To initiate the transfer reaction, 2 μL radiolabeled LDL is added. After an additional 60 min of incubation at 37° C., the transfer action is terminated by precipitation of LDL with an equal volume of 20% W/V PEG 8000. The plates are centrifuged at 2000 rpm for 30 minutes at 4° C. A 40 μL aliquot of the HDL-containing supernatant is transferred to a Packard Optiplate™ with 200 μL of MicroScint™ 20. After mixing, plates are counted by liquid scintillation. Counts present in the supernatant for blanks (wells containing only HDL acceptor, CETP buffer and DMSO) are subtracted from those containing test compounds and used to correct for non-specific transfer.

For the transfer assay using endogenous CETP from serum (95% RTA), the same procedure is used except that human serum is added such that a final concentration of serum of 95% of the total assay volume is achieved, yielding a concentration of approximately 15 nM endogenous CETP in the assay. This is then combined with HDL and CETP buffer and the reaction proceeds as above and is terminated as described.

Comparison of the counts of samples with inhibitors to an uninhibited (DMSO only) positive control yield a percent inhibition. A plot of percent inhibition vs. log of inhibitor concentration, fit to a Sigmoidal 4 parameter equation is used to calculate IC50.

EXAMPLES

The following schemes and examples are provided so that the invention will be more fully appreciated and understood. These examples are illustrative and are not to be construed as limiting the invention in any way. The claims appended hereto define the scope of the invention.

Starting materials are commercially available or are made using known procedures or as shown below. The examples may be synthesized using the general schemes provided below. The data reported for the examples below were obtained using the RTA assay in 95% human serum. The IC50's for the examples using this assay are in the range of about 44-1742 nM. Preferred compounds have an IC50 less than about 500 nM. More preferred compounds have an IC50 less than about 100 nM.

SYNTHETIC SCHEMES

Syntheses of Intermediates

The examples were synthesized according to the general schemes provided below. Synthetic intermediates for making the compounds are made as described below and are illustrated in the following schemes. The various starting materials used in the schemes are commercially available or are readily made by persons skilled in the art.

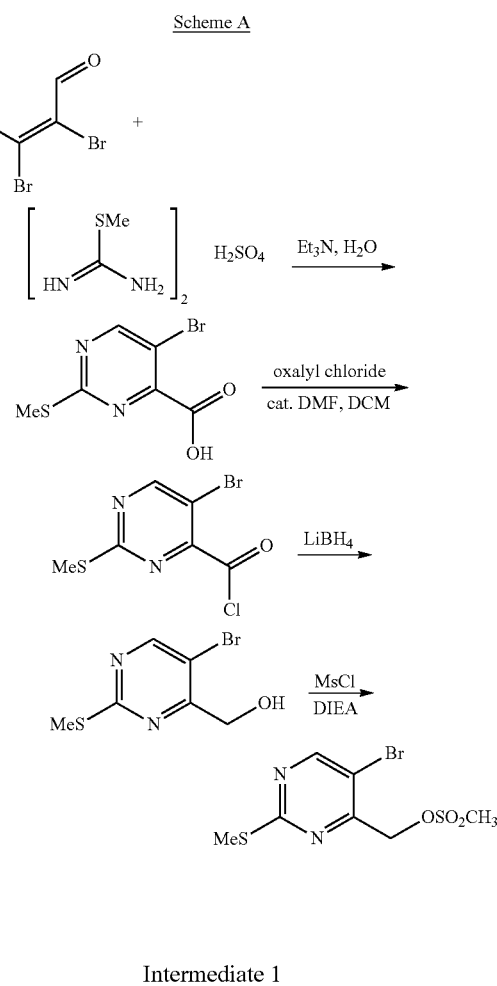

Intermediate 1

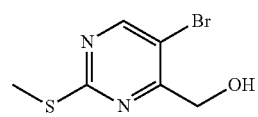

[5-Bromo-2-(methylthio)pyrimidin-4-yl]methanol

The synthesis of INTERMEDIATE 1 has been described previously. See for example, Steps A and B, or the alternate route below step B, for INTERMEDIATE 38 of WO2007081569.

Intermediate 2

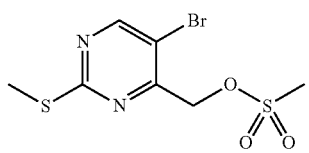

5-Bromo-2-(methylsulfanyl)-4-[(methylsulfonyl)methyl]pyrimidine

Methanesulfonyl chloride (5.85 g, 51.0 mmol) was added to a stirred, cooled 0° C. mixture of [5-bromo-2-(methylthio)pyrimidin-4-yl]methanol (INTERMEDIATE 1, 10 g, 42.5 mmol) in $CH_2Cl_2$ (200 mL), followed by addition of $Et_3N$ (6.46 g, 63.8 mmol). The mixture was stirred at 0° C. for 30 minutes. TLC showed no starting material left. The mixture was quenched with water (30 mL) and the mixture was washed with more water (50 mL). The organic portion was washed with brine (saturated, 50 mL), dried ($Na_2SO_4$), filtered and the solvent was evaporated under reduced pressure. The residue was purified by column chromatography, eluting with EtOAc/hexane (3/7) to give the title compound as a colorless solid. $^1$H NMR ($CDCl_3$, 500 MHz) δ 8.61 (s, 1H), 5.38 (s, 2H), 3.21 (s, 3H), 2.60 (s, 3H).

Intermediate 3

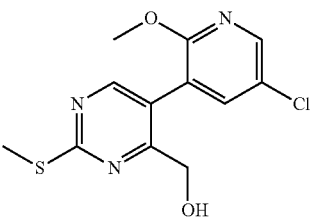 [SMILES: COc1ncc(Cl)cc1-c1cnc(SC)nc1CO]

[5-(5-Chloro-2-methoxypyridin-3-yl)-2-(methylthio)pyrimidin-4-yl]methanol

[5-Bromo-2-(methylthio)pyrimidin-4-yl]methanol (INTERMEDIATE 1, 1.9 g, 8.08 mmol), 5-chloro-2-methoxy-pyridin-3-ylboronic acid (1.51 g, 8.08 mmol) and $K_2CO_3$ (3.35 g, 24.24 mmol) were added to a round bottom flask, which was then evacuated and charged with nitrogen 3 times. THF (30 mL) and water (6 mL) were then added. After evacuating and charging again with nitrogen, 1,1'-bis(di-tert-butylphosphino)ferrocene palladium dichloride (0.527 g, 0.808 mmol) was added and the reaction heated for 30 minutes at 50° C. LCMS showed 80% conversion to product plus 20% unreacted bromide. The reaction was diluted with 15 mL acetonitrile and filtered through a 4 g $C_{18}$ cartridge, eluting with 50 mL acetonitrile until the filtrate was colorless. The filtrate was then concentrated. Silica gel chromatography using a 0-50% isopropyl acetate/hexanes linear gradient followed by an isocratic hold of 50% isopropyl acetate/hexanes gave an 80/20 inseparable mixture of title compound and recovered starting material, which was more thoroughly purified later in the synthetic route. LCMS (M+H)$^+$: 298.3 Title compound. LCMS (M+H)$^+$: 237.1 Starting material (INTERMEDIATE 1).

Scheme B

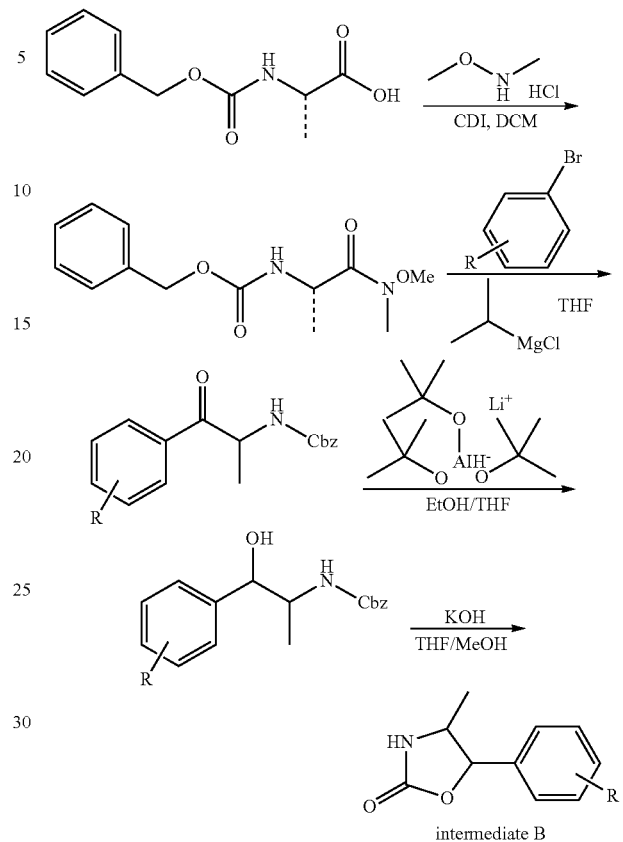

intermediate B

Substituted (4S,5R)-5-phenyl-4-methyl-1,3-oxazolidin-2-ones are prepared from commercially available N-Cbz L-alanine (Scheme B). Formation of the corresponding Weinreb amide and reaction with a known Grignard reagent provide the ketone adduct. Subsequent reduction of the ketone, followed by treatment with KOH results in the synthesis of intermediate B, with intermediates 4-7 as specific examples.

Intermediate 4

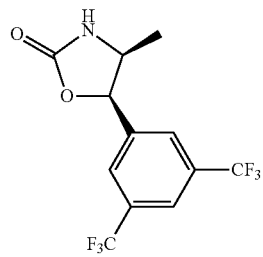 [SMILES: C[C@@H]1NC(=O)O[C@@H]1c1cc(C(F)(F)F)cc(C(F)(F)F)c1]

(4S,5R)-5-[3,5-Bis(trifluoromethyl)phenyl]-4-methyl-1,3-oxazolidin-2-one

The synthesis of INTERMEDIATE 4 has been described previously. See, for example, INTERMEDIATE 1 of WO2007081569.

The following intermediates (Table 1) were synthesized using commercially available materials by methods analogous to those described for INTERMEDIATE 1 of WO2007081569.

TABLE 1

| Intermediate | Molecular structure | LCMS (M + H)+ |
|---|---|---|
| 5 | 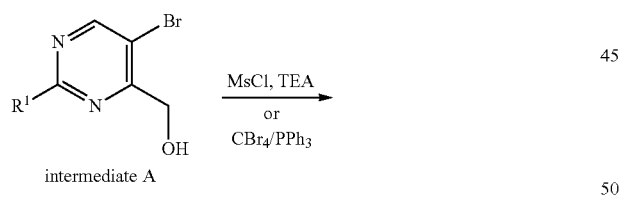 | 263.9 |
| 6 | 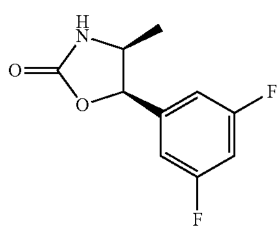 | 214.3 |
| 7 | 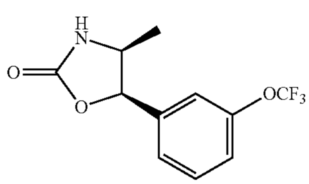 [SMILES: C[C@@H]1NC(=O)O[C@@H]1c1cccc(OC(F)(F)F)c1] | 262.1 |

Scheme C

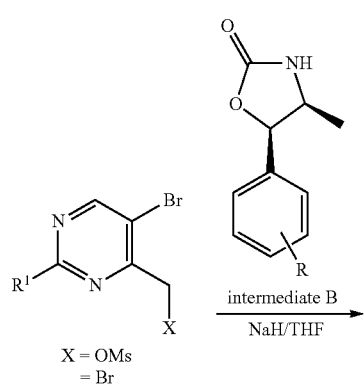

X = OMs
= Br

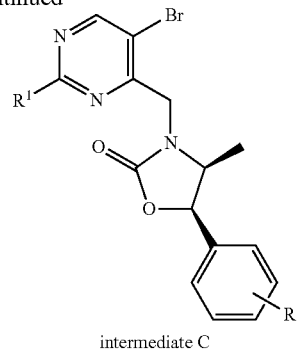

intermediate C

Intermediates of the type in scheme C can be synthesized from bromides or mesylates prepared from a prepared or known pyrimidinyl methyl alcohol (scheme A). Displacement by an oxazolidinone of the type prepared in scheme B results in intermediate C.

Intermediate 8

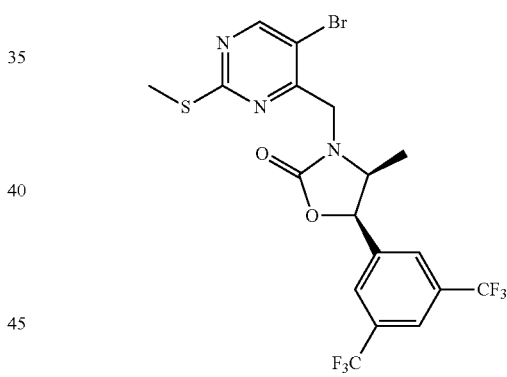

(4S,5R)-5-[3,5-Bis(trifluoromethyl)phenyl]-3-{[5-bromo-2-(methylsulfanyl)pyrimidin-4-yl]methyl}-4-methyl-1,3-oxazolidin-2-one The preparation of INTERMEDIATE 8 from INTERMEDIATES 1 and 4 has been described previously. See, for example, INTERMEDIATE 38 of WO2007081569.

Intermediates 9-12 in Table 2 were prepared in an analogous fashion to INTERMEDIATE 8 as described in Scheme C using precursors that are either commercially available or whose preparation is described above, specifically INTERMEDIATES 2, 3, 5, 6 and 7.

TABLE 2

| Compound | Structure | LCMS |
|---|---|---|
| 9 | 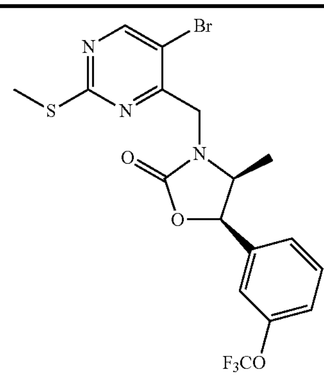 | 478.1/480.1 |
| 10 | 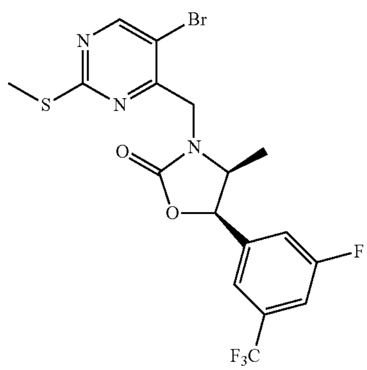 [SMILES: CSc1ncc(Br)c(CN2C(=O)O[C@H](c3cc(F)cc(C(F)(F)F)c3)[C@@H]2C)n1] | 479.9/481.9 |
| 11 | 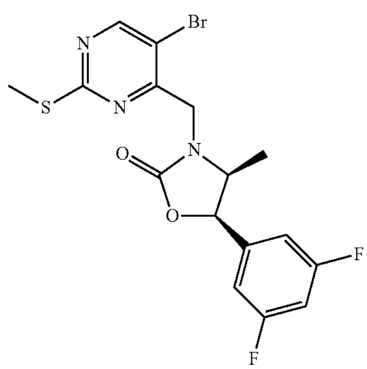 [SMILES: CSc1ncc(Br)c(CN2C(=O)O[C@H](c3cc(F)cc(F)c3)[C@@H]2C)n1] | 430.1/432.1 |
| 12 | 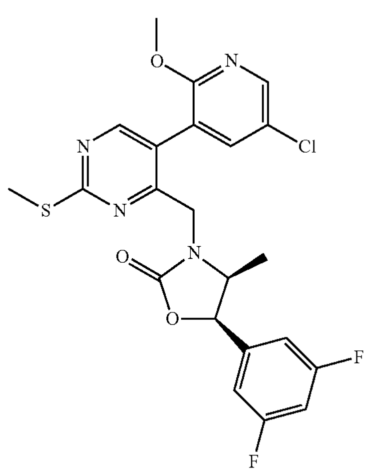 [SMILES: COc1ncc(Cl)cc1-c1cnc(SC)nc1CN1C(=O)O[C@H](c2cc(F)cc(F)c2)[C@@H]1C] | 493.3 |

Intermediate 13

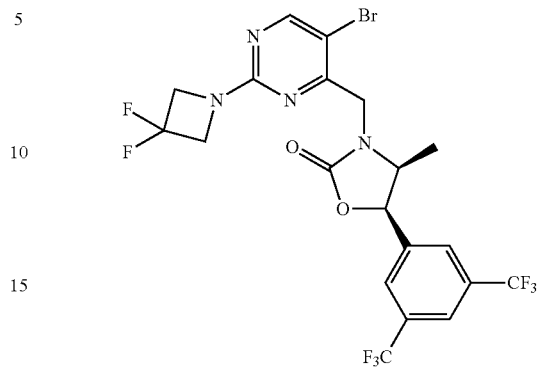

(4S,5R)-5-[3,5-Bis(trifluoromethyl)phenyl]-3-{[5-bromo-2-(3,3-difluoroazetidin-1-yl)pyrimidin-4-yl]methyl}-4-methyl-1,3-oxazolidin-2-one Step A: (4S,5R)-5-[3,5-Bis(trifluoromethyl)phenyl]-3-{[5-bromo-2-(methylsulfonyl)pyrimidin-4-yl]methyl}-4-methyl-1,3-oxazolidin-2-one To a suspension of (4S,5R)-5-[3,5-bis(trifluoromethyl)phenyl]-3-{[5-bromo-2-(methylsulfanyl)pyrimidin-4-yl]methyl}-4-methyl-1,3-oxazolidin-2-one (INTERMEDIATE 8, 10 g, 18.86 mmol) in acetonitrile (25 mL) and water (25 mL) was added potassium peroxymonosulfate (27.8 g, 45.3 mmol). After it was stirred at room for 14 hours, LCMS showed complete conversion of the starting material. It was distributed between water (200 mL) and t-butyl methyl ether (300 mL). The organic layer was washed with water (200 mL) and brine, dried over sodium sulfate, filtered and the filtrate concentrated to get the title compound (10.2 g, 96% yield) as a brightly white solid. LCMS (M+H)$^+$: 564.05. $^1$H NMR (CDCl$_3$, 500 MHz): δ 8.99 (s, 1H), 7.93 (s, 1H), 7.84 (s, 2H), 6.02 (d, 8.5 Hz, 1H), 5.14 (d, 18.5 Hz, 1H), 4.56 (m, 1H), 4.42 (d, 18.0 Hz, 1H), 3.37 (S, 3H), 0.86 (d, 6.5 Hz, 3H).

Step B: (4S,5R)-5-[3,5-Bis(trifluoromethyl)phenyl]-3-{[5-bromo-2-(3,3-difluoroazetidin-1-yl)pyrimidin-4-yl]methyl}-4-methyl-1,3-oxazolidin-2-one To a solution of (4S,5R)-5-[3,5-bis(trifluoromethyl)phenyl]-3-{[5-bromo-2-(methylsulfonyl)pyrimidin-4-yl]methyl}-4-methyl-1,3-oxazolidin-2-one (Step A, 2.5 g, 4.45 mmol), and 3,3-difluoroazetidine (1.73 g, 13.34 mmol) in THF (40 mL) was added diisopropylethylamine (3.88 mL, 22.23 mmol). It was stirred at 60° C. for 15 minutes at which time complete conversion by LCMS was noted. The solvent was evaporated, and the residue was purified on a silica gel column, eluting with 50% ethyl acetate in hexanes to get the title compound (2.2 g, 86% yield) as a white solid. LCMS (M+H)$^+$: 577.1; 575.2. $^1$H NMR (CDCl$_3$, 500 MHz): δ 8.38 (s, 1H), 7.93 (s, 1H), 7.81 (s, 2H), 5.82 (d, J=8.5 Hz, 1H), 4.84 (d, J=18.0 Hz, 1H), 4.48 (m, 4H), 4.40 (m, 1H), 4.23 (d, J=18.0 Hz, 1H), 0.83 (d, J=6.5 Hz, 3H).

Intermediates 14 and 15 in Table 3 were prepared in an analogous fashion to intermediate 13 using commercially available materials and precursors whose preparation is described above.

TABLE 3

| Compound | Structure | LCMS (M + H)+ |
|---|---|---|
| 14 | 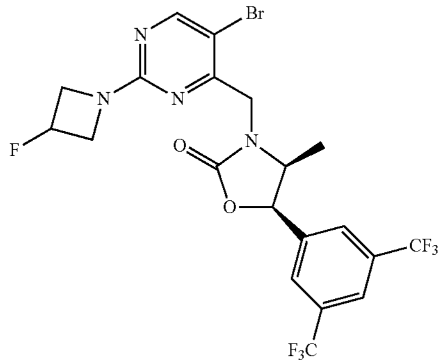 [SMILES: C[C@H]1[C@@H](c2cc(C(F)(F)F)cc(C(F)(F)F)c2)OC(=O)N1Cc1nc(N2CC(F)C2)ncc1Br] | 557.1/559.1 |
| 15 | 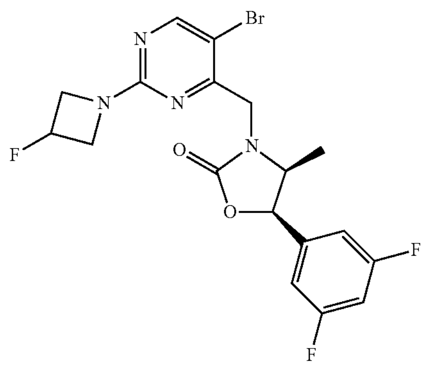 [SMILES: C[C@H]1[C@@H](c2cc(F)cc(F)c2)OC(=O)N1Cc1nc(N2CC(F)C2)ncc1Br] | 457.2/459.2 |

Intermediate 16

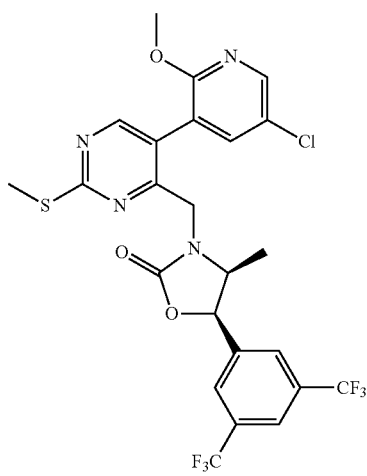 [SMILES: COc1ncc(Cl)cc1-c1cnc(SC)nc1CN1C(=O)O[C@H](c2cc(C(F)(F)F)cc(C(F)(F)F)c2)[C@@H]1C]

(4S,5R)-5-[3,5-Bis(trifluoromethyl)phenyl]-3-{[5-(5-chloro-2-methoxypyridin-3-yl)-2-(methylthio)pyrimidin-4-yl]methyl}-4-methyl-1,3-oxazolidin-2-one A dioxane (17.3 mL) solution of (4S,5R)-5-[3,5-bis(trifluoromethyl)phenyl]-4-methyl-3-{[2-(methylsulfanyl)-5-(4,4,5,5-tetramethyl-1,3,2-dioxaborolan-2-yl)pyrimidin-4-yl]methyl}-1,3-oxazolidin-2-one (INTERMEDIATE 21, 2.0 g, 3.46 mmol), 3-bromo-5-chloro-2-methoxypyridine (0.925 g, 4.16 mmol) and 2M potassium phosphate tribasic (3.5 mL, 7.00 mmol) in a microwave vial was evacuated and charged three times with nitrogen. Then Pd(Ph$_3$P)$_4$ (0.400 g, 0.346 mmol) was added and the reaction vial was capped. The reaction was stirred for 10 minutes at 170° C. in a microwave reactor. LCMS showed complete conversion to the product. The reaction was diluted with acetonitrile (5 mL) and filtered through a 2 g plug of RP C$_{18}$ silica, rinsing with 10 mL acetonitrile. The filtrate was concentrated and the crude was purified by silica gel chromatography, eluting with a gradient of 0-50% ethyl acetate/hexanes to give the title compound as a pale yellow foam. LCMS (M+H)+: 593.3

Intermediate 17

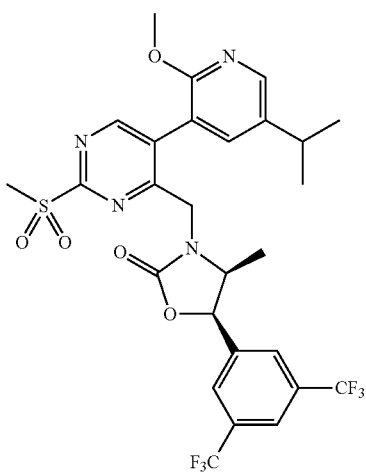 [SMILES: COc1ncc(C(C)C)cc1-c1cnc(S(C)(=O)=O)nc1CN1C(=O)O[C@H](c2cc(C(F)(F)F)cc(C(F)(F)F)c2)[C@@H]1C]

(4S,5R)-5-[3,5-Bis(trifluoromethyl)phenyl]-3-{[5-(5-isopropyl-2-methoxypyridin-3-yl)-2-(methylsulfonyl)pyrimidin-4-yl]methyl}-4-methyl-1,3-oxazolidin-2-one

Step A: (4S,5R)-5-[3,5-Bis(trifluoromethyl)phenyl]-3-{[5-(5-isopropyl-2-methoxypyridin-3-yl)-2-(methylthio)pyrimidin-4-yl]methyl}-4-methyl-1,3-oxazolidin-2-one (4S,5R)-5-[3,5-Bis(trifluoromethyl)phenyl]-3-{[5-bromo-2-(methylsulfanyl)pyrimidin-4-yl]methyl}-4-methyl-1,3-oxazolidin-2-one (INTERMEDIATE 8, 2.0 g, 3.77 mmol), 5-isopropyl-2-methoxypyridin-3-ylboronic acid (1.25 g, 4.53 mmol) and K$_2$CO$_3$ (1.56 g, 11.31 mmol) were added to a round bottom flask, which was then evacuated and charged with nitrogen 3 times. THF (15 mL) and water (3 mL) were then added. After evacuating and charging again with nitrogen, 1,1'-bis(di-tert-butylphosphino)ferrocene palladium dichloride (0.369 g, 0.566 mmol) was added and the reaction heated for 60 minutes at 50° C., at which time LCMS showed complete conversion to product. The reaction was diluted with 50 mL ethyl acetate and poured into 100 mL saturated NH$_4$Cl solution. The ethyl acetate layer was washed with brine (100 mL), then filtered through a 20 g plug of sodium sulfate, eluting with 50 mL ethyl acetate. The filtrate was concentrated prior to flash purification. The crude was purified by silica gel chromatography, eluting with a 0-20% ethyl acetate/hexanes gradient followed by isocratic elution at 20% ethyl acetate/hexanes. Pure fractions were concentrated to give product as colorless foam. LCMS (M+H)$^+$: 601.4.

Step B: (4S,5R)-5-[3,5-Bis(trifluoromethyl)phenyl]-3-{[5-(5-isopropyl-2-methoxypyridin-3-yl)-2-(methylsulfonyl)pyrimidin-4-yl]methyl}-4-methyl-1,3-oxazolidin-2-one Potassium peroxymonosulfate (4.08 g, 6.63 mmol) was added to an acetonitrile (12 mL) and water (8 mL) suspension of title compound from step A above (1.66 g, 2.76 mmol). This was then stirred for 2 hours at 25° C., at which time LCMS showed complete conversion to product. The reaction was diluted with methyl t-butyl ether (50 mL) and poured into water (100 mL). The organic layer was washed twice with 100 mL aqueous NaCl, then dried over sodium sulfate, filtered and the filtrate concentrated to give a white solid, which can be used without further purification. LCMS (M+H)$^+$: 633.4. $^1$H NMR (CDCl$_3$, 500 MHz) δ 8.75 (s, 1H), 8.24 (d, J=2.2 Hz, 1H), 7.92 (s, 1H), 7.80 (s, 2H), 7.49 (d, J=2.2 Hz, 1H), 5.89 (d, J=8.3 Hz, 1H), 4.93 (d, J=17.7 Hz, 1H), 4.59 (m, 1H), 4.26 (d, J=17.7 Hz, 1H), 3.98 (s, 3H), 3.43 (s, 3H), 3.02 (m, 1H), 1.33 (d, J=6.9 Hz, 6H), 0.80 (d, J=6.6 Hz, 3H).

Intermediate 18

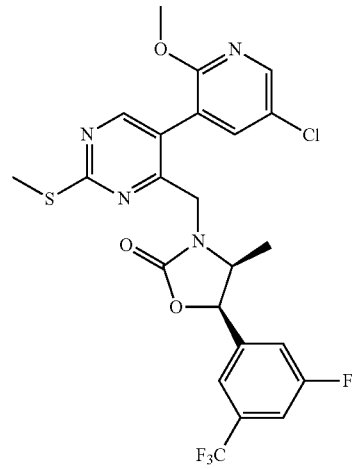 [SMILES: COc1ncc(Cl)cc1-c1cnc(SC)nc1CN1C(=O)O[C@H](c2cc(F)cc(C(F)(F)F)c2)[C@@H]1C]

(4S,5R)-3-{[5-(5-Chloro-2-methoxypyridin-3-yl)-2-(methylsulfanyl)pyrimidin-4-yl]methyl}-5-[3-fluoro-5-(trifluoromethyl)phenyl]-4-methyl-1,3-oxazolidin-2-one To a solution of (4S,5R)-3-{[5-bromo-2-(methylsulfanyl)pyrimidin-4-yl]methyl}-5-[3-fluoro-5-(trifluoromethyl)phenyl]-4-methyl-1,3-oxazolidin-2-one (INTERMEDIATE 10, 263 mg, 0.548 mmol) in THF (3.0 mL) was added 5-chloro-2-methoxy-3-(4,4,5,5-tetramethyl-1,3,2-dioxaborolan-2-yl)pyridine (221 mg, 0.821 mmol), 1,1'-bis(di-tert-butylphosphino)ferrocene palladium dichloride (17.8 mg, 0.027 mmol), and aqueous potassium carbonate (0.821 mL, 2.0 M). The mixture was degassed, flushed with nitrogen and heated to 40° C. for 18 hours. The reaction was diluted with ethyl acetate, washed with water, brine, dried over sodium sulfate, filtered and concentrated. The crude product was purified by silica gel chromatography to afford (4S,5R)-3-{[5-(5-chloro-2-methoxypyridin-3-yl)-2-(methylsulfanyl)pyrimidin-4-yl]methyl}-5-[3-fluoro-5-(trifluoromethyl)phenyl]-4-methyl-1,3-oxazolidin-2-one (211 mg, 0.389 mmol). LCMS (M+H)$^+$: 543.0.

Intermediate 19

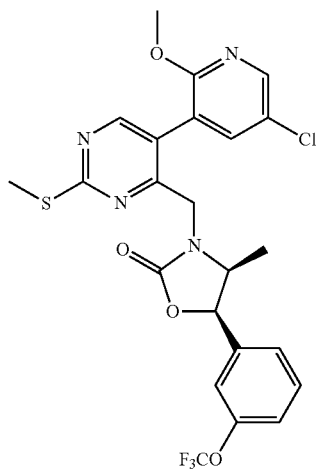 [SMILES: COc1ncc(Cl)cc1-c1cnc(SC)nc1CN1C(=O)O[C@H](c2cccc(OC(F)(F)F)c2)[C@@H]1C]

(4S,5R)-3-{[5-(5-Chloro-2-methoxypyridin-3-yl)-2-(methylthio)pyrimidin-4-yl]methyl}-4-methyl-5-[3-(trifluoromethoxy)phenyl]-1,3-oxazolidin-2-one (4S,5R)-3-{[5-Bromo-2-(methylthio)pyrimidin-4-yl]methyl}-4-methyl-5-[3-(trifluoromethoxy)phenyl]-1,3-oxazolidin-2-one (INTERMEDIATE 9, 345 mg, 0.721 mmol), 5-chloro-2-methoxypyridin-3-ylboronic acid (203 mg, 1.082 mmol) and $K_2CO_3$ (299 mg, 2.164 mmol) were added to a round bottom flask, which was then evacuated and charged with nitrogen 3 times. THF (4 mL) and water (0.4 mL) were then added. After evacuating and charging again with nitrogen, 1,1'-bis(di-tert-butylphosphino)ferrocene palladium dichloride (47.0 mg, 0.072 mmol) was added and the reaction heated for 60 minutes at 85° C. LCMS showed complete conversion to product. The reaction was diluted with 5 mL acetonitrile and filtered through a 1 g $C_{18}$ cartridge, eluting with 15 mL acetonitrile until the filtrate was colorless. The filtrate was then concentrated. Silica gel chromatography using a 0-30% ethyl acetate/hexanes linear gradient followed by an isocratic hold of 30% ethyl acetate/hexanes gave the title compound as a colorless oil. LCMS (M+H)⁺: 541.2.

Intermediate 20

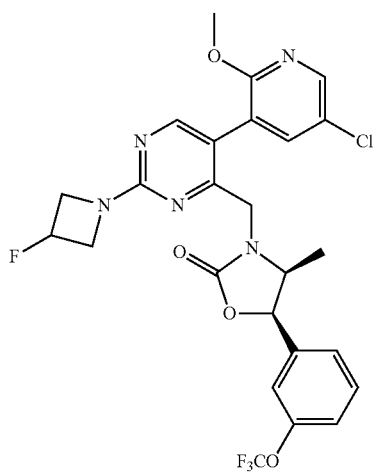 [SMILES: COc1ncc(Cl)cc1-c1cnc(N2CC(F)C2)nc1CN1C(=O)O[C@H](c2cccc(OC(F)(F)F)c2)[C@@H]1C]

(4S,5R)-3-((5-(5-Chloro-2-methoxypyridin-3-yl)-2-(3-fluoroazetidin-1-yl)pyrimidin-4-yl)methyl)-4-methyl-5-(3-(trifluoromethoxy)phenyl)oxazolidin-2-one Step A: (4S,5R)-3-{[5-(5-Chloro-2-methoxypyridin-3-yl)-2-(methylsulfonyl)pyrimidin-4-yl]methyl}-4-methyl-5-[3-(trifluoromethoxy)phenyl]-1,3-oxazolidin-2-one Potassium peroxymonosulfate (972 mg, 1.581 mmol) was added to an acetonitrile (4 mL)/water (2 mL) solution of (4S,5R)-3-{[5-(5-chloro-2-methoxypyridin-3-yl)-2-(methylthio)pyrimidin-4-yl]methyl}-4-methyl-5-[3-(trifluoromethoxy)phenyl]-1,3-oxazolidin-2-one (INTERMEDIATE 19, 380 mg, 0.702 mmol) at 25° C. The reaction was stirred for 16 hours at 25° C. followed by dilution with 100 mL methyl-t-butyl ether and 100 mL water. The organic layer was washed with 100 mL of aqueous NaCl three times. The organic layer was dried over sodium sulfate, filtered and the filtrate concentrated to give the title compound as a white solid, which can be used without further purification. LCMS (M+H)⁺: 573.3.

Step B: (4S,5R)-3-{[5-(5-Chloro-2-methoxypyridin-3-yl)-2-(3-fluoroazetidin-1-yl)pyrimidin-4-yl]methyl}-4-methyl-5-[3-(trifluoromethoxy)phenyl]-1,3-oxazolidin-2-one Triethylamine (0.499 mL, 3.58 mmol) was added to a THF (5 mL) solution of (4S,5R)-3-{[5-(5-chloro-2-methoxypyridin-3-yl)-2-(methylsulfonyl)pyrimidin-4-yl]methyl}-4-methyl-5-[3-(trifluoromethoxy)phenyl]-1,3-oxazolidin-2-one (Step A, 410 mg, 0.716 mmol) and 3-fluoroazetidine hydrochloride (300 mg, 2.69 mmol). The reaction was placed in an oil bath and heated for 20 minutes at 60° C. LCMS showed complete conversion to product. The reaction was diluted with ethyl acetate (50 mL) and poured into 0.1N HCl solution (50 mL). The ethyl acetate layer was washed with brine (50 mL), dried over sodium sulfate, filtered and the filtrate was concentrated on rotary evaporator. The crude isolate was purified by silica gel chromatography, eluting with a 0-50% ethyl acetate/hexanes linear gradient followed by a hold at 50% ethyl acetate/hexanes to give the title compound as a pale yellow solid. LCMS (M+H)⁺: 568.3. ¹H NMR (500 MHz, CDCl₃): δ 8.21 (d, J=2.3 Hz, 1H), 8.14 (s, 1H), 7.50 (d, J=2.4 Hz, 1H), 7.46 (t, J=7.9 Hz, 1H), 7.25 (m, 2H), 7.15 (s, 1H), 5.59 (d, J=8.4 Hz, 1H), 5.55 (m, 0.5H), 5.44 (m, 0.5H), 4.66 (d, J=17.1 Hz, 1H), 4.61 (m, 2H), 4.43 (m, 2H), 4.32 (m, 1H), 4.03 (d, J=17.5 Hz, 1H), 3.96 (s, 3H), 0.75 (d, J=6.5 Hz, 3H).

Intermediate 21

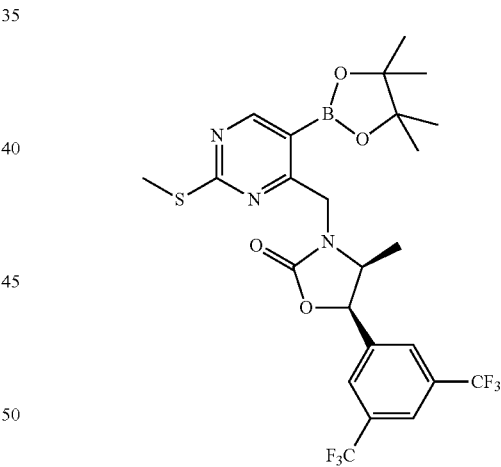

(4S,5R)-5-[3,5-Bis(trifluoromethyl)phenyl]-4-methyl-3-{[2-(methylsulfanyl)-5-(4,4,5,5-tetramethyl-1,3,2-dioxaborolan-2-yl)pyrimidin-4-yl]methyl}-1,3-oxazolidin-2-one A solution of (4S,5R)-5-[3,5-Bis(trifluoromethyl)phenyl]-3-{[5-bromo-2-(methylsulfanyl)pyrimidin-4-yl]methyl}-4-methyl-1,3-oxazolidin-2-one (INTERMEDIATE 8, 10 g, 18.86 mmol), bis(pinacolato)diboron (14.66 g, 56.6 mmol) and (2-dicyclohexylphosphino-2',4',6'-triisopropyl-1,1'-biphenyl)[2-(2-aminoethyl)phenyl)]palladium(II) chloride (XPHOS Biphenyl Precatalyst) (0.742 g, 0.94 mmol) in DMA (60 mL) was degassed. Added ground potassium acetate (5.74 g, 58.5 mmol) and degassed again. The slurry was heated to 80° C. overnight, at which time HPLC monitoring shows complete conversion. After cooling to room temperature, added 1.8 L MTBE and 0.9 L of 10% aq. NaCl. Partitioned, then added sodium sulfate and PL-TMT resin and stirred. Filtered, evaporated filtrate and purified the crude by silica gel chromatography, eluting with a gradient of 0-50% ethyl acetate/hexanes to give the title compound with some pinacol by-product. $^1$H NMR (CDCl$_3$, 500 MHz): δ 8.78 (s, 1H), 7.92 (s, 1H), 7.78 (s, 2H), 5.82 (d, 1H), 5.06 (d, 1H), 4.46 (m, 2H), 2.60 (s, 3H), 1.32 (s, 12H), 0.78 (d, 3H).

Intermediate 22

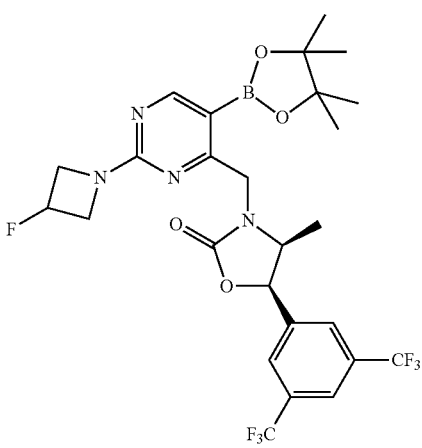 [SMILES: C[C@H]1[C@@H](c2cc(C(F)(F)F)cc(C(F)(F)F)c2)OC(=O)N1Cc1nc(N2CC(F)C2)ncc1B1OC(C)(C)C(C)(C)O1]

(4S,5R)-5-[3,5-Bis(trifluoromethyl)phenyl]-3-{[2-(3-fluoroazetidin-1-yl)-5-(4,4,5,5-tetramethyl-1,3,2-dioxaborolan-2-yl)pyrimidin-4-yl]methyl}-4-methyl-1,3-oxazolidin-2-one A stirred suspension of (4S,5R)-5-[3,5-bis(trifluoromethyl)phenyl]-3-{[5-bromo-2-(3-fluoroazetidin-1-yl)pyrimidin-4-yl]methyl}-4-methyl-1,3-oxazolidin-2-one (INTERMEDIATE 14, 700 mg, 1.256 mmol), bis(pinacolato)diboron (797 mg, 3.14 mmol) and potassium acetate (616 mg, 6.28 mmol) in 1,4-dioxane (9 mL) was bubbled with nitrogen for 10 minutes. 1,1'-Bis(diphenylphosphino)ferrocene palladium(II)dichloride dichloromethane complex (103 mg, 0.126 mmol) was then added, after which the reaction was evacuated and charged with nitrogen. The reaction was heated at 80° C. for 3.5 hours. LCMS showed the desired product along with proto-deboryalated product and the boronic acid. The reaction was diluted with ethyl acetate (200 mL) and water (50 mL). The organic layer was washed with water, brine, filtered and concentrated under reduced pressure. The residue was purified by silica gel chromatography, eluting with 5, 20, 25 and 30% ethyl acetate in heptane to give the boronate ester (70 mg, 0.116 mmol, 9.22% yield) as a slightly yellow solid. LCMS (M+H)$^+$: 605.4.

Scheme D

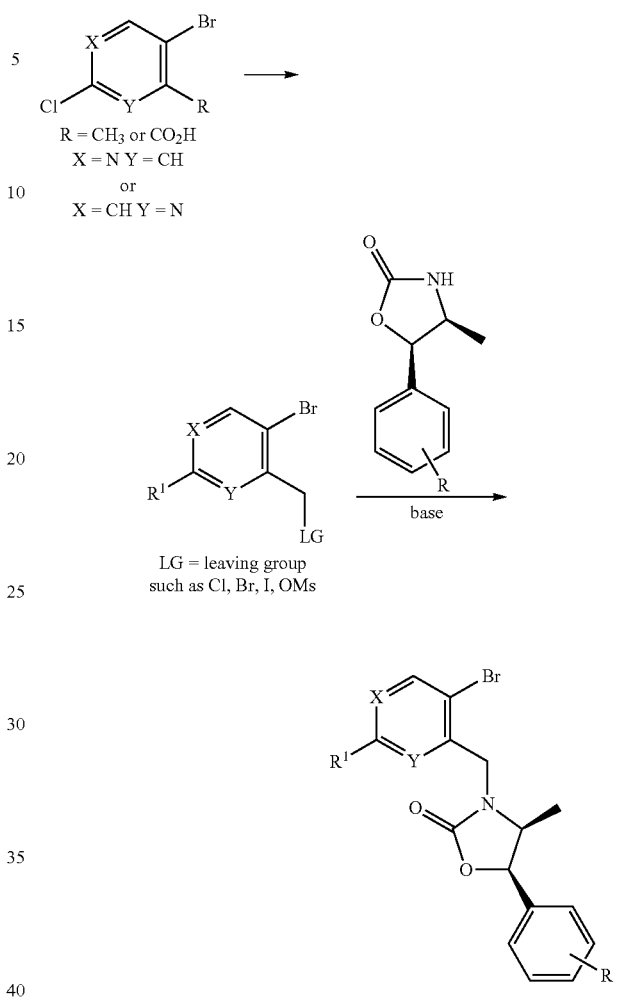

Intermediates of the type in scheme D can be synthesized from bromides or mesylates prepared from a prepared or known appropriately substituted methyl pyridine or nicotinic/isonicotinic acid. Displacement of the installed leaving group by an oxazolidinone of the type prepared in scheme B results in intermediate D.

Intermediate 23

3-Bromo-2-(bromomethyl)-6-chloropyridine

The preparation of this precursor from commercially available 6-chloro-3-bromo-2-methylpyridine has been described previously in WO2007081569, INTERMEDIATE 9 Step B.

Intermediate 24

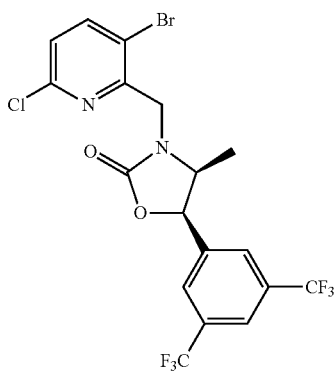 [SMILES: C[C@H]1[C@@H](c2cc(C(F)(F)F)cc(C(F)(F)F)c2)OC(=O)N1Cc1nc(Cl)ccc1Br]

(4S,5R)-5-[3,5-Bis(trifluoromethyl)phenyl]-3-[(3-bromo-6-chloropyridin-2-yl)methyl]-4-methyl-1,3-oxazolidin-2-one The synthesis of INTERMEDIATE 24 has been described previously. See, for example, INTERMEDIATE 9 of WO2007081569.

Intermediate 25

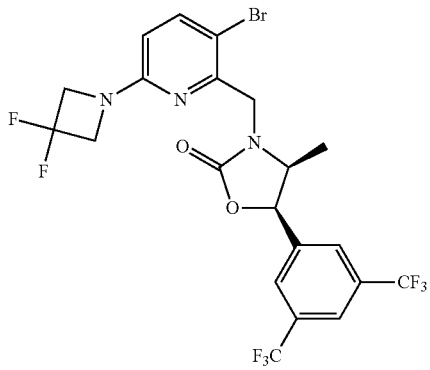 [SMILES: C[C@H]1[C@@H](c2cc(C(F)(F)F)cc(C(F)(F)F)c2)OC(=O)N1Cc1nc(N2CC(F)(F)C2)ccc1Br]

(4S,5R)-5-[3,5-Bis(trifluoromethyl)phenyl]-3-{[3-bromo-6-(3,3-difluoroazetidin-1-yl)pyridin-2-yl]methyl}-4-methyl-1,3-oxazolidin-2-one To a solution of (4S,5R)-5-[3,5-bis(trifluoromethyl)phenyl]-3-[(3-bromo-6-chloropyridin-2-yl)methyl]-4-methyl-1,3-oxazolidin-2-one (INTERMEDIATE 24, 2.2 g, 4.25 mmol) in DMSO (25 mL) under nitrogen, were added 3,3-difluoroazetidine hydrochloride (2.75 g, 21.3 mmol) and sodium bicarbonate (2.14 g, 25.5 mmol). The resulting mixture was stirred at 150° C. overnight. Water was added and extracted 3 times with ethyl acetate. The combined organic layers were washed with brine, dried over sodium sulfate, filtered, and the solvent was evaporated under reduced pressure. The residue was purified by flash column chromatography on silica gel, eluting with ethyl acetate in hexanes to afford the titled compound. $^1$H NMR (CDCl$_3$, 500 MHz) δ 7.89 (s, 1H), 7.78 (s, 2H), 7.63 (d, J=8.7 Hz, 1H), 6.24 (d, J=8.7 Hz, 1H), 5.75 (d, J=8.4 Hz, 1H), 4.87 (d, J=17.1 Hz, 1H), 4.23-4.40 (m, 6H), 0.79 (d, J=7.6 Hz, 3H).

Intermediate 26

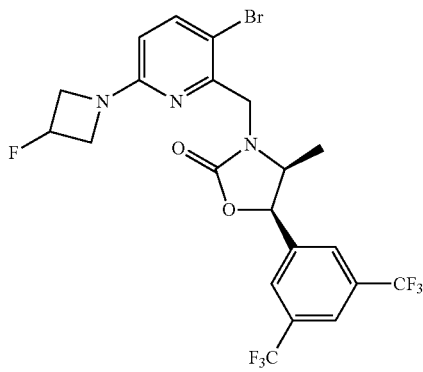 [SMILES: C[C@H]1[C@@H](c2cc(C(F)(F)F)cc(C(F)(F)F)c2)OC(=O)N1Cc1nc(N2CC(F)C2)ccc1Br]

(4S,5R)-5-[3,5-Bis(trifluoromethyl)phenyl]-3-{[3-bromo-6-(3-fluoroazetidin-1-yl)pyridin-2-yl]methyl}-4-methyl-1,3-oxazolidin-2-one To a solution of (4S,5R)-5-[3,5-bis(trifluoromethyl)phenyl]-3-[(3-bromo-6-chloropyridin-2-yl)methyl]-4-methyl-1,3-oxazolidin-2-one (INTERMEDIATE 24, 2.0 g, 3.86 mmol) in DMSO (25 mL), under nitrogen, were added 3-fluoroazetidine hydrochloride (2.16 g, 19.3 mmol) and sodium bicarbonate (1.95 g, 23.2 mmol). The resulting mixture was stirred at 150° C. overnight. The reaction mixture was quenched with water, then extracted 3 times with ethyl acetate. The combined organic layers were washed with brine, dried over sodium sulfate, filtered, and the solvent was evaporated under reduced pressure. The residue was purified by flash column chromatography on silica gel, eluting with ethyl acetate in hexanes to afford the titled compound. $^1$H NMR (500 MHz, CDCl$_3$): δ 7.92 (s, 1H); 7.81 (s, 2H); 7.60 (d, J=8.5 Hz, 1H); 6.20 (d, J=8.6 Hz, 1H); 5.79 (d, J=8.6 Hz, 1H); 5.52 (m, 0.5H); 5.40 (m, 0.5H); 4.90 (d, J=16.9 Hz, 1H); 4.40-4.24 (m, 4H); 4.20-4.09 (m, 2H); 0.82 (d, J=6.6 Hz, 3H).

Intermediate 27

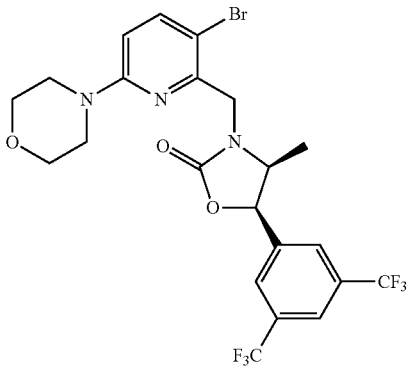 [SMILES: C[C@H]1[C@@H](c2cc(C(F)(F)F)cc(C(F)(F)F)c2)OC(=O)N1Cc1nc(N2CCOCC2)ccc1Br]

(4S,5R)-5-[3,5-Bis(trifluoromethyl)phenyl]-3-{[3-bromo-6-(morpholin-4-yl)pyridin-2-yl]methyl}-4-methyl-1,3-oxazolidin-2-one Triethylamine (3.23 mL, 23.18 mmol), morpholine (1.683 mL, 19.32 mmol), (4S,5R)-5-[3,5-bis(trifluoromethyl)phenyl]-3-[(3-bromo-6-chloropyridin-2-yl)methyl]-4-methyl-1,3-oxazolidin-2-one (INTERMEDIATE 24, 2 g, 3.86 mmol) and 1,4-dioxane (10.0 mL) were mixed in a 20 mL microwave vial, capped and heated at 140° C. for 6 hours in microwave with monitoring by TLC and LCMS. Once the reaction was determined to be complete, the reaction mixture was diluted with ethyl acetate, washed with saturated aqueous NaHCO$_3$, water and brine. The organic phase was dried with Na$_2$SO$_4$, filtered and the filtrate concentrated. The crude was purified by silica gel chromatography in 30% ethyl acetate/hexanes to give the titled compound (1.8 g, 3.17 mmol, 82% yield) as white solid. LCMS (M+H)$^+$: 569.9. $^1$H NMR (CDCl$_3$, 500 MHz): δ 7.93 (s, 1H), 7.80 (s, 2H), 7.63 (dd, 1H), 6.52 (d, 1H), 5.75 (d, 1H), 4.91 (d, 1H), 4.32 (d, 1H), 4.28 (t, 1H), 3.87-3.84 (t, 4H), 3.57-3.48 (m, 4H), 0.83 (d, 3H).

Intermediate 28

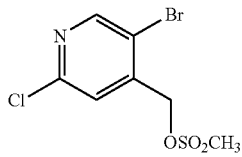

(5-Bromo-2-chloropyridin-4-yl)methyl methanesulfonate

Step A: (5-Bromo-2-chloropyridin-4-yl)methanol

A 0° C. solution of 5-bromo-2-chloroisonicotinic acid (5.008 g, 21.18 mmol) in THF (30 mL) was treated with borane tetrahydrofuran complex (52.9 ml, 52.9 mmol). The solution was stirred at room temperature for 16 hours. The reaction was slowly quenched with water until gas formation stopped. Then 25 mL of 3 N NaOH was added and the resulting mixture was heated in a 100° C. oil bath for about 75 minutes. The reaction was cooled and the volatiles removed by rotary evaporation. Ethyl acetate and brine were added, after which the layers were separated. The organic was dried over Na$_2$SO$_4$, filtered and the filtrate concentrated and dried to give a yellow solid that was used without further purification. $^1$H NMR (CDCl$_3$, 500 MHz): δ 8.41 (s, 1H), 7.58 (s, 1H), 4.74 (s, 2H), 2.23 (br, 1H).

Step B: (5-Bromo-2-chloropyridin-4-yl)methyl methanesulfonate

A 0° C. solution of (5-bromo-2-chloropyridin-4-yl)methanol (1.96 g, 8.81 mmol) in CH$_2$Cl$_2$ (25 mL) was treated with triethylamine (2.456 ml, 17.62 mmol) and methanesulfonyl chloride (0.824 ml, 10.57 mmol). The reaction was stirred at room temperature for 1 hour. The reaction was diluted with additional CH$_2$Cl$_2$, then washed with aqueous NaHCO$_3$, followed by brine. The organic was dried over sodium sulfate, filtered and the filtrate evaporated. The crude was purified by silica gel chromatography to give the titled compound. $^1$H NMR (CDCl$_3$, 500 MHz): δ 8.50 (s, 1H), 7.47 (s, 1H), 5.24 (s, 2H), 3.16 (s, 3H).

Intermediate 29

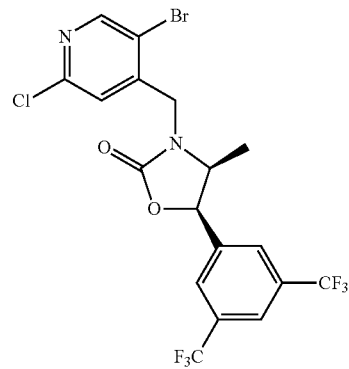 [SMILES: C[C@H]1[C@@H](c2cc(C(F)(F)F)cc(C(F)(F)F)c2)OC(=O)N1Cc1cc(Cl)ncc1Br]

(4S,5R)-5-[3,5-Bis(trifluoromethyl)phenyl]-3-[(5-bromo-2-chloropyridin-4-yl)methyl]-4-methyl-1,3-oxazolidin-2-one A solution of (4S,5R)-5-[3,5-bis(trifluoromethyl)phenyl]-4-methyl-1,3-oxazolidin-2-one (INTERMEDIATE 4, 1.305 g, 4.17 mmol) in 30 mL of DMF was cooled to −20° C. NaHMDS (1.0 M, 4.17 ml, 4.17 mmol) was added and the reaction was stirred at −20° C. for 20 minutes. Next, a solution of (5-bromo-2-chloropyridin-4-yl)methyl methanesulfonate (INTERMEDIATE 28, 1.2522 g, 4.17 mmol) in 5 mL of DMF was added and the solution turned brown. The reaction was warmed to 0° C. by switching to an ice/water bath and the reaction stirred for an additional 30 minutes, at which time an LCMS aliquot confirmed the reaction was complete. It was quenched with aqueous NaHCO$_3$. The reaction was extracted with ethyl acetate, then washed with aqueous NaHCO$_3$ and brine, dried with Na$_2$SO$_4$, filtered and the filtrate was concentrated. The crude oil was purified by silica gel chromatography to give the titled compound as an off-white solid. $^1$H NMR (CDCl$_3$, 500 MHz): δ 8.52 (s, 1H), 7.92 (s, 1H), 7.80 (s, 2H), 7.36 (s, 1H), 5.81 (d, 1H), 4.78 (d, 1H), 4.34 (d, 1H), 4.17 (m, 1H), 0.82 (d, 3H).

Intermediate 30

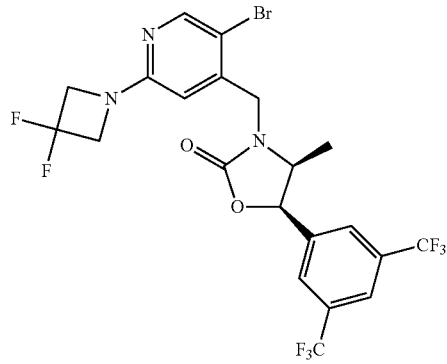 [SMILES: C[C@H]1[C@@H](c2cc(C(F)(F)F)cc(C(F)(F)F)c2)OC(=O)N1Cc1cc(N2CC(F)(F)C2)ncc1Br]

(4S,5R)-5-[3,5-Bis(trifluoromethyl)phenyl]-3-{[5-bromo-2-(3,3-difluoroazetidin-1-yl)pyridin-4-yl]methyl}-4-methyl-1,3-oxazolidin-2-one Intermediate 29 is treated with 3,3-difluoroazetidine hydrochloride and sodium bicarbonate as in the preparation of INTERMEDIATE 25. $^1$H NMR (500 MHz, CDCl$_3$): δ 8.30 (s, 1H); 7.93 (s, 1H); 7.81 (s, 2H); 6.46 (s, 1H); 5.76 (d, J=8.0 Hz, 1H); 4.75 (d, J=15.9 Hz, 1H); 4.42-4.31 (m, 5H); 4.18-4.15 (m, 1H); 0.84 (d, J=6.6 Hz, 3H).

Scheme E

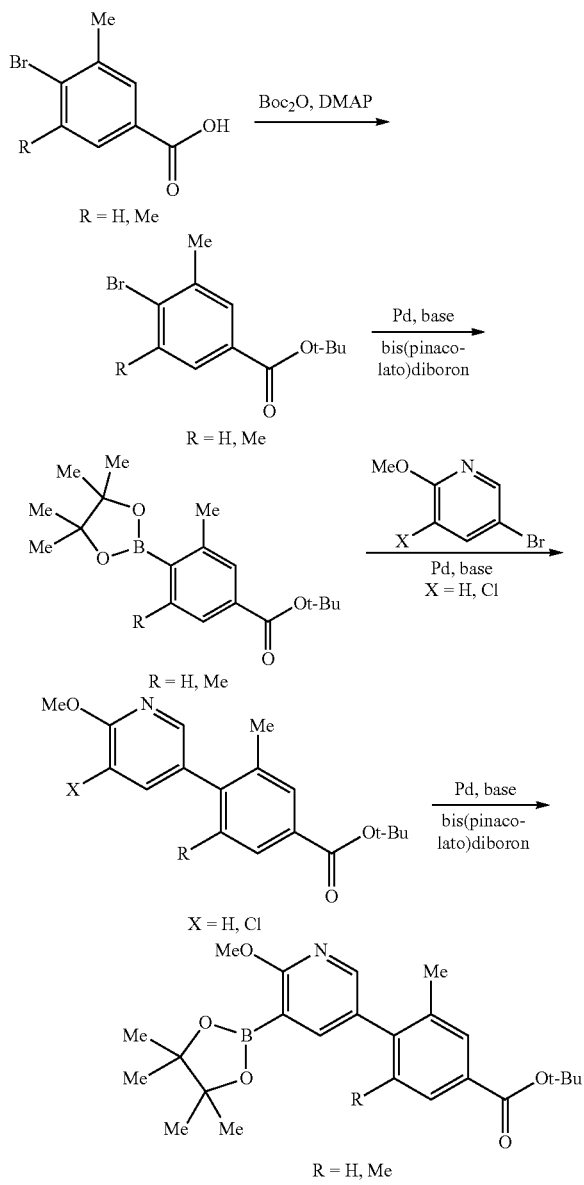

When X = H, Br$_2$/HOAc/KOAc/heat converts to X = Br
R = H, Me

Preparation of biaryl intermediate type E begins with the formation of a tert-butyl ester of a para-bromo benzoic acid, which is then subjected to a Miyaura coupling to obtain the corresponding boronic ester. Alternatively, other 4-substituted alkyl esters of benzoic acids can be used in this sequence, some of which are commercially available as the bromide, boronate ester, or boronic acid. Suzuki coupling of the boronate with a commercially available 5-bromo-2-methoxypyridine (where C$_3$=H or Cl) yields the initial biaryl precursor. If C$_3$ is H on the methoxypyridine, treatment with bromine in KOAc buffered acetic acid provides a suitable borylation substrate; the 3-chloro compound is already a suitable borylation substrate. A second Miyaura coupling provides the desired boronic ester intermediate type E. The preparation of INTERMEDIATE 31 provides a detailed description of this sequence; INTERMEDIATES 32-38 can also be prepared utilizing these steps.

Intermediate 31

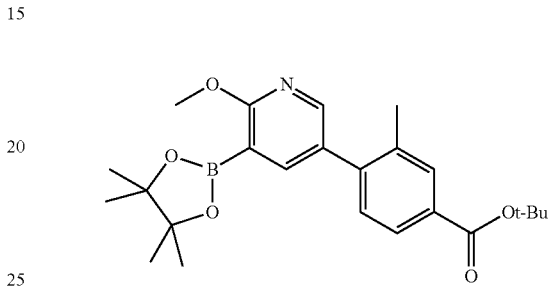

tert-Butyl 4-[6-methoxy-5-(4,4,5,5-tetramethyl-1,3,2-dioxaborolan-2-yl)pyridin-3-yl]-3-methylbenzoate Step A: tert-Butyl 4-bromo-3-methylbenzoate To a 250 mL round bottomed flask was added 4-bromo-3-methylbenzoic acid (10 g, 46.5 mmol), DMAP (8.52 g, 69.8 mmol) and tert-butyl alcohol (100 mL). Di-tert-butyl dicarbonate (12.96 mL, 55.8 mmol) was added via a syringe to the solution, which caused vigorous bubbling, foaming and the loss of some material. The remaining reaction mixture was heated at 70° C. overnight. The reaction was cooled to room temperature and the volatiles were removed under reduced pressure. The crude material was diluted with ethyl acetate:hexanes (1:4, 200 mL), then washed sequentially with 5% aqueous KOH (200 mL) and saturated aqueous ammonium chloride (2×100 mL). The organics were dried over sodium sulfate, filtered and the filtrate concentrated before purification by column chromatography. tert-Butyl 4-bromo-3-methylbenzoate was isolated as a colorless oil (7.2 g, 26.6 mmol). $^1$H NMR (500 MHz, CDCl$_3$) δ 7.87 (s, 1H), 7.67 (d, J=8.3 Hz, 1H), 7.60 (d, J=8.2 Hz, 1H), 2.47 (s, 3H), 1.62 (s, 9H).

Step B: tert-Butyl 3-methyl-4-(4,4,5,5-tetramethyl-1,3,2-dioxaborolan-2-yl)benzoate To a 250 mL round bottomed flask was loaded 1,1'-bis(di-tert-butylphosphino)ferrocene palladium dichloride (0.317 g, 0.487 mmol), tert-butyl 4-bromo-3-methylbenzoate (Step A, 6.6 g, 24.34 mmol), bis(pinacolato)diboron (7.42 g, 29.2 mmol), potassium acetate (5.97 g, 60.9 mmol) and dioxane (25 mL). The system was flushed with nitrogen and was heated at 125° C. overnight. The reaction was cooled to room temperature and was diluted ethyl acetate:hexanes (1:9, 120 mL), then washed sequentially with water (150 mL) and brine (50 mL). The organics were dried over sodium sulfate, filtered and the filtrate concentrated before purification by column chromatography. tert-Butyl 3-methyl-4-(4,4,5,5-tetramethyl-1,3,2-dioxaborolan-2-yl)benzoate was isolated as a crystalline solid (6.6 g, 14.5 mmol). Note $^1$H NMR indicated it is about 70% pure. ¹H NMR (500 MHz, CDCl₃) δ 7.8 (m, 3H), 2.60 (s, 3H), 1.58 (s, 9H), 1.39 (s, 12H).

Step C: tert-Butyl 4-(5-chloro-6-methoxypyridin-3-yl)-3-methylbenzoate

To a 250 mL round bottomed flask was added 5-bromo-3-chloro-2-methoxypyridine (1.5 g), tribasic potassium phosphate (2.86 g, 13.5 mmol), bis(diphenylphosphino)ferrocene]palladium (II) dichloromethane adduct (0.275 g, 6.74 mmol), tert-butyl 3-methyl-4-(4,4,5,5-tetramethyl-1,3,2-dioxaborolan-2-yl)benzoate (Step B, 2.27 g, 7.13 mmol), dioxane (50 mL) and water (3 mL). The flask was sealed and was stirred at 80° C. overnight. The reaction was cooled to room temperature, diluted with ethyl acetate, washed with water, filtered and the filtrate concentrated. The resultant residue was purified by silica gel chromatography to yield tert-butyl 4-(5-chloro-6-methoxypyridin-3-yl)-3-methylbenzoate (2.0 g, 5.99 mmol). LCMS (M+H)⁺: 334.0

Step D: tert-Butyl 4-[6-methoxy-5-(4,4,5,5-tetramethyl-1,3,2-dioxaborolan-2-yl)pyridin-3-yl]-3-methylbenzoate To a 250 mL round bottomed flask was added tert-butyl 4-(5-chloro-6-methoxypyridin-3-yl)-3-methylbenzoate (Step C, 4.5 g, 13.5 mmol), bis(pinacolato)diboron (6.85 g, 27.0 mmol), potassium acetate (3.97 g, 40.4 mmol), and chloro(2-dicyclohexylphosphino-2',4',6'-triisopropyl-1,1'-biphenyl)[2-(2'-amino-1,1'-biphenyl)]palladium(II) (0.212 g, 0.27 mmol) followed by anhydrous dioxane (50 mL). The system was evacuated and backfilled with nitrogen three times and was heated to 120° C. for 2 hours. The mixture was cooled, filtered over celite (ethyl acetate wash) and was concentrated. The residue was purified by silica gel chromatography to afford tert-butyl 4-[6-methoxy-5-(4,4,5,5-tetramethyl-1,3,2-dioxaborolan-2-yl)pyridin-3-yl]-3-methylbenzoate as a solid (4.3 g, 10.11 mmol). LCMS (M+H)⁺: 426.0.

Intermediate 32

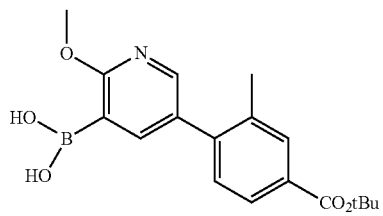 [SMILES: COc1ncc(-c2ccc(C(=O)OC(C)(C)C)cc2C)cc1B(O)O]

{5-[4-(tert-Butoxycarbonyl)-2-methylphenyl]-2-methoxypyridin-3-yl}boronic acid

A solution of tert-butyl 4-[6-methoxy-5-(4,4,5,5-tetramethyl-1,3,2-dioxaborolan-2-yl)pyridin-3-yl]-3-methylbenzoate (INTERMEDIATE 31, 16.0 g, 37.6 mmol), HCl (150 mL, 150 mmol), sodium periodate (24.14 g, 113 mmol) and ethyl acetate (150 mL) was stirred rapidly at room temperature for 1 hour, at which time LCMS showed complete boronate ester hydrolysis. The reaction was diluted with some water and extracted with ethyl acetate. The organic layer was dried over sodium sulfate, filtered and the filtrate concentrated. The crude was purified by silica gel chromatography to give the title compound. LCMS (M+H)⁺: 343.95. ¹H NMR (500 MHz, CDCl₃) δ 8.24 (d, 1H), 8.14 (d, 1H), 7.93 (s, 1H) 7.88 (d, 1H), 7.28 (d, 1H), 5.84 (br, 2H) 4.13 (s, 3H), 2.35 (s, 3H), 1.64 (s, 9H).

Intermediate 33

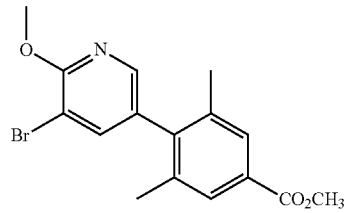

Methyl 4-(5-bromo-6-methoxypyridin-3-yl)-3,5-dimethylbenzoate

Step A: Methyl 3,5-dimethyl-4-(4,4,5,5-tetramethyl-1,3,2-dioxaborolan-2-yl)benzoate A solution of 4-bromo-3,5-dimethylbenzoic acid methyl ester (2.0 g, 8.23 mmol), bis(pinacolato)diboron (2.298 g, 9.05 mmol) and potassium acetate (2.422 g, 24.68 mmol) in 1,4-dioxane (41 mL) was sparged with nitrogen for 45 minutes. Added (2-dicyclohexylphosphino-2',4',6'-triisopropyl-1,1'-biphenyl)[2-(2-aminoethyl)phenyl)]palladium(II) chloride (XPHOS Biphenyl Precatalyst) (0.162 g, 0.206 mmol) to the reaction, evacuated and charged three times with nitrogen, then heated to 100° C. The reaction was monitored by LCMS for completion. At completion the reaction was cooled to room temperature and partitioned between water and ethyl acetate. The organic was washed a second time with water, dried over sodium sulfate, filtered and evaporated. The crude was purified by silica gel chromatography, eluting with 33-100% CH₂Cl₂/hexanes to give the title compound. ¹H NMR (CDCl₃, 500 MHz) δ7.60 (s, 2H), δ3.88 (s, 3H), δ2.43 (s, 6H), δ1.40 (s, 12H).

Step B: Methyl 4-(6-methoxypyridin-3-yl)-3,5-dimethylbenzoate

Methyl 3,5-dimethyl-4-(4,4,5,5-tetramethyl-1,3,2-dioxaborolan-2-yl)benzoate (Step A, 2.79 g, 7.20 mmol), 1,1'-bis(di-tert-butylphoshino)ferrocene palladium dichloride (0.391 g, 0.600 mmol) and 5-bromo-2-methoxypyridine (0.776 mL, 6 mmol) were mixed in a reaction flask which was then evacuated and charged with nitrogen three times. Added 1,4-dioxane (30.0 mL) and 3.0M aqueous potassium carbonate (6.00 mL, 18.00 mmol), evacuated and charged with nitrogen (3×), then stirred overnight at 80° C. The reaction was then partitioned between ethyl acetate and water. After a second water wash, the organic was dried over sodium sulfate, filtered and evaporated. The crude was purified by silica gel chromatography, eluting with 10 column volumes of 4% ethyl acetate/hexanes followed by a gradient of 4-10% ethyl acetate/hexanes over 10 column volumes to give the title compound. ¹H NMR (CDCl₃, 500 MHz) δ7.94 (d, 1H), δ7.79 (s, 2H), δ7.36 (dd, 1H), δ6.84 (d, 1H), δ4.00 (s, 3H), δ3.93 (s, 3H), δ2.09 (s, 6H).

Step C: Methyl 4-(5-bromo-6-methoxypyridin-3-yl)-3,5-dimethylbenzoate

Methyl 4-(6-methoxypyridin-3-yl)-3,5-dimethylbenzoate (Step B, 1.31 g, 4.83 mmol) and potassium acetate (2.369 g, 24.14 mmol) were dissolved in acetic acid (24 mL). Bromine (0.622 mL, 12.07 mmol) was added and the reaction was stirred at 80° C. The reaction was monitored by LCMS. Once complete, it was cooled to room temperature, diluted with ethyl acetate and added to a separatory funnel. Aqueous sodium hydroxide was added to neutralize the reaction. The reaction was partitioned between water and ethyl acetate, and the aqueous was extracted a second time with ethyl acetate. The combined organics were washed with brine, then dried over sodium sulfate, filtered and evaporated. The crude isolate was purified by silica gel chromatography, eluting with 2 column volumes of 4% Ethyl acetate in hexanes, followed by a gradient of 4-10% ethyl acetate/hexanes over 6 column volumes, followed by a gradient of 10-20% ethyl acetate/hexanes over 5 column volumes to give the title compound. $^1$H NMR (CDCl$_3$, 500 MHz) δ7.88 (d, 1H), 67.79 (s, 2H), 67.63 (d, 1H), 64.07 (s, 3H), 63.93 (s, 3H), 62.11 (s, 6H).

Intermediates 34-38

The following intermediates were prepared by methods analogous to INTERMEDIATES 31 and 33 using commercially available materials or intermediates described herein.

| INTERMEDIATE | STRUCTURE | LCMS (M + H)$^+$ |
|---|---|---|
| 34 | 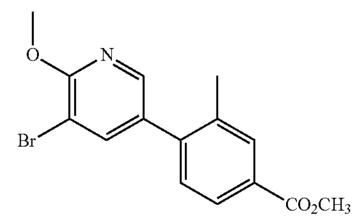 [SMILES: COC(=O)c1ccc(-c2cnc(OC)c(Cl)c2)c(C)c1] | 336.2/338.2 |
| 35 | 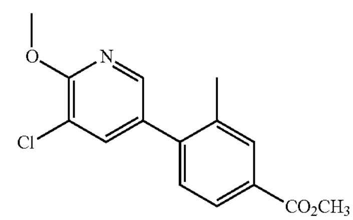 | 292.0 |
| 36 | 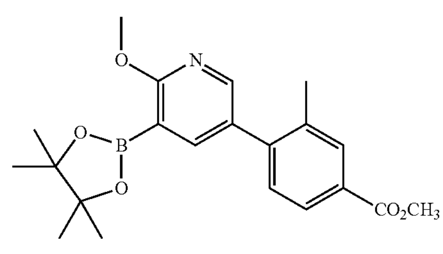 [SMILES: COC(=O)c1ccc(-c2cnc(OC)c(B3OC(C)(C)C(C)(C)O3)c2)c(C)c1] | 384.1 |
| 37 | 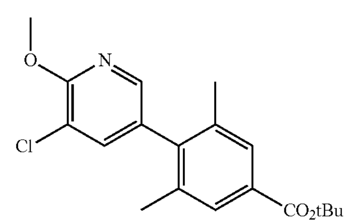 [SMILES: COc1ncc(-c2c(C)cc(C(=O)OC(C)(C)C)cc2C)cc1Cl] | 348.1 |
| 38 | 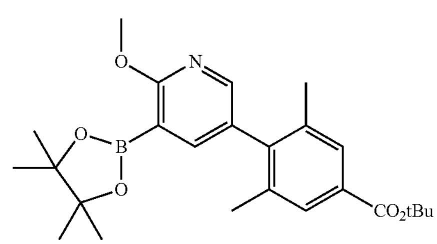 [SMILES: COc1ncc(-c2c(C)cc(C(=O)OC(C)(C)C)cc2C)cc1B1OC(C)(C)C(C)(C)O1] | 440.1 |

Intermediate 39

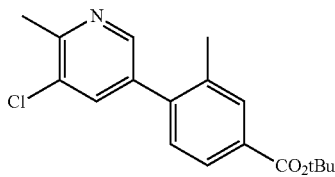 [SMILES: Cc1cc(C(=O)OC(C)(C)C)ccc1-c1cnc(C)c(Cl)c1]

tert-Butyl 4-(5-chloro-6-methylpyridin-3-yl)-3-methylbenzoate

Step A: tert-Butyl 4-(5,6-dichloropyridin-3-yl)-3-methylbenzoate

A suspension of tert-butyl 3-methyl-4-(4,4,5,5-tetramethyl-1,3,2-dioxaborolan-2-yl)benzoate (from INTERMEDIATE 31 Step B, 1.0 g, 3.14 mmol), 5-bromo-2,3-dichloropyridine (0.784 g, 3.46 mmol), potassium phosphate (1.33 g, 6.29 mmol), 1,1'-bis(diphenylphosphino)ferrocene-palladium(II)dichloride dichloromethane complex (0.077 g, 0.094 mmol) in dioxane (12 mL) and water (1 mL) was flushed with nitrogen and stirred at 70° C. for 4 hours. After cooling down, the mixture was filtered over celite and the filter cake washed with ethyl acetate. The filtrate was diluted with ethyl acetate and water and partitioned. The organic layer was washed with brine, dried over sodium sulfate, filtered and the filtrate concentrated. The crude isolate was purified by silica gel chromatography (0 to 80% ethyl acetate/hexane) to give the titled compound as a white solid. $^1$H NMR (500 MHz, CDCl$_3$): δ 8.3 (d, J=2.1 Hz, 1H), 7.95 (s, 1H), 7.92 (d, J=7.7 Hz, 1H), 7.78 (d, J=2.0 Hz, 1H), 7.27 (d, J=7.9 Hz, 1H), 2.35 (s, 3H), 1.65 (s, 9H).

Step B: tert-Butyl 4-(5-chloro-6-methylpyridin-3-yl)-3-methylbenzoate

A suspension of tert-butyl 4-(5,6-dichloropyridin-3-yl)-3-methylbenzoate (Step A, 650 mg, 1.92 mmol), potassium methyltrifluoroborate (234 mg, 1.92 mmol), Cs$_2$CO$_3$ (1.88 g, 5.77 mmol), 1,1'-bis(diphenylphosphino)ferrocene-palladium(II)dichloride dichloromethane complex (157 mg, 0.192 mmol), dioxane (4 mL) and water (0.25 mL) was flushed with nitrogen and stirred at 110° C. for 2 hours. After cooling down, the mixture was filtered over celite. The filter cake was washed with ethyl acetate and further diluted with ethyl acetate and water. After separating the layers, the organic was washed with brine. The organic layer was dried over sodium sulfate, filtered and the filtrate was concentrated. The crude isolate was purified by silica gel chromatography (0 to 80% ethyl acetate/hexane) to give the titled compound as a white solid. $^1$H NMR (500 MHz, CDCl$_3$): δ 8.38 (d, J=1.9 Hz, 1H), 7.94 (s, 1H), 7.90 (d, J=8.0 Hz, 1H), 7.63 (d, J=1.8 Hz, 1H), 7.27 (d, J=7.9 Hz, 1H), 2.7 (s, 3H), 2.35 (s, 3H), 1.64 (s, 9H).

Intermediate 40

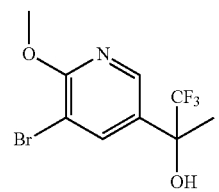 [SMILES: COc1ncc(C(C)(O)C(F)(F)F)cc1Br]

(RS)-2-(5-Bromo-6-methoxypyridin-3-yl)-1,1,1-trifluoropropan-2-ol

Step A: (RS)-1,1,1-Trifluoro-2-(6-methoxypyridin-3-yl)propan-2-ol 1.0M Tetra-butyl ammonium fluoride in THF (13.23 mL, 13.23 mmol) was added to a THF solution (20 mL) of 1-(6-methoxypyridin-3-yl)ethanone (2 g, 13.23 mmol) and (trifluoromethyl)trimethylsilane (3.76 g, 26.5 mmol) under nitrogen at 0° C. The reaction was warmed to 25° C. and stirred for 18 hours, at which time LCMS showed >95% conversion to product. The reaction was diluted with 50 mL ethyl acetate and poured into 100 mL saturated NH$_4$Cl; the organic layer was washed with 100 mL brine, dried over sodium sulfate, filtered and the filtrate concentrated. Silica gel chromatography using a linear gradient of 0-100% ethyl acetate/hexanes gave the title compound as a white solid. LCMS (M+H)$^+$: 222.0. $^1$H NMR (500 MHz, CDCl$_3$): δ 8.36 (d, J=1.9 Hz, 1H), 7.81 (dd, J=1.9 and 8.8 Hz, 1H), 6.79 (d, J=8.8 Hz, 1H), 3.97 (s, 3H), 2.80 (s, 1H), 1.80 (s, 3H).

Step B: (RS)-2-(5-Bromo-6-methoxypyridin-3-yl)-1,1,1-trifluoropropan-2-ol

Bromine (0.734 mL, 14.24 mmol) was added under nitrogen atmosphere to an acetic acid (20 mL, 349 mmol) mixture of (RS)-1,1,1-trifluoro-2-(6-methoxypyridin-3-yl)propan-2-ol (Step A, 2.1 g, 9.49 mmol) and potassium acetate (4.66 g, 47.5 mmol), which was then stirred for 30 minutes at 80° C. in oil bath. LCMS showed 30% conversion to product with a clean profile. The reaction was allowed to stir for 1.5 hours total at 80° C. and LCMS showed 40% conversion. Two additional bromine additions (0.734 mL, 14.24 mmol each) were added 30 minutes apart. The reaction was then allowed to stir at 25° C. for 48 hours. The reaction was 80% complete by LCMS. It was diluted with ethyl acetate and poured slowly into 5N NaOH (70.1 mL, 350 mmol) to neutralize the acetic acid. The organic layer was washed with brine (100 mL) and concentrated. Silica gel chromatography using a linear gradient of 0-100% ethyl acetate/hexanes gave the title compound as a pale yellow solid. LCMS (M+H)$^+$: 302.2. $^1$H NMR (CDCl$_3$, 500 MHz): δ 8.29 (d, J=1.8 Hz, 1H), 8.07 (d, J=1.8 Hz, 1H), 4.06 (s, 3H), 2.53 (s, 1H), 1.81 (s, 3H).

Scheme F

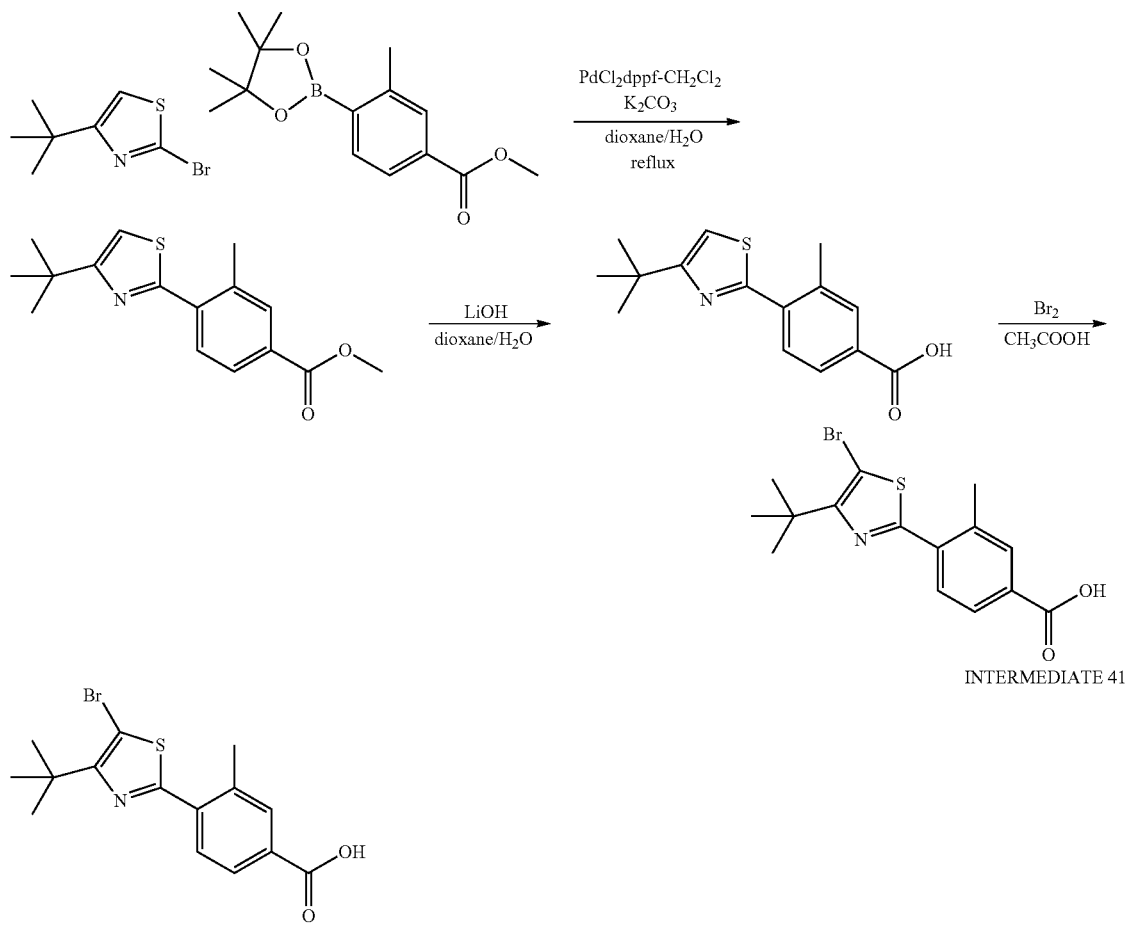

INTERMEDIATE 41

4-(5-Bromo-4-tert-butylthiazol-2-yl)-3-methylbenzoic acid

Step A: Methyl 4-(4-tert-butylthiazol-2-yl)-3-methylbenzoate

To a suspension of 2-bromo-4-(1,1-dimethylethyl)thiazole (6 g, 27.3 mmol), methyl 3-methyl-4-(4,4,5,5-tetramethyl-1,3,2-dioxaborolan-2-yl)benzoate (9.78 g, 35.4 mmol), and potassium carbonate (11.30 g, 82 mmol) in 1,4-dioxane (20 mL) and water (5 mL), was added 1,1'-bis(diphenylphosphino)ferrocene-palladium(II)dichloride dichloromethane complex (1.113 g, 1.363 mmol). It was degassed and refilled with nitrogen, and was heated to reflux for 1 hour to see complete conversion of the 2-bromothiazole, by LCMS. It was distributed between water (50 mL) and ethyl acetate (200 mL). The organic layer was collected, dried over sodium sulfate, filtered and the filtrate concentrated. The crude isolate was purified on silica gel, eluting with 30% of ethyl acetate in hexanes, to get methyl 4-(4-tert-butylthiazol-2-yl)-3-methylbenzoate as a white solid (7.3 g, 93% yield). LCMS (M+H)$^+$: 290.1. $^1$H NMR (CDCl$_3$, 500 MHz): δ 8.00 (s, 1H), 7.93 (d, J=8.5 Hz, 1H), 7.83 (d, J=8.5 Hz, 1H), 7.02 (s, 1H), 3.97 (s, 3H), 2.70 (s, 3H), 1.43 (s, 9H).

Step B: 4-(4-tert-Butylthiazol-2-yl)-3-methylbenzoic acid

Methyl 4-(4-tert-butylthiazol-2-yl)-3-methylbenzoate (Step A, 7.3 g, 25.2 mmole) was stirred with lithium hydroxide (1.5 g, 63.5 mmol) in 20 mL of 1,4-dioxane and 10 mL of water for 3 hours. It was concentrated to dryness to collect 4-(4-tert-butylthiazol-2-yl)-3-methylbenzoic acid as a white solid. This was used in the next step without any further purification. LCMS (M+H)$^+$: 276.0

Step C: 4-(5-Bromo-4-tert-butylthiazol-2-yl)-3-methylbenzoic acid 4-(4-tert-Butylthiazol-2-yl)-3-methylbenzoic acid (Step B, 7.0 g, 25.4 mmol) was dissolved in 30 mL of acetic acid, and bromine (8.1 g, 50.8 mmol) was added. The red mixture was stirred at room temperature for 20 minutes to see complete conversion by LCMS. Excess sodium bisulfite was added until the reaction mixture became colorless. The mixture was concentrated to dryness, dry-loaded to a silica gel column, and purified, eluting with 10% methanol in methylene chloride, to get 4-(5-bromo-4-tert-butylthiazol-2-yl)-3-methylbenzoic acid as a white solid (8.5 g, 94% yield over 2 steps). LCMS (M+H)$^+$: 355.9; 353.9. $^1$H NMR (CDCl$_3$, 500 MHz): 7.92 (s, 1H), 7.84 (m, 2H), 2.60 (s, 3H), 1.49 (s, 9H).

47

Scheme G

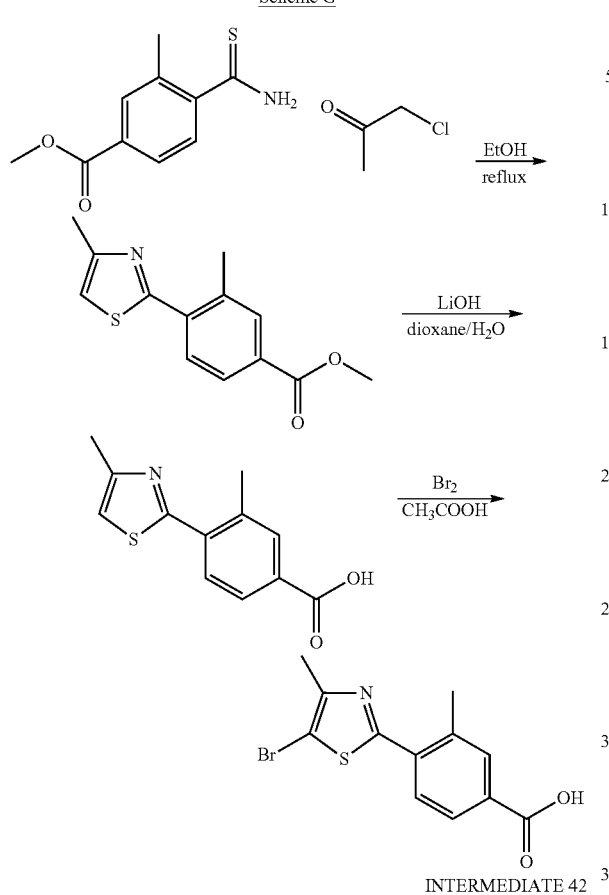

4-(5-Bromo-4-methylthiazol-2-yl)-3-methylbenzoic acid

Step A: Methyl 3-methyl-4-(4-methylthiazol-2-yl)benzoate

Methyl 4-carbamothioyl-3-methylbenzoate (8.9 g, 42.5 mmol) and chloroacetone (3.94 g, 42.5 mmol) were dissolved in ethanol (50 mL), and refluxed for 12 hours. The solvent was evaporated, and the residue was purified on a silica gel column, eluting with 20%-40% ethyl acetate in hexanes, to get methyl 3-methyl-4-(4-methylthiazol-2-yl)benzoate as white waxy solids (contains some ethyl 3-methyl-4-(4-methylthiazol-2-yl)benzoate) (7.4 g, 69% yield). An aliquot amount of the methyl and ethyl ester mixture was separated for identification purpose.

For methyl ester: LCMS (M+H)+: 248.1. $^1$H NMR (CDCl$_3$, 500 MHz): δ 8.00 (s, 1H), 7.93 (d, J=8.5 Hz, 1H), 7.82 (d, J=8.5 Hz, 1H), 7.04 (s, 1H), 3.96 (s, 3H), 2.65 (s, 3H), 2.57 (s, 3H). For ethyl ester: LCMS (M+H)+: 262.05. $^1$H NMR

48

(CDCl$_3$, 500 MHz): δ 8.00 (s, 1H), 7.94 (d, 8.0 Hz, 1H), 7.83 (d, J=8.0 Hz, 1H), 7.03 (s, 1H), 4.42 (q, 7.0 Hz, 2H), 2.66 (s, 3H), 2.57 (s, 3H), 1.44 (t, 7.0 Hz, 2H).

Step B: 3-Methyl-4-(4-methylthiazol-2-yl)benzoic acid

To a solution of methyl 3-methyl-4-(4-methylthiazol-2-yl)benzoate (Step A, 6.0 g, 22.96 mmol) in 1,4-dioxane (5 mL) was added lithium hydroxide (1.65 g, 68.9 mmol) in water (5 mL). Once the reaction was deemed complete by LCMS, it was concentrated in vacuo. The residual white solid was washed with a mixture of dichloromethane/methanol (1/1), and filtered. The filtrate was concentrated to give the title compound as a white solid which was used in the next step without further purification. LCMS (M+H)+: 234.1

Step C: 4-(5-Bromo-4-methylthiazol-2-yl)-3-methylbenzoic acid

3-Methyl-4-(4-methylthiazol-2-yl)benzoic acid (all recovered product from step A above) was dissolved in acetic acid (20 mL, 349 mmol), and bromine (1.774 mL, 34.4 mmol) was added. After sonicating for 5 minutes, LCMS showed complete conversion. Excess sodium bisulfite was added to the reaction solution until the red color disappeared. The suspension was filtered, and the filtrate was concentrated. The crude was purified on a silica gel column, eluting with 30% ethyl acetate, to give title compound as a white solid (6.2 g, 87% yield). LCMS (M+H)+: 313.9. $^1$H NMR (DMSO, 500 MHz): δ 7.90 (s, 1H), 7.85 (s, 2H), 2.56 (s, 3H), 2.40 (s, 3H).

Intermediate 43

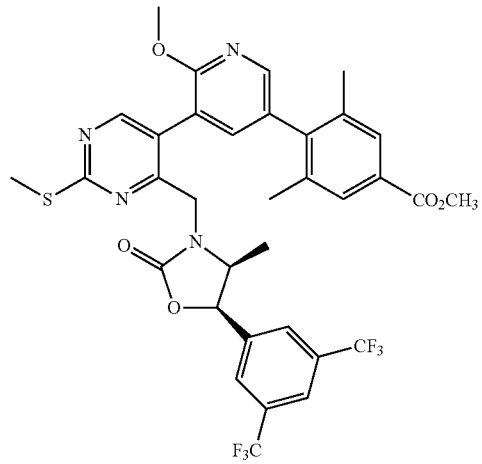 [SMILES: COC(=O)c1cc(C)c(-c2cnc(OC)c(-c3cnc(SC)nc3CN3C(=O)O[C@H](c4cc(C(F)(F)F)cc(C(F)(F)F)c4)[C@@H]3C)c2)c(C)c1]

Methyl 4-{5-[4-({(4S,5R)-5-[3,5-bis(trifluoromethyl)phenyl]-4-methyl-2-oxo-1,3-oxazolidin-3-yl}methyl)-2-(methylsulfanyl)pyrimidin-5-yl]-6-methoxypyridin-3-yl}-3,5-dimethylbenzoate (4S,5R)-5-[3,5-Bis(trifluoromethyl)phenyl]-4-methyl-3-{[2-(methylthio)-5-(4,4,5,5-tetramethyl-1,3,2-dioxaborolan-2-yl)pyrimidin-4-yl]methyl}-1,3-oxazolidin-2-one (INTERMEDIATE 21, 1.12 g, 1.940 mmol), methyl 4-(5-bromo- 6-methoxypyridin-3-yl)-3,5-dimethylbenzoate (INTERMEDIATE 33, 0.815 g, 2.328 mmol) and Pd(Ph₃P)₄ (0.224 g, 0.194 mmol) were evacuated and charged with nitrogen. Added 1,4-dioxane (9.70 mL) and 2N tribasic potassium phosphate (2.91 mL, 5.82 mmol), then stirred at 170° C. for 10 minutes in a microwave reactor. LCMS showed significant product formation. The crude was purified directly by silica gel chromatography, eluting with a gradient of 5-40% ethyl acetate/hexanes over 10 column volumes to give the title compound. ¹H NMR (CDCl₃, 500 MHz): δ 8.36 (s, 1H), 8.07 (d, 1H), 7.89 (s, 1H), 7.81 (s, 2H), 7.74 (s, 2H), 7.33 (d, 1H), 5.73 (d, 1H), 4.81 (d, 1H), 4.44 (br, 1H), 4.08 (m, 1H), δ4.01 (s, 3H), 3.93 (s, 3H), 2.62 (s, 3H), 2.16 (s, 3H), 2.14 (s, 3H), 0.75 (d, 3H).

Intermediate 44

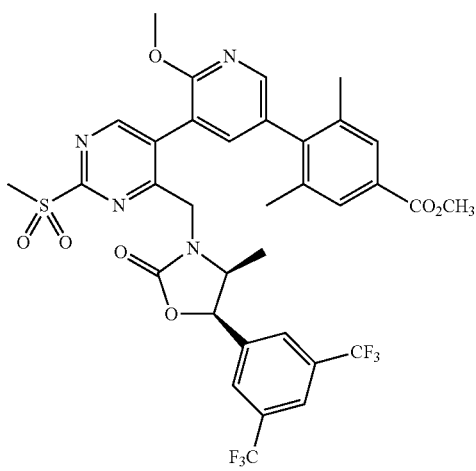 [SMILES: COC(=O)c1cc(C)c(-c2cnc(OC)c(-c3cnc(S(C)(=O)=O)nc3CN3C(=O)O[C@H](c4cc(C(F)(F)F)cc(C(F)(F)F)c4)[C@@H]3C)c2)c(C)c1]

Methyl 4-{5-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3,5-dimethylbenzoate Methyl 4-{5-[4-({(4S,5R)-5-[3,5-bis(trifluoromethyl)phenyl]-4-methyl-2-oxo-1,3-oxazolidin-3-yl}methyl)-2-(methylthio)pyrimidin-5-yl]-6-methoxypyridin-3-yl}-3,5-dimethylbenzoate (INTERMEDIATE 43, 1.05 g, 1.457 mmol) was dissolved in acetonitrile (10.2 mL). Water (4.4 mL) was added, followed by potassium peroxymonosulfate (2.24 g, 3.64 mmol). The reaction was allowed to stir 16 hours, after which it was partitioned between ethyl acetate and brine. The organic was washed a second time with brine, dried over sodium sulfate, filtered and evaporated to give the title compound, which can be used without further purification. ¹H NMR (CDCl₃, 500 MHz): δ 8.75 (s, 1H), 8.16 (d, 1H), 7.89 (s, 1H), 7.83 (s, 2H), 7.77 (s, 2H), 7.42 (d, 1H), 5.88 (d, 1H), 4.92 (d, 1H), 4.62 (br, 1H), 4.25 (d, 1H), 4.04 (s, 3H), 3.94 (s, 3H), 3.41 (s, 3H), 2.17 (d, 6H), 0.81 (d, 3H).

Intermediate 45

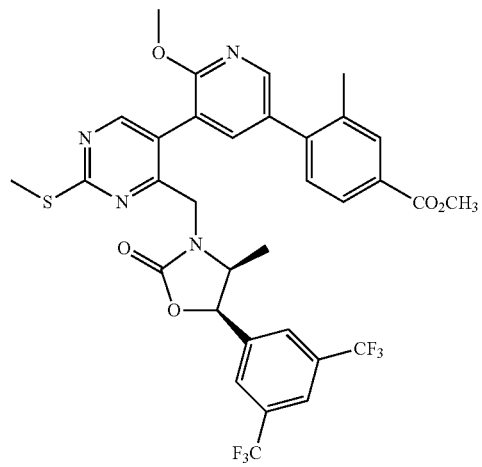 [SMILES: COC(=O)c1ccc(-c2cnc(OC)c(-c3cnc(SC)nc3CN3C(=O)O[C@H](c4cc(C(F)(F)F)cc(C(F)(F)F)c4)[C@@H]3C)c2)c(C)c1]

Methyl 4-{5-[4-({(4S,5R)-5-[3,5-bis(trifluoromethyl)phenyl]-4-methyl-2-oxo-1,3-oxazolidin-3-yl}methyl)-2-(methylsulfanyl)pyrimidin-5-yl]-6-methoxypyridin-3-yl}-3-methylbenzoate INTERMEDIATE 45 was prepared similarly to INTERMEDIATE 43 by combining INTERMEDIATE 21 and INTERMEDIATE 34 to give the title compound. ¹H NMR (CDCl₃, 500 MHz): δ 8.38 (s, 1H), 8.26 (d, 1H), 7.98 (s, 1H), 7.93 (d, 1H), 7.88 (s, 1H), 7.74 (s, 2H), 7.51 (d, 1H), 7.32 (d, 1H), 5.71 (d, 1H), 4.82 (d, 1H), 4.43 (br, 1H), 4.10 (m, 1H), 4.01 (s, 3H), 3.93 (s, 3H), 2.62 (s, 3H), 2.38 (s, 3H), 0.75 (d, 3H).

Intermediate 46

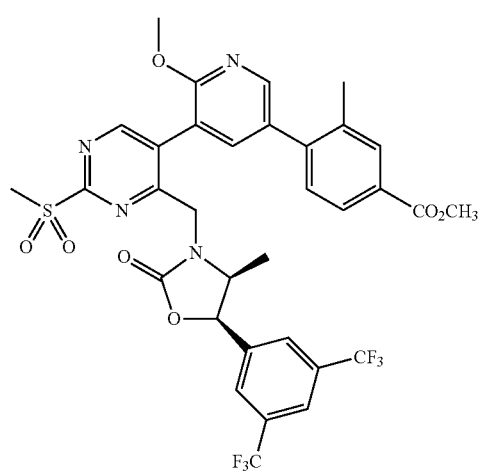 [SMILES: COC(=O)c1ccc(-c2cnc(OC)c(-c3cnc(S(C)(=O)=O)nc3CN3C(=O)O[C@H](c4cc(C(F)(F)F)cc(C(F)(F)F)c4)[C@@H]3C)c2)c(C)c1]

Methyl 4-{5-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3-methylbenzoate Using the methodology to prepare INTERMEDIATE 44, INTERMEDIATE 45 was oxidized to INTERMEDIATE 46. ¹H NMR (CDCl₃, 500 MHz): δ 8.76 (s, 1H), 8.35 (d, 1H), 8.00 (s, 1H), 7.95 (d, 1H), 7.89 (s, 1H), 7.77 (s, 2H), 7.60 (d, 1H), 7.33 (d, 1H), 5.87 (d, 1H), 4.94 (d, 1H), 4.61 (m, 1H), 4.26 (d, 1H), 4.10 (m, 1H), 4.04 (s, 3H), 3.94 (s, 3H), 3.41 (s, 3H), 2.39 (s, 3H), 0.81 (d, 3H).

Intermediate 47

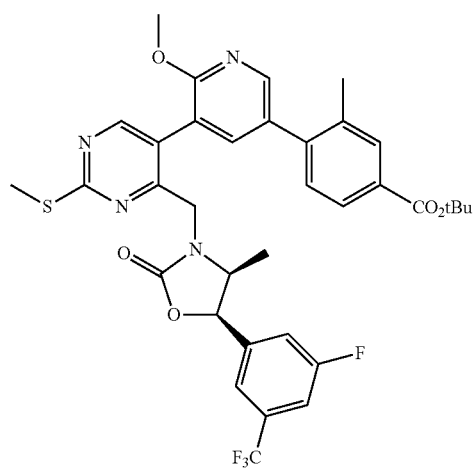 [SMILES: COc1ncc(-c2ccc(C(=O)OC(C)(C)C)cc2C)cc1-c1cnc(SC)nc1CN1C(=O)O[C@H](c2cc(F)cc(C(F)(F)F)c2)[C@@H]1C]

tert-Butyl 4-{5-[4-({(4S,5R)-5-[3-fluoro-5-(trifluoromethyl)phenyl]-4-methyl-2-oxo-1,3-oxazolidin-3-yl}methyl)-2-(methylthio)pyrimidin-5-yl]-6-methoxypyridin-3-yl}-3-methylbenzoate To a solution of (4S,5R)-3-{[5-bromo-2-(methylsulfanyl)pyrimidin-4-yl]methyl}-5-[3-fluoro-5-(trifluoromethyl)phenyl]-4-methyl-1,3-oxazolidin-2-one (INTERMEDIATE 10, 150 mg, 0.312 mmol) in THF (3.0 mL) was added {5-[4-(tert-butoxycarbonyl)-2-methylphenyl]-2-methoxypyridin-3-yl}boronic acid (INTERMEDIATE 32, 129 mg, 0.375 mmol), 1,1'-bis(di-tert-butylphosphino)ferrocene palladium dichloride (10.2 mg, 0.016 mmol), and aqueous potassium carbonate (0.468 mL, 2.0 M). The mixture was degassed, flushed with nitrogen and heated to 90° C. for 45 minutes, then allowed to stir at room temperature overnight. The reaction was diluted with ethyl acetate, washed with water, brine, dried over sodium sulfate, filtered and the filtrate concentrated. The crude product was purified by column chromatography to afford tert-butyl 4-{5-[4-({(4S,5R)-5-[3-fluoro-5-(trifluoromethyl)phenyl]-4-methyl-2-oxo-1,3-oxazolidin-3-yl}methyl)-2-(methylsulfanyl)pyrimidin-5-yl]-6-methoxypyridin-3-yl}-3-methylbenzoate (192 mg, 0.275 mmol). LCMS (M+H)⁺: 699.1

Intermediate 48

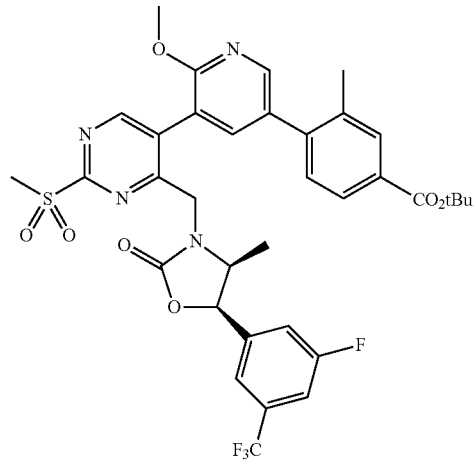 [SMILES: COc1ncc(-c2ccc(C(=O)OC(C)(C)C)cc2C)cc1-c1cnc(S(C)(=O)=O)nc1CN1C(=O)O[C@H](c2cc(F)cc(C(F)(F)F)c2)[C@@H]1C]

tert-Butyl 4-{5-[4-({(4S,5R)-5-[3-fluoro-5-(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3-methylbenzoate To a stirred solution of tert-butyl 4-{5-[4-({(4S,5R)-5-[3-fluoro-5-(trifluoromethyl)phenyl]-4-methyl-2-oxo-1,3-oxazolidin-3-yl}methyl)-2-(methylsulfanyl)pyrimidin-5-yl]-6-methoxypyridin-3-yl}-3-methylbenzoate (INTERMEDIATE 47, 192 mg, 0.275 mmol) in dichloromethane (3 mL) under nitrogen, cooled to 0° C. was added 3-chlorobenzenecarboperoxoic acid (178 mg, 0.824 mmol). The ice bath was removed and the reaction mixture was stirred for 30 minutes. The mixture was diluted with dichloromethane, washed with aqueous saturated sodium thiosulfate solution, aqueous saturated sodium bicarbonate, and brine, then dried (sodium sulfate), filtered and evaporated the filtrate under reduced pressure to yield crude tert-butyl 4-{5-[4-({(4S,5R)-5-[3-fluoro-5-(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3-methylbenzoate (195 mg, 0.266 mmol). LCMS (M+H)⁺: 731.2.

Intermediate 49

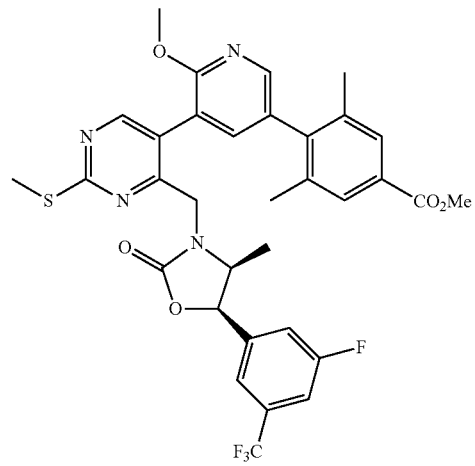 [SMILES: COC(=O)c1cc(C)c(-c2cnc(OC)c(-c3cnc(SC)nc3CN3C(=O)O[C@H](c4cc(F)cc(C(F)(F)F)c4)[C@@H]3C)c2)c(C)c1]

Methyl 4-{5-[4-({(4S,5R)-5-[3-fluoro-5-(trifluoromethyl)phenyl]-4-methyl-2-oxo-1,3-oxazolidin-3-yl}methyl)-2-(methylsulfanyl)pyrimidin-5-yl]-6-methoxypyridin-3-yl}-3,5-dimethylbenzoate A mixture of (4S,5R)-3-{[5-(5-chloro-2-methoxypyridin-3-yl)-2-(methylsulfanyl)pyrimidin-4-yl]methyl}-5-[3-fluoro-5-(trifluoromethyl)phenyl]-4-methyl-1,3-oxazolidin-2-one (INTERMEDIATE 18, 211 mg, 0.389 mmol), bis(pinacolato)diboron (296 mg, 1.17 mmol), and potassium acetate (114 mg, 1.17 mmol) in N,N-dimethylacetamide (2.0 mL) was degassed three times with nitrogen gas before the addition of (2-dicyclohexylphosphino-2',4',6'-triisopropyl-1,1'-biphenyl)[2-(2-aminoethyl)phenyl)]palladium(II) chloride (XPHOS Biphenyl Precatalyst) (15.5 mg, 0.019 mmol). The system was degassed three times and was then heated to 130° C. for 24 hours. LC/MS analysis indicated complete conversion to the product, but almost exclusively as the boronic acid. For this reason the crude reaction mixture was taken directly into the next step. Accordingly, methyl 4-bromo-3,5-dimethylbenzoate (142 mg, 0.584 mmol), (1,1'-bis(di-tert-butylphosphino)ferrocene palladium dichloride (24.5 mg, 0.039 mmol), and aqueous potassium carbonate (0.389 mL, 2.0 M) were added. The mixture was degassed, flushed with nitrogen and heated to 100° C. for 45 minutes. The reaction was diluted with ethyl acetate, washed with water, brine, dried over sodium sulfate, filtered and concentrated. The crude product was purified by column chromatography to afford methyl 4-{5-[4-({(4S,5R)-5-[3-fluoro-5-(trifluoromethyl)phenyl]-4-methyl-2-oxo-1,3-oxazolidin-3-yl}methyl)-2-(methylsulfanyl)pyrimidin-5-yl]-6-methoxypyridin-3-yl}-3,5-dimethylbenzoate (158 mg, 0.236 mmol). LCMS (M+H)$^+$: 671.1

Intermediate 50

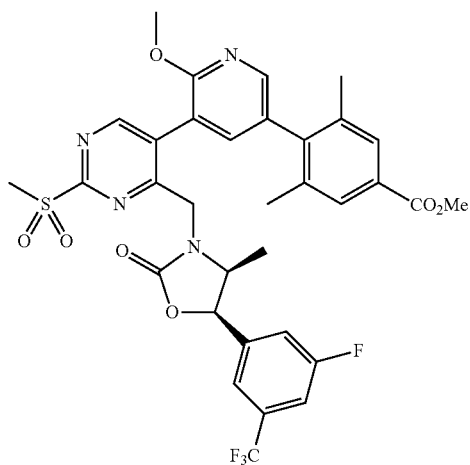 [SMILES: COC(=O)c1cc(C)c(-c2cnc(OC)c(-c3cnc(S(C)(=O)=O)nc3CN3C(=O)O[C@H](c4cc(F)cc(C(F)(F)F)c4)[C@@H]3C)c2)c(C)c1]

Methyl 4-{5-[4-({(4S,5R)-5-[3-fluoro-5-(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3,5-dimethylbenzoate To a stirred solution of methyl 4-{5-[4-({(4S,5R)-5-[3-fluoro-5-(trifluoromethyl)phenyl]-4-methyl-2-oxo-1,3-oxazolidin-3-yl}methyl)-2-(methylsulfanyl)pyrimidin-5-yl]-6-methoxypyridin-3-yl}-3,5-dimethylbenzoate (INTERMEDIATE 49, 157 mg, 0.234 mmol) in dichloromethane (3 mL) under nitrogen, cooled to 0° C. was added 3-chlorobenzenecarboperoxoic acid (157 mg, 0.702 mmol). The ice bath was removed and the reaction mixture was stirred for 30 minutes. The mixture was diluted with dichloromethane, washed with aqueous saturated sodium thiosulfate solution, aqueous saturated sodium bicarbonate, and brine, then dried (sodium sulfate), filtered and evaporated under reduced pressure to yield crude methyl 4-{5-[4-({(4S,5R)-5-[3-fluoro-5-(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3,5-dimethylbenzoate (161 mg, 0.229 mmol). LCMS (M+H)$^+$: 703.1

Intermediate 51

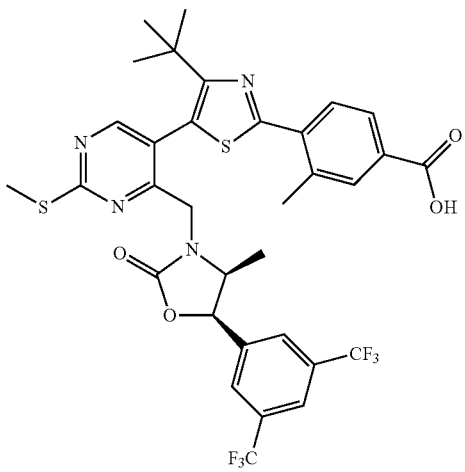 [SMILES: CSc1ncc(-c2sc(-c3ccc(C(=O)O)cc3C)nc2C(C)(C)C)c(CN2C(=O)O[C@H](c3cc(C(F)(F)F)cc(C(F)(F)F)c3)[C@@H]2C)n1]

4-{5-[4-({(4S,5R)-5-[3,5-Bis(trifluoromethyl)phenyl]-4-methyl-2-oxo-1,3-oxazolidin-3-yl}methyl)-2-(methylsulfanyl)pyrimidin-5-yl]-4-tert-butyl-1,3-thiazol-2-yl}-3-methylbenzoic acid To a solution of (4S,5R)-5-[3,5-bis(trifluoromethyl)phenyl]-4-methyl-3-{[2-(methylsulfanyl)-5-(4,4,5,5-tetramethyl-1,3,2-dioxaborolan-2-yl)pyrimidin-4-yl]methyl}-1,3-oxazolidin-2-one (INTERMEDIATE 21, 2.0 g, 3.46 m mol), 4-(5-bromo-4-tert-butylthiazol-2-yl)-3-methylbenzoic acid (INTERMEDIATE 41, 1.350 g, 3.81 mmol), potassium phosphate (8.18 mL, 1.27 M, 10.39 m mol) in THF (5 mL) and water (5.00 mL) was added tetrakis(triphenylphosphine)palladium(0) (0.400 g, 0.346 mmol). It was degassed, and refilled with nitrogen. The reaction mixture was heated to reflux for 2 hours to see complete conversion by LCMS. It was distributed between 100 mL of water and 300 mL of ethyl acetate. The organic layer was collected, dried over sodium sulfate, filtered and the filtrate concentrated. The crude isolate was purified by silica gel chromatography, eluting with 30% ethyl acetate in hexanes to give the title compound as white solid (225 mg, 9.0% yield). LCMS (M+H)$^+$: 725.0

Intermediate 52

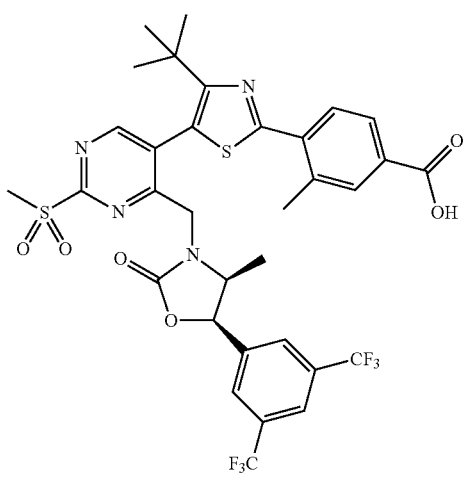 [SMILES: Cc1cc(C(=O)O)ccc1-c1nc(C(C)(C)C)c(-c2cnc(S(C)(=O)=O)nc2CN2C(=O)O[C@H](c3cc(C(F)(F)F)cc(C(F)(F)F)c3)[C@@H]2C)s1]

4-{5-[4-({(4S,5R)-5-[3,5-Bis(trifluoromethyl)phenyl]-4-methyl-2-oxo-1,3-oxazolidin-3-yl}methyl)-2-(methylsulfonyl)pyrimidin-5-yl]-4-tert-butyl-1,3-thiazol-2-yl}-3-methylbenzoic acid 4-{5-[4-({(4S,5R)-5-[3,5-Bis(trifluoromethyl)phenyl]-4-methyl-2-oxo-1,3-oxazolidin-3-yl}methyl)-2-(methylsulfanyl)pyrimidin-5-yl]-4-tert-butyl-1,3-thiazol-2-yl}-3-methylbenzoic acid (INTERMEDIATE 51, 225 mg, 0.31 mmol) was dissolved in 10 mL CH₃CN and 10 mL of water. Potassium peroxymonosulfate (5.1 g, 8.31 mmol) was added, and it was stirred at 60° C. for 2 hours. Then, it was worked up with water (100 mL) and t-butyl methyl ether (200 mL). The organic layer was dried over sodium sulfate, filtered and the filtrate concentrated. The crude isolate was purified by silica gel chromatography, eluting with 60% ethyl acetate in hexanes to give the title compound as a slightly yellow solid (226 mg, 96% yield). LCMS (M+H)⁺: 757.1 ¹H NMR (DMSO, 500 MHz): δ 9.24 (s, 1H), 8.15 (s, 1H), 8.03 (s, 2H), 7.96 (s, 1H), 7.90 (s, 2H), 6.06 (m, 1H), 4.48 (m, 1H), 3.52 (s, 3H), 2.69 (s, 3H), 1.26 (s, 9H), 0.72 (d, J=6.0 Hz, 3H).

Intermediate 53

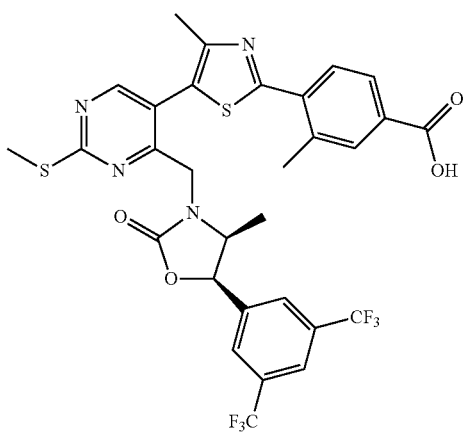 [SMILES: CSc1ncc(-c2sc(-c3ccc(C(=O)O)cc3C)nc2C)c(CN2C(=O)O[C@H](c3cc(C(F)(F)F)cc(C(F)(F)F)c3)[C@@H]2C)n1]

4-{5-[4-({(4S,5R)-5-[3,5-Bis(trifluoromethyl)phenyl]-4-methyl-2-oxo-1,3-oxazolidin-3-yl}methyl)-2-(methylthio)pyrimidin-5-yl]-4-methyl-1,3-thiazol-2-yl}-3-methylbenzoic acid To a solution of (4S,5R)-5-[3,5-bis(trifluoromethyl)phenyl]-4-methyl-3-{[2-(methylsulfanyl)-5-(4,4,5,5-tetramethyl-1,3,2-dioxaborolan-2-yl)pyrimidin-4-yl]methyl}-1,3-oxazolidin-2-one (INTERMEDIATE 21, 2.0 g, 3.46 mmol), 4-(5-bromo-4-methylthiazol-2-yl)-3-methylbenzoic acid (INTERMEDIATE 42, 1.190 g, 3.81 mmol), potassium phosphate (2.2 g, 10.39 mmol) in THF (5 mL) and water (5 mL) was added tetrakis(triphenylphosphine)palladium(0) (0.400 g, 0.346 mmol). It was degassed, and refilled with nitrogen. The reaction mixture was heated to reflux for 2 hours to see complete conversion by LCMS. It was distributed between 100 mL of water and 300 mL of ethyl acetate. The organic layer was dried over sodium sulfate, filtered and the filtrate concentrated. The crude was purified on a silica gel column, eluting with 30% ethyl acetate in hexanes to give the title compound as white solid (2.2 g, 93% yield). LCMS (M+H)⁺: 683.0

Intermediate 54

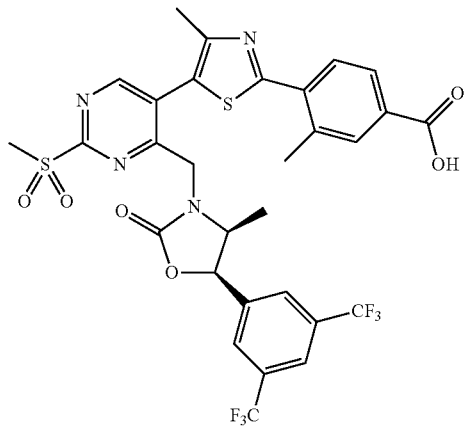 [SMILES: Cc1cc(C(=O)O)ccc1-c1nc(C)c(-c2cnc(S(C)(=O)=O)nc2CN2C(=O)O[C@H](c3cc(C(F)(F)F)cc(C(F)(F)F)c3)[C@@H]2C)s1]

4-{5-[4-({(4S,5R)-5-[3,5-Bis(trifluoromethyl)phenyl]-4-methyl-2-oxo-1,3-oxazolidin-3-yl}methyl)-2-(methylsulfonyl)pyrimidin-5-yl]-4-methyl-1,3-thiazol-2-yl}-3-methylbenzoic acid 4-{5-[4-({(4S,5R)-5-[3,5-Bis(trifluoromethyl)phenyl]-4-methyl-2-oxo-1,3-oxazolidin-3-yl}methyl)-2-(methylthio)pyrimidin-5-yl]-4-methyl-1,3-thiazol-2-yl}-3-methylbenzoic acid (INTERMEDIATE 53, 2.2 g, 3.22 mmol), was dissolved in 10 mL of THF and 10 mL of water. Potassium peroxymonosulfate (5.11 g, 8.31 mmol) was added, and it was stirred at 60° C. for 2 hours. Then, it was worked up with water (100 mL) and t-butyl methyl ether (200 mL). The organic layer was concentrated and purified on a silica gel column, eluting with 60% ethyl acetate in hexanes to give the title compound as a slightly yellow solid. LCMS (M+1): 715.0 ¹H NMR (CDCl₃, 500 MHz): δ 8.93 (s, 1H), 8.93 (s, 1H), 8.10 (s, 1H), 8.03 (d, 8.5 Hz, 1H), 7.93 (m, 2H), 7.82 (s, 2H), 6.00 (d, 8.5 Hz, 1H), 5.08 (d, 16.5 Hz, 1H), 4.67 (m, 1H), 4.31 (d, 16.6 Hz, 1H), 3.46 (s, 3H), 2.75 (s, 3H), 2.50 (s, 3H), 0.86 (d, 6.5 Hz, 3H).

Example 1

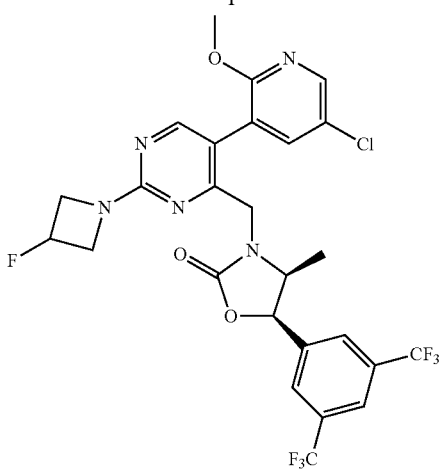

(4S,5R)-5-[3,5-Bis(trifluoromethyl)phenyl]-3-{[5-(5-chloro-2-methoxypyridin-3-yl)-2-(3-fluoroazetidin-1-yl)pyrimidin-4-yl]methyl}-4-methyl-1,3-oxazolidin-2-one (4S,5R)-5-[3,5-Bis(trifluoromethyl)phenyl]-3-{[5-bromo-2-(3-fluoroazetidin-1-yl)pyrimidin-4-yl]methyl}-4-methyl-1,3-oxazolidin-2-one (INTERMEDIATE 14, 425 mg, 0.763 mmol), 5-chloro-2-methoxypyridin-3-ylboronic acid (214 mg, 1.144 mmol), 1,1'-bis(di-tert-butylphosphino) ferrocene palladium dichloride (49.7 mg, 0.076 mmol) and $K_2CO_3$ (316 mg, 2.288 mmol) were added to a reaction vial that was evacuated and charged with nitrogen three times. The solid reactants were then mixed with THF (4 mL) and water (400 μl), degassed and refilled with nitrogen, capped and heated for 30 minutes at 125° C. in a BIOTAGE microwave reactor, after which LCMS showed complete conversion to product. The reaction was diluted with 5 mL acetonitrile and filtered through a 1 g RP $C_{18}$ silica cartridge, eluting with 15 mL acetonitrile until filtrate was colorless. The filtrate was concentrated prior to RP Prep purification on a X-Bridge 30×300 mm RP column. The sample was loaded in 7:3:1 $CH_3CN$/water/DMSO (5 mL) and eluted with a 10-100% acetonitrile/water (0.1% $NH_4OH$) linear gradient over 20 minutes. The product of interest eluted in 80% portion of above gradient. Pure fractions (rich cut; impure discarded) were concentrated and lyophilized to give a white solid. LCMS (M+H)+: 619.1. $^1$H NMR ($CDCl_3$, 500 MHz): δ 8.24 (s, 1H) 8.16 (s, 1H) 7.93 (s, 1H) 7.77 (s, 2H) 7.53 (s, 1H) 5.73 (m, 1H) 5.57 (m, 0.5H) 5.46 (m, 0.5H), 4.70 (d, J=17.4 Hz, 1H), 4.48 (m, 4H), 4.06 (d, J=17.5 Hz, 1H), 3.97 (s, 3H), 0.78 (bs, 3H). Rotomers gave broad signals. SPA $IC_{50}$: 38 nM.

Example 2

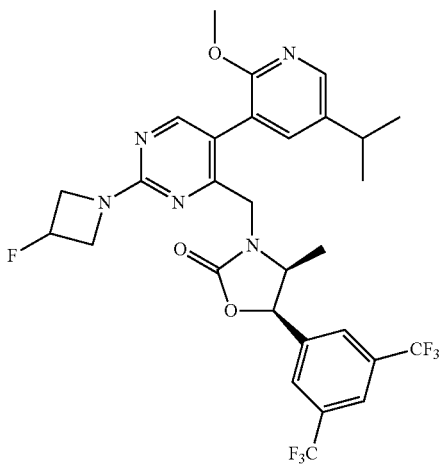 [SMILES: COc1ncc(C(C)C)cc1-c1cnc(N2CC(F)C2)nc1CN1C(=O)O[C@H](c2cc(C(F)(F)F)cc(C(F)(F)F)c2)[C@@H]1C]

(4S,5R)-5-[3,5-Bis(trifluoromethyl)phenyl]-3-{[2-(3-fluoroazetidin-1-yl)-5-(5-isopropyl-2-methoxypyridin-3-yl)pyrimidin-4-yl]methyl}-4-methyl-1,3-oxazolidin-2-one (4S,5R)-5-[3,5-Bis(trifluoromethyl)phenyl]-3-{[5-bromo-2-(3-fluoroazetidin-1-yl)pyrimidin-4-yl]methyl}-4-methyl-1,3-oxazolidin-2-one (INTERMEDIATE 14, 1.2 g, 2.153 mmol), 5-isopropyl-2-methoxypyridin-3-ylboronic acid (0.716 g, 2.58 mmol), 1,1'-Bis(di-tert-butylphosphino) ferrocene palladium dichloride (211 mg, 0.323 mmol) and $K_2CO_3$ (893 mg, 6.46 mmol) were added to a reaction vial that was evacuated and charged with nitrogen three times. The solid reactants were then mixed with THF (15 mL) and water (3 mL), degassed and refilled with nitrogen, capped and heated for 1 hour at 50° C. in a BIOTAGE microwave reactor, after which LCMS showed complete conversion to product. The reaction was diluted with 50 mL ethyl acetate and poured into 100 mL sat'd $NH_4Cl$ soln. The ethyl acetate layer was washed with brine (100 mL) filtered through a 20 g plug of sodium sulfate, eluting with 50 mL ethyl acetate. The filtrate was concentrated prior to RP Prep purification on a X-Bridge 30×300 mm RP column. After loading the column was eluted with a 10-100% acetonitrile/water (0.1% $NH_4OH$) linear gradient over 20 minutes. The product of interest eluted in 80% portion of above gradient. Pure fractions were concentrated and lyophilized to give a white solid. LCMS (M+H)+: 628.5 $^1$H NMR ($CDCl_3$, 500 MHz): δ 8.16 (s, 1H), 8.11 (d, J=2.2 Hz, 1H), 7.91 (s, 1H), 7.76 (s, 2H), 7.36 (d, J=2.2 Hz, 1H), 5.68 (d, J=8.6 Hz, 1H), 5.54 (m, 0.5H) 5.43 (m, 0.5H), 4.70 (d, J=17.2 Hz, 1H), 4.51 (m, 2H), 4.33 (m, 2H), 4.02 (d, J=17.4 Hz, 1H), 3.94 (s, 3H), 2.96 (m, 1H), 1.30 (d, J=6.9 Hz, 6H), 0.74 (d, J=6.7 Hz, 3H). SPA $IC_{50}$: 11 nM.

Example 3

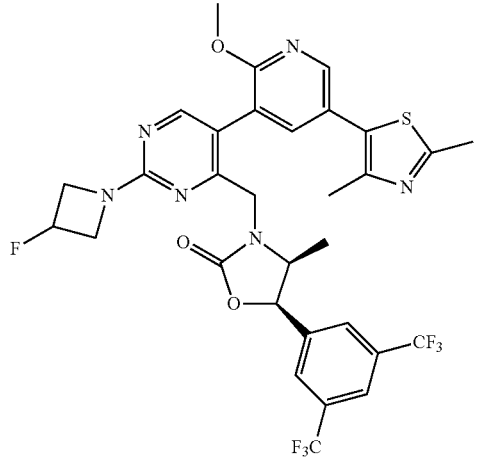 [SMILES: COc1ncc(-c2sc(C)nc2C)cc1-c1cnc(N2CC(F)C2)nc1CN1C(=O)O[C@H](c2cc(C(F)(F)F)cc(C(F)(F)F)c2)[C@@H]1C]

(4S,5R)-5-[3,5-Bis(trifluoromethyl)phenyl]-3-({5-[5-(2,4-dimethyl-1,3-thiazol-5-yl)-2-methoxypyridin-3-yl]-2-(3-fluoroazetidin-1-yl)pyrimidin-4-yl}methyl)-4-methyl-1,3-oxazolidin-2-one (4S,5R)-5-[3,5-Bis(trifluoromethyl)phenyl]-3-{[5-(5-chloro-2-methoxypyridin-3-yl)-2-(3-fluoroazetidin-1-yl)pyrimidin-4-yl]methyl}-4-methyl-1,3-oxazolidin-2-one (EXAMPLE 1, 100 mg, 0.161 mmol), 2,4-dimethyl-5-(4,4,5,5-tetramethyl-1,3,2-dioxaborolan-2-yl)-1,3-thiazole (38.6 mg, 0.161 mmol) and $K_2CO_3$ (66.9 mg, 0.484 mmol) were mixed with 1.5 mL of 4/1 dioxane/water. The mixture was evacuated and charged with nitrogen three times, then {2-[2-(amino-κN)ethyl]phenyl-κ$C^1$}(chloro)[di-tert-butyl(2',4',6'-triisopropylbiphenyl-2-yl)phosphine]palladium (tert-Butyl X-Phos Precatalyst) (8.3 mg, 0.016 mmol) was added. The reaction was sealed and then heated for 25 minutes at 130° C. in a microwave reactor. The reaction was diluted with 5 mL acetonitrile and filtered through a 1 g RP $C_{18}$ silica cartridge, eluting with 15 mL acetonitrile until the filtrate was colorless. The filtrate was concentrated prior to RP Prep purification on a X-Bridge 21.2×150 mm RP column. The sample was loaded in 7:3:1 CH$_3$CN/water/DMSO (5 mL), then eluted with 10-100% acetonitrile/water (0.1% NH$_4$OH) linear gradient over 20 minutes. The product of interest eluted in 80% portion of above gradient. Pure fractions (rich cut; impure discarded) were concentrated and lyophilized to give 10 mg product. LCMS (M+H)$^+$: 697.4. $^1$H NMR (CDCl$_3$, 500 MHz): δ 8.33 (d, J=2.3 Hz, 1H), 8.23 (s, 1H), 7.94 (s, 1H), 7.80 (s, 2H), 7.55 (d, J=2.1 Hz, 1H), 5.71 (d, J=8.5 Hz, 1H), 5.58 (m, 0.5H) 5.47 (m, 0.5H), 4.78 (d, J=17.1 Hz, 1H), 4.54 (m, 2H), 4.37 (m, 3H), 4.06 (d, J=18.4 Hz, 1H), 4.04 (s, 3H), 2.75 (s, 3H), 2.51 (s, 3H), 0.79 (d, J=6.5 Hz, 3H). RTA IC$_{50}$: 3 nM The following compounds (Table 3) were synthesized using methods analogous to those described for EXAMPLE 3 from commercially available boronic acids, boronate esters, or potassium trifluoroborate salts combined with EXAMPLE 1 in a Suzuki type coupling.

TABLE 3

| Example | Molecular structure | LCMS (M + H)$^+$ | CETP Inhibition |
|---|---|---|---|
| 4 | 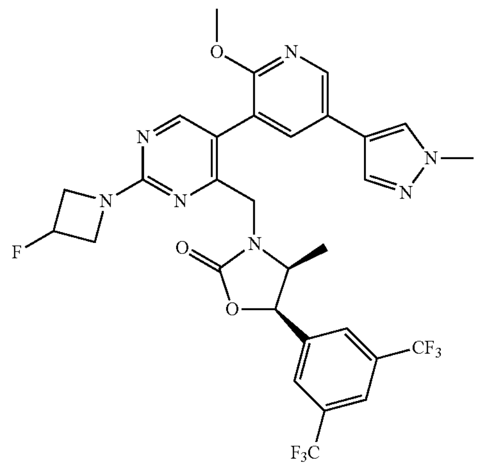 [SMILES: COc1ncc(-c2cnn(C)c2)cc1-c1cnc(N2CC(F)C2)nc1CN1C(=O)O[C@H](c2cc(C(F)(F)F)cc(C(F)(F)F)c2)[C@@H]1C] | 666.5 | SPA IC$_{50}$: 137 nM |
| 5 | 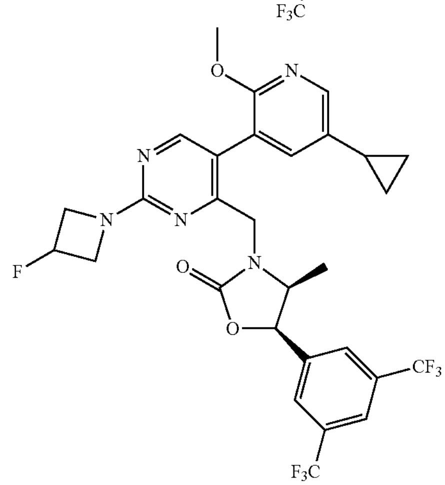 | 626.4 | SPA IC$_{50}$: 34 nM |
| 6 | 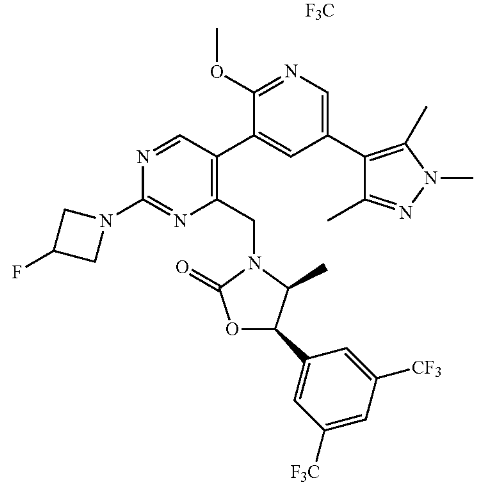 | 694.4 | RTA IC$_{50}$: 3 nM |

TABLE 3-continued

| Example | Molecular structure | LCMS (M + H)+ | CETP Inhibition |
|---|---|---|---|
| 7 | 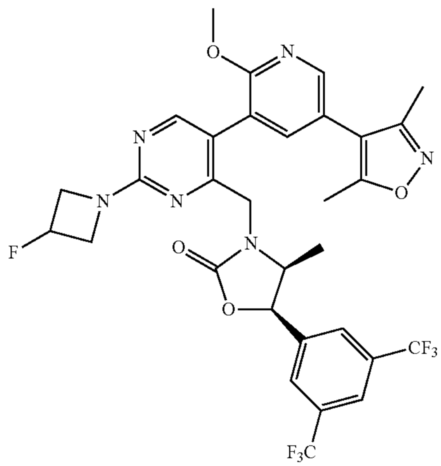 [SMILES: COc1ncc(-c2c(C)noc2C)cc1-c1cnc(N2CC(F)C2)nc1CN1C(=O)O[C@H](c2cc(C(F)(F)F)cc(C(F)(F)F)c2)[C@@H]1C] | 681.5 | RTA IC$_{50}$: 3 nM |
| 8 | 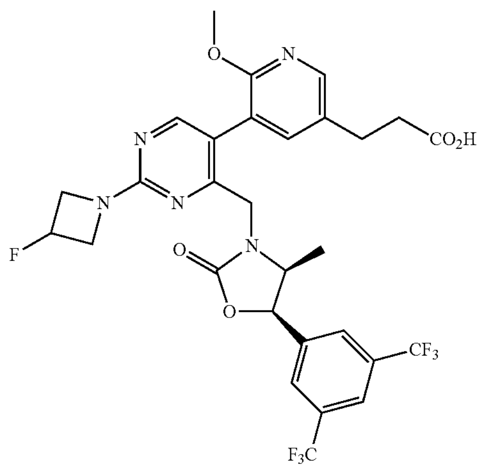 [SMILES: COc1ncc(CCC(=O)O)cc1-c1cnc(N2CC(F)C2)nc1CN1C(=O)O[C@H](c2cc(C(F)(F)F)cc(C(F)(F)F)c2)[C@@H]1C] | 658.5 | RTA IC$_{50}$: 92 nM |

Example 9

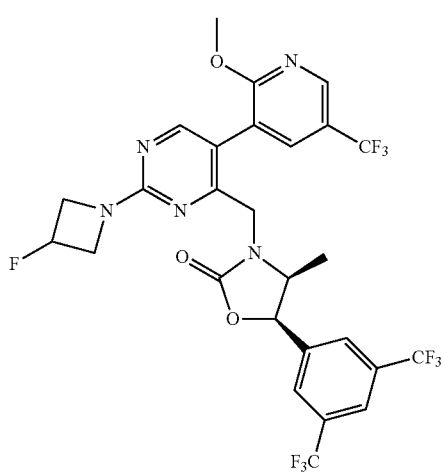 [SMILES: COc1ncc(C(F)(F)F)cc1-c1cnc(N2CC(F)C2)nc1CN1C(=O)O[C@H](c2cc(C(F)(F)F)cc(C(F)(F)F)c2)[C@@H]1C]

(4S,5R)-5-[3,5-Bis(trifluoromethyl)phenyl]-3-({2-(3-fluoroazetidin-1-yl)-5-[2-methoxy-5-(trifluoromethyl)pyridin-3-yl]pyrimidin-4-yl}methyl)-4-methyl-1,3-oxazolidin-2-one THF (1.5 mL) and water (0.3 mL) was added to a mixture of (4S,5R)-5-[3,5-bis(trifluoromethyl)phenyl]-3-{[5-bromo-2-(3-fluoroazetidin-1-yl)pyrimidin-4-yl]methyl}-4-methyl-1,3-oxazolidin-2-one (INTERMEDIATE 14, 150 mg, 0.269 mmol), 5-trifluoromethoxy-2-methoxypyridin-3-ylboronic acid (114 mg, 0.377 mmol), 1,1'-bis(di-tert-butylphosphino) ferrocene palladium dichloride (35.1 mg, 0.054 mmol) and K$_2$CO$_3$ (112 mg, 0.808 mmol). The reaction was placed under vacuum, purged with nitrogen and capped for the BIOTAGE microwave reactor. The reaction was heated for 15 minutes at 90° C., at which time LCMS showed complete consumption of starting material. The reaction was diluted with 3 mL acetonitrile and filtered through a 1 g RP C$_{18}$ silica cartridge, eluting with 10 mL acetonitrile until filtrate was colorless. The filtrate was concentrated prior to RP Prep purification under the following conditions: X-Bridge 21.2×150 mm RP column, sample loaded 7:3:1 CH$_3$CN/water/DMSO (5 mL), employed a 10-100% acetonitrile/water (0.1% NH$_4$OH) linear gradient at 15 mL/minutes over 20 minutes. The product of interest eluted in 80% portion of above gradient. Pure fractions were lyophilized to give product as a white solid. LCMS (M+H)$^+$: 654.4. $^1$H NMR (CDCl$_3$, 500 MHz): δ 8.54 (br, 1H), 8.16 (s, 1H), 7.91 (br, 1H), 7.75 (br, 2H), 7.71 (br, 1H), 5.67 (d, J=8.5 Hz, 1H), 5.55 (m, 0.5H) 5.43 (m, 0.5H), 4.71 (d, J=17.2 Hz, 1H), 4.51 (m, 2H), 4.34 (m, 3H), 4.04 (s, 3H), 3.95 (d, J=17.3 Hz, 1H), 0.75 (d, J=6.7 Hz, 3H). RTA IC$_{50}$: 14 nM.

The following compound was synthesized using methods analogous to those described for EXAMPLE 9 from INTERMEDIATE 14 and the requisite boronic acid/boronate ester.

| Example | Molecular structure | LCMS (M + H)$^+$ | CETP Inhibition |
|---------|---------------------|------------------|-----------------|
| 10      | 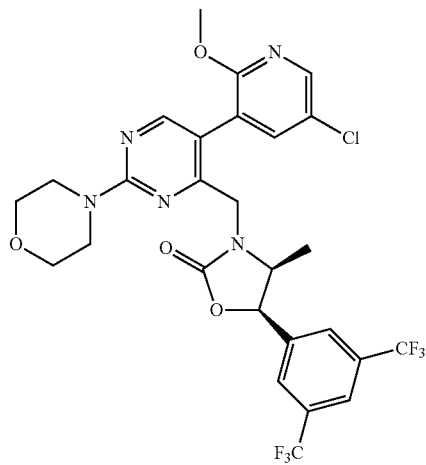 [SMILES: COc1ncc(Cl)cc1-c1cnc(N2CCOCC2)nc1CN1C(=O)O[C@H](c2cc(C(F)(F)F)cc(C(F)(F)F)c2)[C@@H]1C] | 668.3           | RTA IC$_{50}$: 12 nM |

Example 11

(4S,5R)-5-[3,5-Bis(trifluoromethyl)phenyl]-3-{[5-(5-chloro-2-methoxypyridin-3-yl)-2-(morpholin-4-yl)pyrimidin-4-yl]methyl}-4-methyl-1,3-oxazolidin-2-one Step A (4S,5R)-5-[3,5-Bis(trifluoromethyl)phenyl]-3-{[5-(5-chloro-2-methoxypyridin-3-yl)-2-(methylsulfonyl)pyrimidin-4-yl]methyl}-4-methyl-1,3-oxazolidin-2-one Potassium peroxymonosulfate (3.98 g, 6.48 mmol) was added to an acetonitrile (17 mL)/water (7 mL) suspension of (4S,5R)-5-[3,5-bis(trifluoromethyl)phenyl]-3-{[5-(5-chloro-2-methoxypyridin-3-yl)-2-(methylthio)pyrimidin-4-yl]methyl}-4-methyl-1,3-oxazolidin-2-one (INTERMEDIATE 16, 1.6 g, 2.70 mmol). This was then stirred for 30 minutes at 45° C. LCMS showed complete conversion to product. The reaction was diluted with methyl t-butyl ether (50 mL) and poured into water (100 mL). The organic layer was washed with 100 mL of 10% NaHSO$_3$ and twice with 100 mL of aqueous NaCl. It was then dried over sodium sulfate, filtered and the filtrate concentrated to give the titled compound as a white foam, which can be used without further purification. LCMS (M+H)$^+$: 625.3

Step B (4S,5R)-5-[3,5-Bis(trifluoromethyl)phenyl]-3-{[5-(5-chloro-2-methoxypyridin-3-yl)-2-(morpholin-4-yl)pyrimidin-4-yl]methyl}-4-methyl-1,3-oxazolidin-2-one Morpholine (0.217 mL, 2.488 mmol) was added to a THF (1 mL) solution of (4S,5R)-5-[3,5-bis(trifluoromethyl)phenyl]-3-{[5-(5-chloro-2-methoxypyridin-3-yl)-2-(methylsulfonyl)pyrimidin-4-yl]methyl}-4-methyl-1,3-oxazolidin-2-one (Step A, 311 mg, 0.498 mmol). This was then stirred for 30 minutes at 120° C. in a microwave reactor. LCMS showed >90% conversion to product. The reaction was concentrated on rotary evaporator. The crude isolate was purified by silica gel chromatography, eluting with a 0-50% isopropyl acetate/hexanes linear gradient followed by isocratic elution with 50% isopropyl acetate/hexanes for 10 minutes to give the titled compound as a white foam. LCMS (M+H)$^+$: 632.3. $^1$H NMR (CDCl$_3$, 500 MHz): δ 8.19 (d, J=2.5 Hz, 1H), 8.16 (s, 1H), 7.91 (s, 1H), 7.75 (s, 2H), 7.48 (d, J=2.5 Hz, 1H), 5.66 (d, J=8.5 Hz, 1H), 4.72 (d, J=17.1 Hz, 1H), 4.31 (m, 1H), 3.96 (s, 3H), 3.89 (m, 4H), 3.83 (m, 4H), 0.73 (d, J=6.5 Hz, 3H). SPA IC$_{50}$: 671 nM.

Example 12

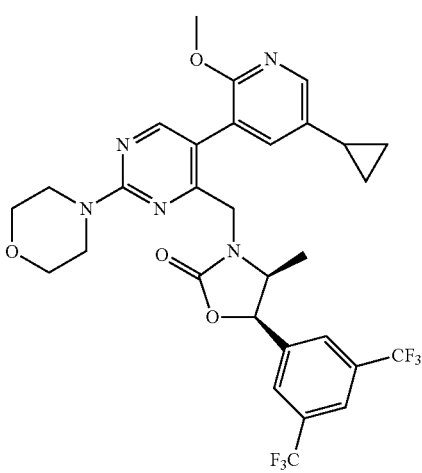 [SMILES: COc1ncc(C2CC2)cc1-c1cnc(N2CCOCC2)nc1CN1C(=O)O[C@H](c2cc(C(F)(F)F)cc(C(F)(F)F)c2)[C@@H]1C]

(4S,5R)-5-(3,5-Bis(trifluoromethyl)phenyl)-3-((5-(5-cyclopropyl-2-methoxypyridin-3-yl)-2-morpholinopyrimidin-4-yl)methyl)-4-methyloxazolidin-2-one Bis(di-tert-butyl(4-dimethylaminophenyl)phosphine) dichloropalladium(II) (11.20 mg, 0.016 mmol) was added to a degassed dioxane (700 µl)/Water (100 µl) solution of (4S,5R)-5-[3,5-bis(trifluoromethyl)phenyl]-3-{[5-(5-chloro-2-methoxypyridin-3-yl)-2-(morpholin-4-yl)pyrimidin-4-yl]methyl}-4-methyl-1,3-oxazolidin-2-one (EXAMPLE 11, 100 mg, 0.158 mmol), potassium cyclopropyltrifluoroborate (46.8 mg, 0.316 mmol) and $K_2CO_3$ (65.6 mg, 0.475 mmol). After further degassing with $N_2$ and vacuum for 3 cycles, the reaction was capped and stirred for 30 minutes at 130° C. in a Biotage microwave reactor. LCMS showed >80% conversion to product. The reaction was diluted with 5 mL acetonitrile and filtered through a 1 g RP C18 silica cartridge, eluting with 15 mL acetonitrile until the filtrate was colorless. The filtrate was concentrated and the crude purified under the following conditions: X-Bridge 21.2×150 mm RP column, sample loaded in 7:3:1 $CH_3CN$/water/DMSO (5 mL) with the column eluted using a 10-100% acetonitrile/water (0.1% $NH_4OH$) linear gradient at 15 mL/minute over 20 minutes to give the product as a white solid after lyophilization of the purified fractions. LCMS (M+H)$^+$: 638.5. $^1$H NMR (500 MHz, $CDCl_3$): δ 8.23 (br, 1H), 8.12 (br, 1H), 7.93 (br, 1H), 7.75 (br, 2H), 7.24 (br, 1H), 5.68 (m, 2H), 4.72 (d, J=17.6 Hz, 1H), 4.13 (d, J=17.6 Hz, 1H), 4.07 (m, 4H), 3.99 (s, 3H), 3.88 (m, 4H), 1.93 (m, 1H), 1.05 (m, 2H), 0.71 (m, 5H). SPA $IC_{50}$: 530 nM

Example 13

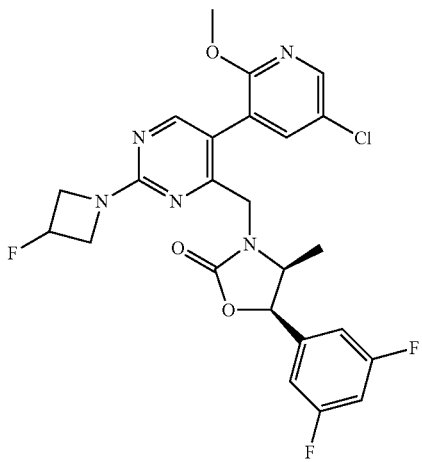 [SMILES: COc1ncc(Cl)cc1-c1cnc(N2CC(F)C2)nc1CN1C(=O)O[C@H](c2cc(F)cc(F)c2)[C@@H]1C]

(4S,5R)-3-{[5-(5-Chloro-2-methoxypyridin-3-yl)-2-(3-fluoroazetidin-1-yl)pyrimidin-4-yl]methyl}-5-(3,5-difluorophenyl)-4-methyl-1,3-oxazolidin-2-one Step A (4S,5R)-3-{[5-(5-Chloro-2-methoxypyridin-3-yl)-2-(methylsulfonyl)pyrimidin-4-yl]methyl}-5-(3,5-difluorophenyl)-4-methyl-1,3-oxazolidin-2-one Potassium peroxymonosulfate (6.29 g, 10.22 mmol) was added to a acetonitrile (27 mL) water (13 mL) suspension of (4S,5R)-3-{[5-(5-chloro-2-methoxypyridin-3-yl)-2-(methylthio)pyrimidin-4-yl]methyl}-5-(3,5-difluorophenyl)-4-methyl-1,3-oxazolidin-2-one (INTERMEDIATE 12, 2.1 g, 4.26 mmol) This was then stirred for 30 minutes at 45° C. LCMS showed complete conversion to product. The reaction was diluted with methyl t-butyl ether (50 mL) and poured into water (100 mL). The organic layer was washed twice with 100 mL aqueous NaCl and dried over sodium sulfate. It was then filtered and the filtrate concentrated to give product as white solid. No further purification was necessary.
LCMS (M+H)$^+$: 525.3

Step B (4S,5R)-3-{[5-(5-Chloro-2-methoxypyridin-3-yl)-2-(3-fluoroazetidin-1-yl)pyrimidin-4-yl]methyl}-5-(3,5-difluorophenyl)-4-methyl-1,3-oxazolidin-2-one (4S,5R)-3-{[5-(5-chloro-2-methoxypyridin-3-yl)-2-(methylsulfonyl)pyrimidin-4-yl]methyl}-5-(3,5-difluorophenyl)-4-methyl-1,3-oxazolidin-2-one (Step A, 519 mg, 0.989 mmol) and 3-fluoroazetidine hydrochloride (331 mg, 2.97 mmol) were placed in a microwave vial and suspended in THF (3 mL). $Et_3N$ (0.689 mL, 4.94 mmol) was added, the vial was sealed and the reaction heated to 100° C. for 20 minutes in a microwave reactor. LCMS showed complete conversion to product. The reaction was diluted with ethyl acetate (50 mL) and poured into 0.1N HCl solution (50 mL). The ethyl acetate layer was washed with brine (50 mL), dried over sodium sulfate and concentrated on rotary evaporator. Silica gel purification employing a 0-50% ethyl acetate/hexanes linear gradient followed by isocratic elution at 50% ethyl acetate/hexanes gave the product as a pale yellow solid. LCMS (M+H)$^+$: 520.3. $^1$H NMR (500 MHz, $CDCl_3$): δ 8.19 (d, J=2.5 Hz, 1H), 8.14 (s, 1H), 7.48 (d, J=2.5 Hz, 1H), 6.84 (m, 3H), 5.52 (m, 1.5H), 5.42 (m, 0.5H), 4.64 (d, J=17.3 Hz, 1H), 4.49 (m, 2H), 4.35 (m, 2H), 3.98 (d, J=17.3 Hz, 1H), 4.07 (m, 4H), 3.95 (s, 3H), 0.78 (d, J=6.6 Hz, 3H). SPA $IC_{50}$: 728 nM.

Example 14

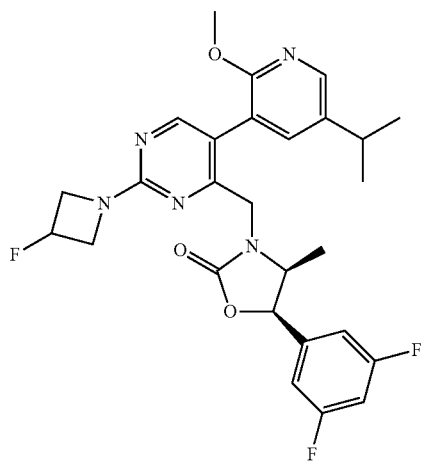 [SMILES: COc1ncc(C(C)C)cc1-c1cnc(N2CC(F)C2)nc1CN1C(=O)O[C@H](c2cc(F)cc(F)c2)[C@@H]1C]

(4S,5R)-5-(3,5-Difluorophenyl)-3-{[2-(3-fluoroazetidin-1-yl)-5-(5-isopropyl-2-methoxypyridin-3-yl)pyrimidin-4-yl]methyl}-4-methyl-1,3-oxazolidin-2-one 1,1'-Bis(di-tert-butylphosphino)ferrocene palladium dichloride (25.07 mg, 0.038 mmol) was added to a degassed THF (15 mL)/Water (3 mL) solution of (4S,5R)-3-{[5-bromo-2-(3-fluoroazetidin-1-yl)pyrimidin-4-yl]methyl}-5-(3,5-difluorophenyl)-4-methyl-1,3-oxazolidin-2-one (INTERMEDIATE 15, 200 mg, 0.385 mmol), 5-isopropyl-2-methoxypyridin-3-ylboronic acid (128 mg, 0.462 mmol) and $K_2CO_3$ (159 mg, 1.154 mmol). After further de-gassing with $N_2$ and vacuum, the reaction was heated for 1 h at 50° C. LCMS showed complete conversion to product. The reaction was diluted with 50 mL ethyl acetate and poured into 100 mL sat'd $NH_4Cl$ soln. The ethyl acetate layer was washed with brine (100 mL) filtered through a 20 g plug of sodium sulfate, eluting with 50 mL ethyl acetate. The filtrate was concentrated prior to purification with an X-Bridge 21.2×150 mm RP column. The sample was loaded in 7:3:1 $CH_3CN$/water/DMSO (5 mL), after which a 10-100% acetonitrile/water (0.1% $NH_4OH$) linear gradient at 15 mL/minutes over 20 minutes was run. The product of interest eluted in 80% portion of above gradient. Pure fractions (rich cut; impure discarded) were concentrated and lyophilized to give product as a white solid. LCMS $(M+H)^+$: 528.5. $^1H$ NMR (500 MHz, $CDCl_3$): δ 8.15 (s, 1H), 8.10 (d, J=2.1 Hz, 1H), 7.35 (d, J=2.1 Hz, 1H), 6.84 (m, 3H), 5.52 (m, 1.5H), 5.42 (m, 0.5H), 4.64 (d, J=17.3 Hz, 1H), 4.51 (m, 2H), 4.33 (m, 2H), 4.02 (d, J=17.4 Hz, 1H), 3.94 (s, 3H), 2.96 (m, 1H), 1.30 (d, J=6.9 Hz, 6H), 0.77 (d, J=6.6 Hz, 3H). RTA $IC_{50}$: 16 nM.

Example 15

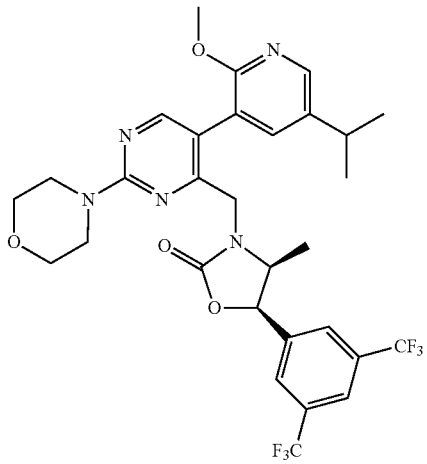 [SMILES: COc1ncc(C(C)C)cc1-c1cnc(N2CCOCC2)nc1CN1C(=O)O[C@H](c2cc(C(F)(F)F)cc(C(F)(F)F)c2)[C@@H]1C]

(4S,5R)-5-[3,5-Bis(trifluoromethyl)phenyl]-3-{[5-(5-isopropyl-2-methoxypyridin-3-yl)-2-(morpholin-4-yl)pyrimidin-4-yl]methyl}-4-methyl-1,3-oxazolidin-2-one Morpholine (0.062 mL, 0.711 mmol) was added to a THF (1 mL) solution of (4S,5R)-5-[3,5-bis(trifluoromethyl)phenyl]-3-{[5-(5-isopropyl-2-methoxypyridin-3-yl)-2-(methylsulfonyl)pyrimidin-4-yl]methyl}-4-methyl-1,3-oxazolidin-2-one (INTERMEDIATE 17, 90 mg, 0.142 mmol) in a microwave vial. The vial was capped, then heated for 15 minutes at 90° C. in a BIOTAGE microwave reactor. LCMS showed complete conversion to product. The reaction was diluted with 2 mL $CH_3CN$ and loaded directly onto an X-Bridge 21.2×150 mm RP column. Using a 10-100% acetonitrile/water (0.1% $NH_4OH$) linear gradient at 15 mL/minutes over 20 minutes, the product of interest was recovered and lyophilized to give the titled compound as a white solid. LCMS $(M+H)^+$: 640.5. $^1H$ NMR ($CDCl_3$, 500 MHz): δ 8.17 (s, 1H), 8.10 (d, J=2.2 Hz, 1H), 7.91 (s, 1H), 7.75 (s, 2H), 7.35 (d, J=2.2 Hz, 1H), 5.64 (d, J=8.5 Hz, 1H), 4.72 (d, J=17.1 Hz, 1H), 4.32 (m, 1H), 4.00 (d, J=17.2 Hz, 1H), 3.94 (s, 3H), 3.88 (m, 4H), 3.83 (m, 4H), 2.96 (m, 1H), 1.29 (d, J=7.0 Hz, 6H), 0.71 (d, J=6.5 Hz, 3H). SPA $IC_{50}$: 229 nM.

Example 16

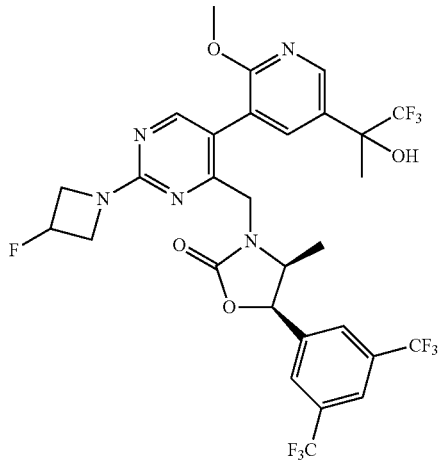 [SMILES: COc1ncc(C(C)(O)C(F)(F)F)cc1-c1cnc(N2CC(F)C2)nc1CN1C(=O)O[C@H](c2cc(C(F)(F)F)cc(C(F)(F)F)c2)[C@@H]1C]

(4S,5R)-5-[3,5-Bis(trifluoromethyl)phenyl]-3-{[2-(3-fluoroazetidin-1-yl)-5-{2-methoxy-5-[(2RS)-1,1,1-trifluoro-2-hydroxypropan-2-yl]pyridin-3-yl}pyrimidin-4-yl]methyl}-4-methyl-1,3-oxazolidin-2-one Step A (4S,5R)-5-[3,5-Bis(trifluoromethyl)phenyl]-3-{[5-{2-methoxy-5-[(2RS)-1,1,1-trifluoro-2-hydroxypropan-2-yl]pyridin-3-yl}-2-(methylthio)pyrimidin-4-yl]methyl}-4-methyl-1,3-oxazolidin-2-one Dioxane (3 mL) and 2M potassium phosphate tribasic (0.572 mL, 1.143 mmol) were added to a mixture of (4S,5R)-5-[3,5-bis(trifluoromethyl)phenyl]-3-{[5-bromo-2-(3-fluoroazetidin-1-yl)pyrimidin-4-yl]methyl}-4-methyl-1,3-oxazolidin-2-one (INTERMEDIATE 14, 220 mg, 0.381 mmol), (2RS)-2-(5-bromo-6-methoxypyridin-3-yl)-1,1,1-trifluoropropan-2-ol (INTERMEDIATE 40, 126 mg, 0.419 mmol) and tetrakis(triphenylphosphine)palladium(0) (44.0 mg, 0.038 mmol) under vacuum purged with nitrogen, placed in microwave vial and stirred for 10 minutes at 180° C. in a microwave reactor. LCMS showed complete consumption of starting material. The reaction was diluted with 20 mL methyl t-butyl ether and poured into 20 mL of aqueous NaCl. The organic was dried over sodium sulfate and concentrated. The crude was purified by silica gel chromatography eluting with 0-100% ethyl acetate/hexanes to give the titled compound as a pale yellow solid. LCMS $(M+H)^+$: 671.4

Step B (4S,5R)-5-[3,5-Bis(trifluoromethyl)phenyl]-3-{[5-{2-methoxy-5-[(2RS)-1,1,1-trifluoro-2-hydroxypropan-2-yl]pyridin-3-yl}-2-(methylsulfonyl)pyrimidin-4-yl]methyl}-4-methyl-1,3-oxazolidin-2-one Potassium peroxymonosulfate (528 mg, 0.859 mmol) was added (4S,5R)-5-[3,5-bis(trifluoromethyl)phenyl]-3-{[5-{2- methoxy-5-[(2RS)-1,1,1-trifluoro-2-hydroxypropan-2-yl]pyridin-3-yl}-2-(methylthio)pyrimidin-4-yl]methyl}-4-methyl-1,3-oxazolidin-2-one (Step A, 240 mg, 0.358 mmol) in acetonitrile (2 mL) and water (1 mL) and stirred for 1 hour at 60° C. (bath was turned off immediately and allowed to cool to 25° C. over 1 hour); LCMS showed complete conversion to product. The reaction was diluted with 20 mL methyl t-butyl ether and poured into 20 mL water; the organic layer was washed twice with water (20 mL) and finally with 50 mL brine, dried over sodium sulfate and concentrated to afford white solid.

LCMS (M+H)$^+$: 703.4

Step C (4S,5R)-5-[3,5-Bis(trifluoromethyl)phenyl]-3-{[2-(3-fluoroazetidin-1-yl)-5-{2-methoxy-5-[(2RS)-1,1,1-trifluoro-2-hydroxypropan-2-yl]pyridin-3-yl}pyrimidin-4-yl]methyl}-4-methyl-1,3-oxazolidin-2-one Triethylamine (0.218 mL, 1.566 mmol) was added to a mixture of THF (2 mL), (4S,5R)-5-[3,5-bis(trifluoromethyl)phenyl]-3-{[5-{2-methoxy-5-[(2RS)-1,1,1-trifluoro-2-hydroxypropan-2-yl]pyridin-3-yl}-2-(methylsulfonyl)pyrimidin-4-yl]methyl}-4-methyl-1,3-oxazolidin-2-one (Step B, 220 mg, 0.313 mmol) and 3-fluoroazetidine hydrochloride (105 mg, 0.939 mmol). The reaction was placed under nitrogen and heated to 60° C. for 45 minutes; LCMS showed complete conversion to product. The reaction was diluted with 20 mL ethyl acetate and poured into 20 mL 10% citric acid, The organic layer was washed with 30 mL brine, then dried over sodium sulfate and concentrated. Purification on an X-Bridge 21.2×150 mm RP column with sample loaded using 7:3:1 CH$_3$CN/water/DMSO (3 mL) employed a 10-100% acetonitrile/water (0.1% NH$_4$OH) linear gradient at 15 mL/minutes over 20 minutes. The product of interest eluted in 70% portion of the above gradient. Rich cut of pure product peak was lyophilized to give product as a white solid. LCMS (M+H)$^+$: 698.5. $^1$H NMR (500 MHz, CDCl$_3$): 1:1 diasteromeric mixture: δ 8.38 (m, 1H), 8.26 (s, 0.5H), 8.24 (s, 0.5H), 7.91 (bs, 1H), 7.82 (m, 0.5H), 7.79 (d, J=2.2 Hz, 0.5H), 7.74 (s, 1H), 7.71 (s, 1H), 5.62 (d, J=8.4 Hz, 0.5H), 5.55 (m, 0.5H), 5.44 (m, 0.5H), 4.86 (m, 0.5H), 4.72 (d, J=16.5 Hz, 0.5H), 4.52 (m, 2.5H), 4.33 (m, 3H), 4.00 (s, 1.5H), 3.42 (bs, 0.5H), 3.28 (s, 0.5H), 3.99 (s, 1.5H), 1.85 (s, 3H), 0.77 (d, J=6.6 Hz, 1.5H), 0.73 (d, J=6.6 Hz, 1.5H). RTA IC$_{50}$: 14 Nm.

Example 17

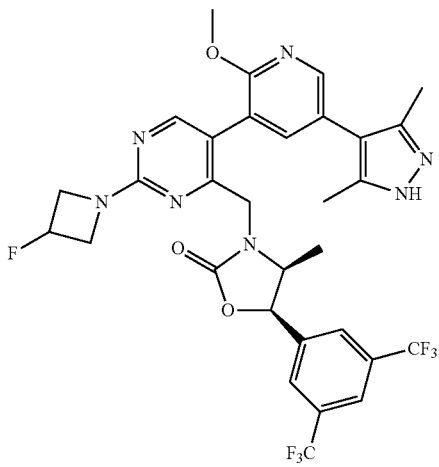 [SMILES: COc1ncc(-c2c(C)n[nH]c2C)cc1-c1cnc(N2CC(F)C2)nc1CN1C(=O)O[C@H](c2cc(C(F)(F)F)cc(C(F)(F)F)c2)[C@@H]1C]

(4S,5R)-5-[3,5-Bis(trifluoromethyl)phenyl]-3-({5-[5-(3,5-dimethyl-1H-pyrazol-4-yl)-2-methoxypyridin-3-yl]-2-(3-fluoroazetidin-1-yl)pyrimidin-4-yl}methyl)-4-methyl-1,3-oxazolidin-2-one (4S,5R)-5-[3,5-Bis(trifluoromethyl)phenyl]-3-{[5-(5-chloro-2-methoxypyridin-3-yl)-2-(3-fluoroazetidin-1-yl)pyrimidin-4-yl]methyl}-4-methyl-1,3-oxazolidin-2-one (EXAMPLE 1, 0.2 g, 0.323 mmol), 3,5-dimethyl-4-(4,4,5,5-tetramethyl-1,3,2-dioxaborolan-2-yl)-1H-pyrazole (0.0717 g, 0.323 mmol), potassium phosphate (0.103 g, 0.484 mmol), (2-dicyclohexylphosphino-2',4',6'-triisopropyl-1,1'-biphenyl)[2-(2-aminoethyl)phenyl]palladium(II) chloride (XPHOS Biphenyl Precatalyst) (0.0254 g, 0.032 mmol), THF (2.40 mL), and H$_2$O (0.80 mL) were sealed in a microwave vessel and subject to microwave irradiation at 120 C for 1.5 hours. The resulting reaction mixture was worked up with brine/ethyl acetate. The combined extracts were dried over Na$_2$SO$_4$, filtered and evaporated to afford a dark mixture. This dark mixture was purified by flash chromatography (SiO$_2$, ISCO, RediSep 12 g Cartridge). The column was eluted by an ethyl acetate/hexanes mixture (0% to 50% ethyl acetate). Related fractions were pooled and evaporated under reduced pressure to afford an off-white solid of 113 mg as the titled compound. LCMS (M+H)$^+$: 680.4. $^1$H NMR (CDCl$_3$, 500 MHz): δ 8.19-8.11 (m, 2H), 7.85 (s, 1H), 7.73 (s, 2H), 7.42-7.36 (m, 1H), 5.72-5.66 (d, J=8.5 Hz, 1H), 5.53 (s, 1H), 5.41 (s, 1H), 4.72-4.66 (m, 1H), 4.54-4.40 (m, 2H), 4.38-4.26 (m, 3H), 4.00 (s, 3H), 2.51 (m, 1H), 2.42 (s, 3H), 2.30-2.10 (m, 4H), 0.52 (d, J=6.5 Hz, 3H). RTA IC$_{50}$: 5 nM.

Example 18

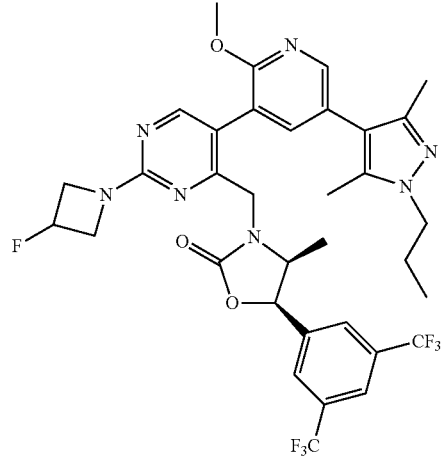 [SMILES: CCCn1nc(C)c(-c2cnc(OC)c(-c3cnc(N4CC(F)C4)nc3CN3C(=O)O[C@H](c4cc(C(F)(F)F)cc(C(F)(F)F)c4)[C@@H]3C)c2)c1C]

(4S,5R)-5-[3,5-Bis(trifluoromethyl)phenyl]-3-({5-[5-(3,5-dimethyl-1-propyl-1H-pyrazol-4-yl)-2-methoxypyridin-3-yl]-2-(3-fluoroazetidin-1-yl)pyrimidin-4-yl}methyl)-4-methyl-1,3-oxazolidin-2-one To a solution of (4S,5R)-5-[3,5-Bis(trifluoromethyl)phenyl]-3-({5-[5-(3,5-dimethyl-1H-pyrazol-4-yl)-2-methoxypyridin-3-yl]-2-(3-fluoroazetidin-1-yl)pyrimidin-4-yl}methyl)-4-methyl-1,3-oxazolidin-2-one (EXAMPLE 17, 0.020 g, 0.029 mmol) in THF (2 mL) was added sodium hydride (0.011 g, 0.29 mmol) at 0° C. The resulting mixture was stirred for 10 minutes at room temperature, after which iodopropane (0.075 g, 0.044 mmol) was added. The resulting mixture was stirred for 24 hours at room temperature until the starting material was consumed completely. Water (1 mL) was added to quench the reaction. The aqueous layer was extracted with Ethyl acetate (2×2 mL), the combined organic layer was concentrated in vacuum and the residue was dissolved in 1 mL of DMSO and filtered. This clear DMSO filtrate was purified by preparative HPLC (reverse phase, Waters SunFire Prep $C_{18}$ OBD5 um 19×100 mm) eluting with acetonitrile/water+0.14% HCOOH (30% to 100% organic in 5 minutes, 25 mL/minutes). Related fractions were pooled and evaporated under reduced pressure to afford a fluffy white solid of 2.8 mg as the titled compound. LCMS (M+H)$^+$: 722.4. $^1$H NMR (DMSO-d6, 500 MHz): δ 8.24 (s, 1H), 8.16-8.14 (d, J=8.5 Hz, 2H), 7.92 (s, 2H), 7.62 (s, 1H), 5.87 (d, J=8.5 Hz, 1H), 5.60 (s, 1H), 5.42 (s, 1H), 4.53-3.98 (br m, 4H), 3.84 (s, 3H), 2.52 (s, 3H), 2.10 (m, 3H), 2.04 (m, 2H), 1.68 (m, 1H), 1.60-1.44 (m, 2H), 0.83 (t, J=6.5 Hz, 3H), 0.54 (d, J=6.5 Hz, 3H). RTA IC$_{50}$: 12 nM The following compounds (Table 4) were synthesized using methods analogous to those described in EXAMPLE 18.

TABLE 4

| EXAMPLE | Molecular structure | LCMS (M + H)$^+$ | CETP Inhibition |
|---|---|---|---|
| 19 | 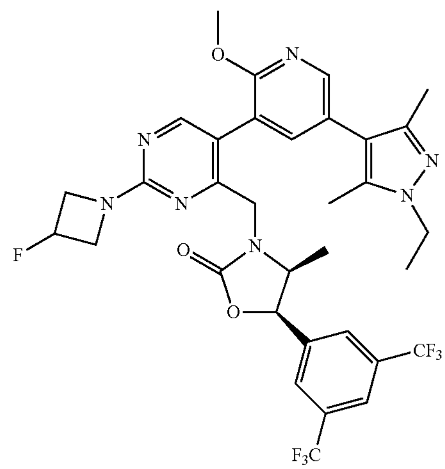 [SMILES: CCn1nc(C)c(-c2cnc(OC)c(-c3cnc(N4CC(F)C4)nc3CN3C(=O)O[C@H](c4cc(C(F)(F)F)cc(C(F)(F)F)c4)[C@@H]3C)c2)c1C] | 708.4 | RTA IC$_{50}$: 9 nM |
| 20 | 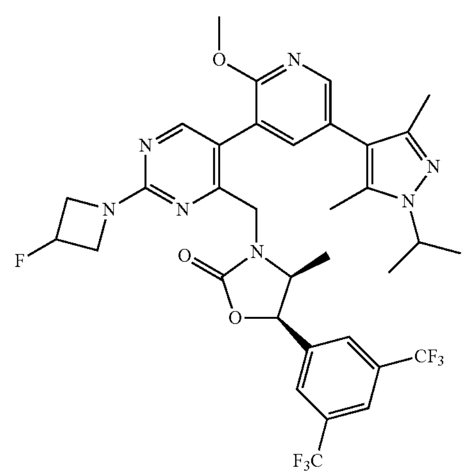 [SMILES: COc1ncc(-c2c(C)nn(C(C)C)c2C)cc1-c1cnc(N2CC(F)C2)nc1CN1C(=O)O[C@H](c2cc(C(F)(F)F)cc(C(F)(F)F)c2)[C@@H]1C] | 736.4 | RTA IC$_{50}$: 36 nM |

TABLE 4-continued

| EXAMPLE | Molecular structure | LCMS (M + H)+ | CETP Inhibition |
|---|---|---|---|
| 21 | 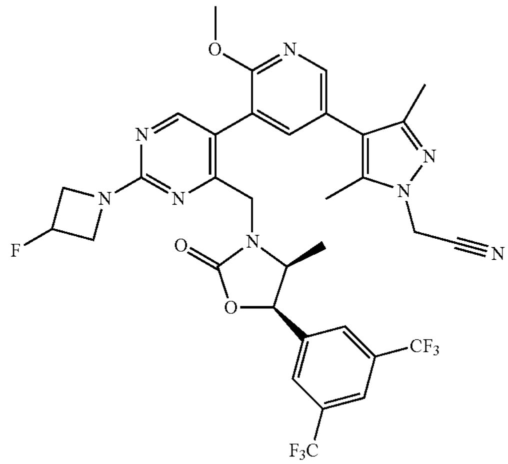 [SMILES: COc1ncc(-c2c(C)nn(CC#N)c2C)cc1-c1cnc(N2CC(F)C2)nc1CN1C(=O)O[C@H](c2cc(C(F)(F)F)cc(C(F)(F)F)c2)[C@@H]1C] | 719.3 | RTA IC$_{50}$: 18 nM |
| 22 | 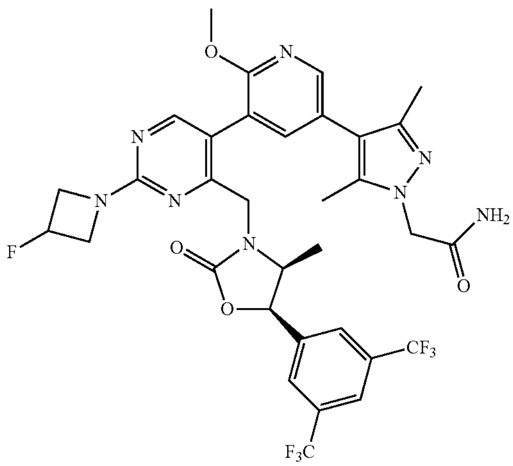 [SMILES: COc1ncc(-c2c(C)nn(CC(N)=O)c2C)cc1-c1cnc(N2CC(F)C2)nc1CN1C(=O)O[C@H](c2cc(C(F)(F)F)cc(C(F)(F)F)c2)[C@@H]1C] | 737.4 | RTA IC$_{50}$: 22 nM |

Example 23

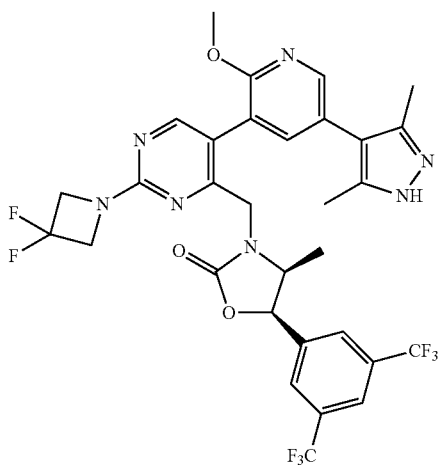 [SMILES: COc1ncc(-c2c(C)n[nH]c2C)cc1-c1cnc(N2CC(F)(F)C2)nc1CN1C(=O)O[C@H](c2cc(C(F)(F)F)cc(C(F)(F)F)c2)[C@@H]1C]

(4S,5R)-5-[3,5-Bis(trifluoromethyl)phenyl]-3-({2-(3,3-difluoroazetidin-1-yl)-5-[5-(3,5dimethyl-1H-pyrazol-4-yl)-2-methoxypyridin-3-yl]pyrimidin-4-yl}methyl)-4-methyl-1,3-oxazolidin-2-one Step A: (4S,5R)-5-[3,5-Bis(trifluoromethyl)phenyl]-3-({5-[2-methoxy-5-(4,4,5,5-tetramethyl-1,3,2-dioxaborolan-2-yl)pyridin-3-yl]-2-(methylthio)pyrimidin-4-yl}methyl)-4-methyl-1,3-oxazolidin-2-one DMA (11.47 mL) was added to a mixture of (4S,5R)-5-[3,5-bis(trifluoromethyl)phenyl]-3-{[5-(5-chloro-2-methoxypyridin-3-yl)-2-(methylthio)pyrimidin-4-yl]methyl}-4-methyl-1,3-oxazolidin-2-one (INTERMEDIATE 16, 1.7 g, 2.87 mmol), bis(pinacolato)diboron (2.184 g, 8.60 mmol) and (2-dicyclohexylphosphino-2',4',6'-triisopropyl-1,1'-biphenyl)[2-(2-aminoethyl)phenyl)]palladium(II) chloride (XPHOS Biphenyl Precatalyst) (0.113 g, 0.143 mmol), which was then put under vacuum and purged with nitrogen. The reaction stirred for 90 minutes at 80° C. at which time LCMS showed 15% conversion to desired product and clean profile. The reaction temperature was raised to 100° C. and allowed to stir overnight under nitrogen atmosphere. LCMS then showed >80% conversion to boronate ester/boronic acid. The reaction was diluted with 50 mL methyl t-butyl ether and poured into 100 mL of 1/1 water/sat'd NaCl solution. The organic layer was then dried over sodium sulfate, filtered, evaporated and the filtrate concentrated on rotovap prior to purification. The compound was purified by silica gel chromatography with a 0-100% ethyl acetate/hexanes linear gradient. The gradient was held at 30% ethyl acetate/hexanes for 10 minutes. The product of interest eluted in 30% portion of above gradient. Pure fractions were concentrated to give 1.2 g product. LCMS (M+H)$^+$: 685.4

Step B: (4S,5R)-5-[3,5-Bis(trifluoromethyl)phenyl]-3-({5-[5-(3,5-dimethyl-1H-pyrazol-4-yl)-2-methoxypyridin-3-yl]-2-(methylthio)pyrimidin-4-yl}methyl)-4-methyl-1,3-oxazolidin-2-one (4S,5R)-5-[3,5-Bis(trifluoromethyl)phenyl]-3-({5-[2-methoxy-5-(4,4,5,5-tetramethyl-1,3,2-dioxaborolan-2-yl)pyridin-3-yl]-2-(methylthio)pyrimidin-4-yl}methyl)-4-methyl-1,3-oxazolidin-2-one (Step A, 0.76 g, 1.11 mmol), 4-bromo-3,5-dimethyl-1H-pyrazole (0.233 g, 1.33 mmol), tripotassium phosphate (1.178 g, 5.50 mmol), (2-dicyclohexylphosphino-2',4',6'-triisopropyl-1,1'-biphenyl)[2-(2-aminoethyl)phenyl)]palladium(II) chloride (XPHOS Biphenyl Precatalyst) (0.087 g, 0.11 mmol), THF (8.33 mL), and H$_2$O (2.77 mL) were sealed in a microwave vessel and subject to microwave irradiation at 120° C. for 1.5 hrs. The resulting reaction mixture was worked up with brine/ethyl acetate. The combined extracts were dried over Na$_2$SO$_4$, filtered and evaporated to afford a brown mixture. This mixture was purified by flash chromatography (SiO$_2$, ISCO, RediSep 24 g Cartridge). The column was eluted by an ethyl acetate/hexanes mixture (0% to 50% ethyl acetate). Related fractions were pooled and evaporated under reduced pressure to afford an off-white solid of 450 mg as the titled compound. LCMS (M+H)$^+$: 653.35.

Step C: (4S,5R)-5-[3,5-Bis(trifluoromethyl)phenyl]-3-({5-[5-(3,5-dimethyl-1H-pyrazol-4-yl)-2-methoxypyridin-3-yl]-2-(methylsulfonyl)pyrimidin-4-yl}methyl)-4-methyl-1,3-oxazolidin-2-one To a solution of (4S,5R)-5-[3,5-Bis(trifluoromethyl)phenyl]-3-({5-[5-(3,5-dimethyl-1H-pyrazol-4- yl)-2-methoxypyridin-3-yl]-2-(methylthio)pyrimidin-4-yl}methyl)-4-methyl-1,3-oxazolidin-2-one (Step B, 0.42 g, 0.64 mmol) in CH$_2$Cl$_2$ (7 mL) was added mCPBA (0.244 g, 1.42 mmol) at room temperature. The reaction mixture was stirred for 4 hours at the same temperature. The resulting reaction mixture was worked up with brine/CH$_2$Cl$_2$. The combined extracts were dried over Na$_2$SO$_4$, filtered and evaporated to afford a yellow mixture. This mixture was purified by flash chromatography (SiO$_2$, ISCO, RediSep 24 g Cartridge). The column was eluted by an ethyl acetate/hexanes mixture (0% to 50% ethyl acetate). Related fractions were pooled and evaporated under reduced pressure to afford 258 mg of a light yellow solid as the titled compound. LCMS (M+H)$^+$: 685.4

Step D: (4S,5R)-5-[3,5-Bis(trifluoromethyl)phenyl]-3-({2-(3,3-difluoroazetidin-1-yl)-5-[5-(3,5-dimethyl-1H-pyrazol-4-yl)-2-methoxypyridin-3-yl]pyrimidin-4-yl}methyl)-4-methyl-1,3-oxazolidin-2-one (4S,5R)-5-[3,5-Bis(trifluoromethyl)phenyl]-3-({5-[5-(3,5-dimethyl-1H-pyrazol-4-yl)-2-methoxypyridin-3-yl]-2-(methylsulfonyl)pyrimidin-4-yl}methyl)-4-methyl-1,3-oxazolidin-2-one (Step C, 0.020 g, 0.029 mmol), 3,3-difluoroazitidine (0.004 g, 0.044 mmol), DIEA (11.33 mg, 0.088 mmol), and THF (1.0 mL) were sealed in a microwave vessel and subject to microwave irradiation at 100° C. for 1.5 hrs. The resulting reaction mixture was worked up with brine/ethyl acetate. The combined extracts were dried over Na$_2$SO$_4$, filtered and evaporated to afford a dark mixture. This mixture was dissolved in 1 mL of DMSO, filtered it. This solution was purified by preparative HPLC (reverse phase, Waters SunFire PrepC 18 OBD5 um 19×100 mm) eluting with acetonitrile/water+0.14% HCOOH (30% to 100% organic in 5 minutes, 25 mL/minutes). Related fractions were pooled and evaporated under reduced pressure to afford a fluffy white solid of 2.8 mg as the titled compound. LCMS (M+H)$^+$: 698.3.

$^1$H NMR (DMSO-d6, 500 MHz): δ 8.35 (s, 1H), 8.18-8.16 (d, J=8.5 Hz, 2H), 8.00 (s, 2H), 7.62 (s, 1H), 5.92 (d, J=8.5 Hz, 1H), 4.62-4.38 (br m, 7H), 4.10 (m, 1H), 3.86 (s, 3H), 2.58 (s, 3H), 2.28 (s, 3H), 0.60 (d, J=6.5 Hz, 3H). RTA IC$_{50}$: 15 nM.

The following compounds (Table 5) were synthesized using methods analogous to those described above.

TABLE 5

| EXAMPLE | Molecular structure | LCMS (M + 1)$^+$ | CETP Inhibition |
|---|---|---|---|
| 24 | 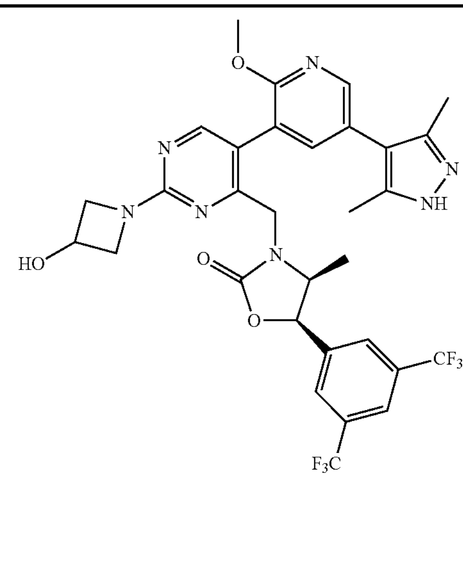 | 678.3 | RTA IC$_{50}$: 332 nM |

TABLE 5-continued
| EXAMPLE | Molecular structure | LCMS (M + 1)+ | CETP Inhibition |
|---|---|---|---|
| 25 | 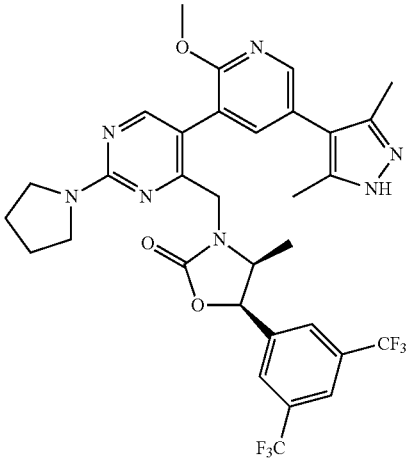 [SMILES: COc1ncc(-c2c(C)n[nH]c2C)cc1-c1cnc(N2CCCC2)nc1CN1C(=O)O[C@H](c2cc(C(F)(F)F)cc(C(F)(F)F)c2)[C@@H]1C] | 676.4 | RTA IC$_{50}$: 20 nM |
| 26 | 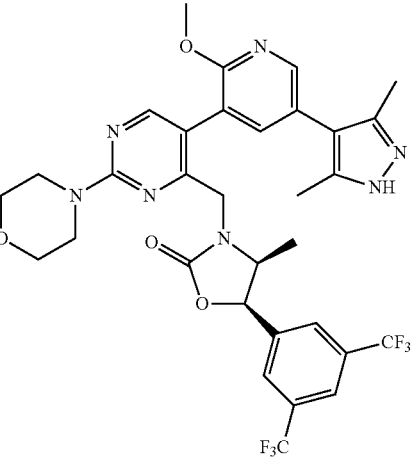 | 692.4 | RTA IC$_{50}$: 23 nM |
| 27 | 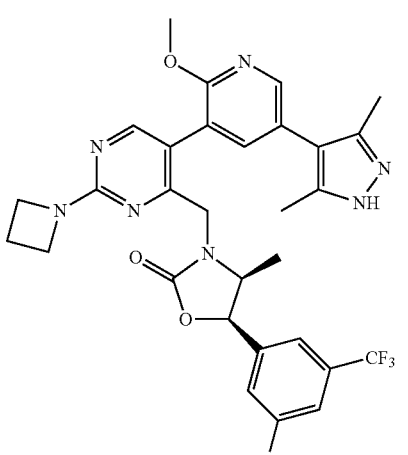 | 662.3 | RTA IC$_{50}$: 19 nM |

Example 28

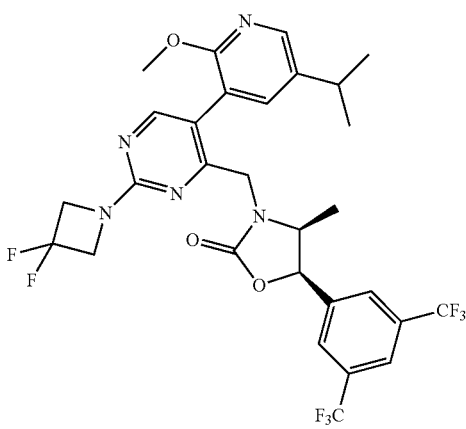 [SMILES: COc1ncc(C(C)C)cc1-c1cnc(N2CC(F)(F)C2)nc1CN1C(=O)O[C@H](c2cc(C(F)(F)F)cc(C(F)(F)F)c2)[C@@H]1C]

(4S,5R)-5-[3,5-Bis(trifluoromethyl)phenyl]-3-{[2-(3,3-difluoroazetidin-1-yl)-5-(5-isopropyl-2-methoxy-pyridin-3-yl)pyrimidin-4-yl]methyl}-4-methyl-1,3-oxazolidin-2-one A solution of (4S,5R)-5-[3,5-bis(trifluoromethyl)phenyl]-3-{[5-(5-isopropyl-2-methoxypyridin-3-yl)-2-(methylsulfonyl)pyrimidin-4-yl]methyl}-4-methyl-1,3-oxazolidin-2-one (INTERMEDIATE 17, 80 mg, 0.126 mmol) in 1 mL THF was added to 1 dram vial that contained 3,3-difluoroazetidine hydrochloride (11.8 mg, 0.126 mmol). Triethylamine (0.071 mL, 0.506 mmol) was added, the vial was capped and the reaction mixture heated to 60° C. for 3 hours. The mixture was cooled to ambient temperature and stirred overnight. Diluted the mixture with ethyl acetate (2 mL) and washed with H$_2$O (3×1 mL), brine (1×1 mL), dried over MgSO$_4$, filtered and concentrated in vacuo. Purified the residue by RP HPLC (Waters Sunfire C$_{18}$ column; 19×100 mm; 5 µM; CH$_3$CN/H$_2$O (0.1% TFA); 20-90% gradient; 20 mL/minutes; 12 minutes run) and the corresponding fractions that contained product were lyophilized to afford 45 mg of a white powder as the titled compound. LCMS (M+H)$^+$: 646.3. $^1$H NMR (500 MHz, CDCl$_3$): δ: 0.73 (d, 3H, J=7.5 Hz), 1.28 (d, 6H, J=6.9 Hz), 2.95 (septet, 1H, J=7.5 Hz), 3.95 (s, 3H), 4.04 (d, 1H, J=7.5 Hz), 4.54-4.59 (m, 4H), 4.64 (d, 1H, J=7.5 Hz), 5.65 (d, 1H, J=8.5 Hz), 7.40 (d, 1H, J=2.4 Hz), 7.73 (s, 2H), 7.90 (s, 1H), 8.13 (d, 1H, J=2.4 Hz), 8.23 (s, 1H). RTA IC$_{50}$: 5 nM The following compounds (Table 6) were synthesized using methods analogous to those for EXAMPLE 28.

TABLE 6

| EXAMPLE | STRUCTURE | LCMS (M + H)$^+$ | CETP Inhibition |
|---|---|---|---|
| 29 | 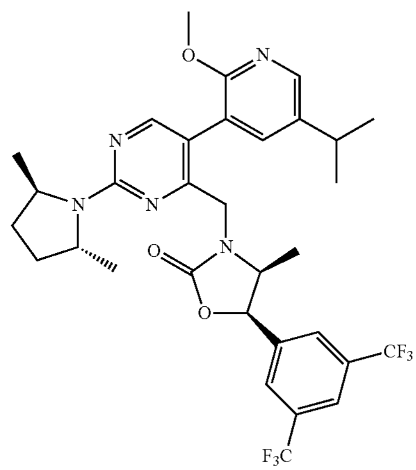 [SMILES: COc1ncc(C(C)C)cc1-c1cnc(N2[C@H](C)CC[C@H]2C)nc1CN1C(=O)O[C@H](c2cc(C(F)(F)F)cc(C(F)(F)F)c2)[C@@H]1C] | 652.4 | RTA IC$_{50}$: 430 nM |
| 30 | 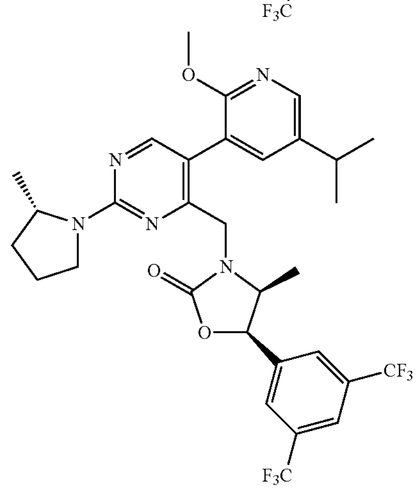 | 638.4 | RTA IC$_{50}$: 18 nM |

TABLE 6-continued

| EXAMPLE | STRUCTURE | LCMS (M + H)+ | CETP Inhibition |
|---|---|---|---|
| 31 | (structure) | 610.3 | RTA IC$_{50}$: 5 nM |

Example 32

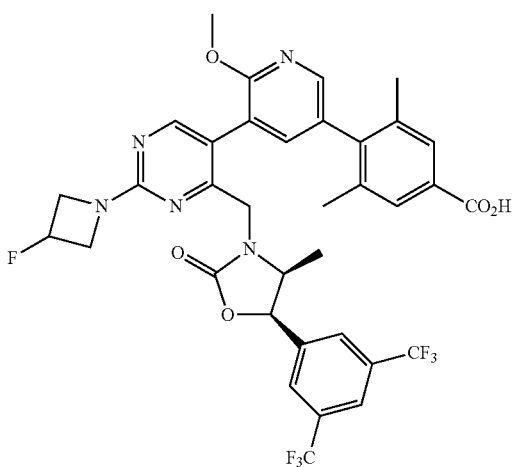 [SMILES: COc1ncc(-c2c(C)cc(C(=O)O)cc2C)cc1-c1cnc(N2CC(F)C2)nc1CN1C(=O)O[C@H](c2cc(C(F)(F)F)cc(C(F)(F)F)c2)[C@@H]1C]

4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3,5-dimethylbenzoic acid Step A: Methyl 4-{5-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3,5-dimethylbenzoate 3-Fluoroazetidine hydrochloride (26.7 mg, 0.239 mmol), methyl 4-{5-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3,5-dimethylbenzoate (INTERMEDIATE 44, 60 mg, 0.080 mmol), THF (800 µl) and triethylamine (55.6 µl, 0.399 mmol) were stirred at 100° C. for 10 minutes in the microwave reactor. Once complete, the reaction was partitioned between water and ethyl acetate. The organic was then washed with brine, dried over sodium sulfate, filtered and evaporated. The crude was purified by silica gel chromatography, eluting with 25-100% ethyl acetate/hexanes to give the titled compound. $^1$H NMR (CDCl$_3$, 500 MHz): δ8.15 (s, 1H), 68.02 (d, 1H), 67.89 (s, 1H), 67.80 (s, 2H), 67.74 (s, 2H), 67.28 (d, 1H), 65.71 (d, 1H), 65.51 (m, 0.5H), 65.40 (m, 0.5H), 64.71 (d, 1H), 64.45 (m, 3H), 64.30 (m, 2H), 64.00 (d, s, 4H), 63.93 (s, 3H), 62.14 (d, 6H), 60.74 (d, 3H).

Step B: 4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3,5-dimethylbenzoic acid Methyl 4-{5-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3,5-dimethylbenzoate (Step A, 55.6 mg, 0.074 mmol) was dissolved in 1,4-dioxane (1500 µl). Added 0.5N lithium hydroxide (750 µl, 0.375 mmol) and stirred at room temperature for 3 hours at which time LCMS shows complete hydrolysis. The reaction was quenched by adding 0.375 mL of 1N HCl, followed by water. The reaction was extracted with ethyl acetate. The ethyl acetate layer was dried over sodium sulfate, filtered and evaporated. Purified on Biotage SNAP 13 g C$_{18}$ column, eluting with 25-100% CH$_3$CN/water (0.05% TFA) and recovering purified fractions by partitioning them between pH 7 phosphate buffer and ethyl acetate. Extracted the aqueous a second time with ethyl acetate, then washed the combined organics with pH 7.0 buffer and brine. The organic was dried over sodium sulfate, filtered and evaporated to give the titled compound. LCMS (M+H)+: 734.5. $^1$H NMR (CDCl$_3$, 500 MHz): δ8.17 (s, 1H), 8.04 (d, 1H), 7.89 (s, 1H), 7.86 (d, 2H), 7.75 (s, 2H), 7.30 (d, 1H), 5.71

(d, 1H), 5.51 (m, 0.5H), 5.40 (m, 0.5H), 4.71 (d, 1H), 4.45 (m, 3H), 4.30 (m, 2H), 4.00 (d, s, 4H), 2.16 (d, 6H), 0.75 (d, 3H). RTA IC$_{50}$: 7 nM

Example 33

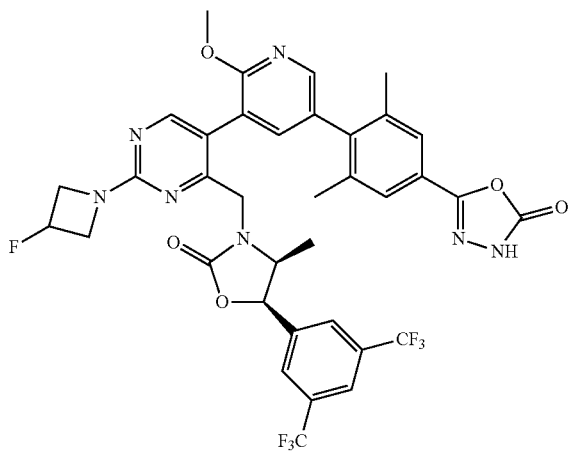 [SMILES: COc1ncc(-c2c(C)cc(-c3n[nH]c(=O)o3)cc2C)cc1-c1cnc(N2CC(F)C2)nc1CN1C(=O)O[C@H](c2cc(C(F)(F)F)cc(C(F)(F)F)c2)[C@@H]1C]

5-(4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3,5-dimethylphenyl)-1,3,4-oxadiazol-2(3H)-one Step A: 4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3,5-dimethylbenzohydrazide Methyl 4-{5-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3,5-dimethylbenzoate (EXAMPLE 32 Step A, 0.091 g, 0.122 mmol) was dissolved in ethanol (0.80 mL). Added hydrazine (0.115 mL, 3.65 mmol) and stirred at 85° C. in a screw cap vial (with a pressure relief cap) under a nitrogen blanket. The reaction was monitored by LCMS. Once complete the reaction was cooled to room temperature. The solvent was removed by rotary evaporation and the crude isolate was partitioned between ethyl acetate and water. Washed the organic twice more with water, then once with brine, dried over sodium sulfate, filtered and evaporated to give an off-white foam as the product. The compound was used without further purification. $^1$H NMR (CDCl$_3$, 500 MHz): δ 8.15 (s, 1H), 8.00 (d, 1H), 7.88 (s, 1H), 7.74 (s, 2H), 7.51 (d, 2H), 7.43 (s, 1H), 7.27 (d, 1H), 5.70 (d, 1H), 5.51 (m, 0.5H), 5.40 (m, 0.5H), 4.69 (d, 1H), 4.45 (m, 3H), 4.29 (m, 2H), 3.99 (m, s, 4H), 2.14 (s, 3H), 2.13 (s, 3H), 1.65 (br, 2H), 0.74 (d, 3H).

Step B: 5-(4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3,5-dimethylphenyl)-1,3,4-oxadiazol-2(3H)-one A solution of 4-{5-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3,5-dimethylbenzohydrazide (Step A, 90 mg, 0.120 mmol) in THF (1.2 mL) was treated with N,N-carbonyldiimidazole (58.6 mg, 0.361 mmol). The reaction was stirred at room temperature overnight. The reaction was purified directly by silica gel chromatography, eluting with a gradient of 25-100% ethyl acetate/hexanes to give the titled compound. LCMS (M+H)$^+$: 774.6. $^1$H NMR (CDCl$_3$, 500 MHz): δ 9.12 (br, 1H), 8.17 (s, 1H), 8.03 (d, 1H), 7.89 (s, 1H), 7.74 (s, 2H), 7.61 (d, 2H), 7.31 (d, 1H), 5.71 (d, 1H), 5.51 (m, 0.5H), 5.40 (m, 0.5H), 4.71 (d, 1H), 4.47 (m, 3H), 4.31 (m, 2H), 4.01 (m, s, 4H), 2.16 (s, 3H), 2.15 (s, 3H), 0.76 (d, 3H). RTA IC$_{50}$: 8 nM Example 34

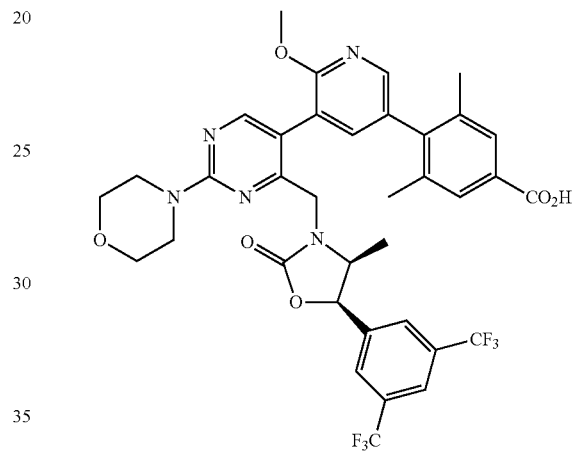

4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3,5-dimethylbenzoic acid Step A: Methyl 4-{5-[44 {(4S,5R)-5-[3,5-bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3,5-dimethylbenzoate Morpholine (206 µl, 2.358 mmol), methyl 4-{5-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3,5-dimethylbenzoate (INTERMEDIATE 44, 355 mg, 0.472 mmol), and THF (2.4 mL) were stirred at 100° C. for 10 minutes in the microwave reactor, at which time LCMS showed complete conversion to target. The reaction was partitioned between water and ethyl acetate. The organic was then washed with brine, dried over sodium sulfate, filtered and evaporated. The crude isolate was purified by silica gel chromatography, eluting with 25-100% ethyl acetate/hexanes to give the titled compound. $^1$H NMR (CDCl$_3$, 500 MHz): δ 8.16 (s, 1H), 8.01 (d, 1H), 7.89 (s, 1H), 7.80 (d, 2H), 7.73 (s, 2H), 7.27 (d, 1H), 5.66 (d, 1H), 4.72 (d, 1H), 4.32 (m, 1H), 4.00 (m, s, 4H), 3.93 (s, 3H), 3.84 (m, 4H), 3.80 (m, 4H), 2.15 (s, 3H), 2.13 (s, 3H), 0.72 (d, 3H).

Step B: 4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3,5-dimethylbenzoic acid Methyl 4-{5-[4-({(4S,5R)-5-[3,5-bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3,5-dimethylbenzoate (Step A, 100 mg, 0.132 mmol) was dissolved in 1,4-dioxane (2.5 mL). Lithium hydroxide (0.5M, 1.2 mL, 0.600 mmol) was added and the reaction was stirred at room temperature for 2 hours. The reaction was quenched by adding 0.600 mL of 1N HCl, followed by water. The aqueous reaction mixture was extracted with ethyl acetate, then dried over sodium sulfate, filtered and evaporated. Purified on BIOTAGE SNAP 13 g $C_{18}$ column, eluting with 25-100% $CH_3CN$/water (0.05% TFA) and recovering purified fractions by partitioning them between pH 7 phosphate buffer and ethyl acetate. Extracted the aqueous a second time with ethyl acetate, then washed the combined organics with pH 7.0 buffer and brine. The organic was dried over sodium sulfate, filtered and evaporated to give the titled compound. LCMS (M+H)$^+$: 746.2. $^1$H NMR (CDCl$_3$, 500 MHz): δ 8.17 (s, 1H), 8.03 (d, 1H), 7.88 (m, 3H), 7.73 (s, 2H), 7.29 (d, 1H), 5.67 (d, 1H), 4.73 (d, 1H), 4.34 (m, 1H), 4.01 (m, s, 4H), 3.86 (m, 4H), 3.81 (m, 4H), 2.18 (s, 3H), 2.15 (s, 3H), 0.72 (d, 3H). RTA IC$_{50}$: 10 nM.

Example 35

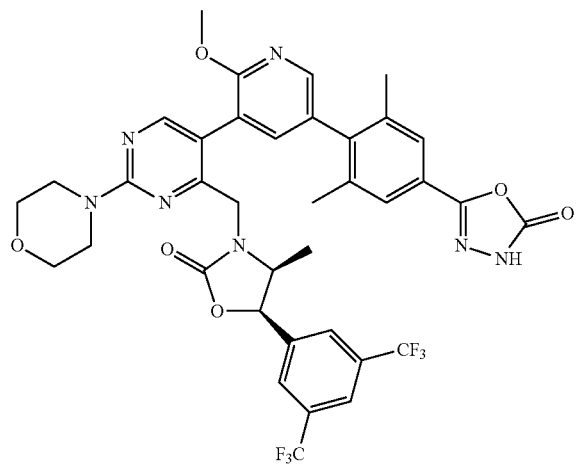 [SMILES: COc1ncc(-c2c(C)cc(-c3n[nH]c(=O)o3)cc2C)cc1-c1cnc(N2CCOCC2)nc1CN1C(=O)O[C@H](c2cc(C(F)(F)F)cc(C(F)(F)F)c2)[C@@H]1C]

5-(4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3,5-dimethylphenyl)-1,3,4-oxadiazol-2(3H)-one Step A: 4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3,5-dimethylbenzohydrazide Methyl 4-{5-[4-({(4S,5R)-5-[3,5-bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3,5-dimethylbenzoate (EXAMPLE 34 Step A, 0.051 g, 0.067 mmol) was dissolved in ethanol (0.45 mL). Added hydrazine (0.063 mL, 2.014 mmol) and stirred at 85° C. in a screw cap vial (pressure relief type) under a nitrogen blanket. Once complete, the solvent was removed by rotary evaporation and the crude isolate was partitioned between ethyl acetate and water. Washed the organic twice more with water, then once with brine, dried over sodium sulfate, filtered and evaporated to give an off-white foam as the product. The compound was used without further purification. $^1$H NMR (CDCl$_3$, 500 MHz): δ 8.16 (s, 1H), 8.00 (d, 1H), 7.88 (s, 1H), 7.73 (s, 2H), 7.49 (s, 2H), 7.35 (s, 1H), 7.26 (d+s, 1H+CHCl3), 5.66 (d, 1H), 4.71 (d, 1H), 4.33 (m, 1H), 4.10 (m, 1H), 4.00 (s, 3H), 3.85 (m, 4H), 3.80 (m, 4H), 2.15 (s, 3H), 2.13 (s, 3H), 1.60 (br, 2H), 0.72 (d, 3H).

Step B: 5-(4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3,5-dimethylphenyl)-1,3,4-oxadiazol-2(3H)-one 4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3,5-dimethylbenzohydrazide (Step A, 45.4 mg, 0.060 mmol) was dissolved in THF (600 μl) and treated with N,N-carbonyldiimidazole (58.6 mg, 0.361 mmol). The reaction was stirred at room temperature overnight. The reaction was purified directly by silica gel chromatography, eluting with a gradient of 25-100% ethyl acetate/hexanes to give the title compound. $^1$H NMR (CDCl$_3$, 500 MHz): δ 8.97 (s, 1H), 8.17 (s, 1H), 8.02 (d, 1H), 7.89 (s, 1H), 7.73 (s, 2H), 7.62 (d, 2H), 7.29 (d, 1H), 5.67 (d, 1H), 4.72 (d, 1H), 4.35 (m, 1H), 4.01 (m, s, 4H), 3.86 (m, 4H), 3.80 (m, 4H), 2.16 (s, 3H), 2.14 (s, 3H), 0.73 (d, 3H). RTA IC$_{50}$: 10 nM.

Example 36

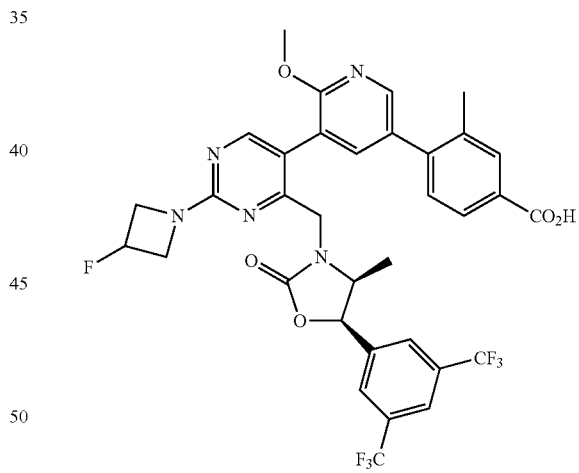

4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3-methylbenzoic acid Step A: Methyl 4-{5-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3-methylbenzoate 3-Fluoroazetidine hydrochloride (159 mg, 1.422 mmol), methyl 4-{5-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3-methylbenzoate (INTERMEDIATE 46, 350 mg, 0.474 mmol), THF (2.4 mL) and triethylamine (330 µl, 2.369 mmol) were stirred at 100° C. for 10 minutes in the microwave reactor. Once complete, the reaction was partitioned between water and ethyl acetate. The organic was then washed with brine, dried over sodium sulfate, filtered and evaporated. The crude was purified by silica gel chromatography, eluting with 25-100% ethyl acetate/hexanes to give the title compound. $^1$H NMR (CDCl$_3$, 500 MHz): δ 8.21 (d, 1H), 8.17 (s, 1H), 7.98 (s, 1H), 7.92 (d, 1H), 7.88 (s, 1H), 7.73 (s, 2H), 7.47 (d, 1H), 7.31 (d, 1H), 5.68 (d, 1H), 5.51 (m, 0.5H), 5.40 (m, 0.5H), 4.72 (d, 1H), 4.47 (m, 3H), 4.30 (m, 2H), 4.00 (d, s, 4H), 3.93 (s, 3H), 2.37 (s, 3H), 0.74 (d, 3H).

Step B: 4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3-methylbenzoic acid Methyl 4-{5-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3-methylbenzoate (Step A, 200 mg, 0.273 mmol) was dissolved in 1,4-dioxane (5 mL). Added 0.5N lithium hydroxide (2.5 mL, 1.25 mmol) and stirred at room temperature for 3 hours at which time LCMS showed complete hydrolysis. The reaction was quenched by adding 1.25 mL of 1N HCl, followed by water. The reaction was extracted with ethyl acetate. The ethyl acetate layer was dried over sodium sulfate, filtered and evaporated. The crude isolate was purified on a BIOTAGE SNAP 30 g C$_{18}$ column, eluting with 40-100% CH$_3$CN/water (0.05% TFA). The purified fractions were partitioned between pH 7 phosphate buffer and ethyl acetate. The aqueous was extracted a second time with ethyl acetate, then washed with pH 7.0 buffer and brine. The organic was dried over sodium sulfate, filtered and evaporated to give the title compound. LCMS (M+H)$^+$: 720.4. $^1$H NMR (CDCl$_3$, 500 MHz): δ 8.22 (d, 1H), 8.20 (s, 1H), 8.04 (s, 1H), 7.98 (d, 1H), 7.89 (s, 1H), 7.74 (s, 2H), 7.49 (d, 1H), 7.35 (d, 1H) 5.68 (d, 1H), 5.51 (m, 0.5H), 5.40 (m, 0.5H), 4.74 (d, 1H), 4.47 (m, 3H), 4.32 (m, 2H), 4.00 (d, s, 4H), 2.39 (s, 3H), 0.75 (d, 3H). RTA IC$_{50}$: 12 nM.

Example 37

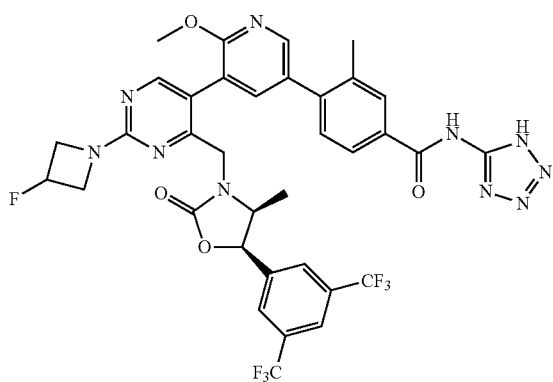 [SMILES: COc1ncc(-c2ccc(C(=O)Nc3nnn[nH]3)cc2C)cc1-c1cnc(N2CC(F)C2)nc1CN1C(=O)O[C@H](c2cc(C(F)(F)F)cc(C(F)(F)F)c2)[C@@H]1C]

4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3-methyl-N-(1H-tetrazol-5-yl)benzamide To a solution of 4-{5-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3-methylbenzoic acid (EXAMPLE 36, 167 mg, 0.232 mmol), EDC (90 mg, 0.464 m mol), HOBt (60 mg, 0.437 m mol), and DIEA (81 µl, 0.464 m mol) in DMF (2 mL) was added 5-aminotetrazole monohydrate (120 mg, 1.16 mmol). After stirring at 40° C. for 8 hours, the reaction mixture was directly applied to reverse phase HPLC, eluting with 10% to 100% acetonitrile in water, to get the title compound (121 mg, 43% yield), as a white solid after lyophilization. LCMS (M+H)$^+$: 787.2. $^1$H NMR (DMSO-d6, 500 MHz): δ 12.44 (s, 1H), 8.31 (s, 1H), 8.29 (d, 3.5 Hz, 1H), 8.12 (s, 1H), 8.09 (s, 1H), 8.00 (m, 3H), 7.82 (d, 2.0 Hz, 1H), 7.50 (d, 8.0 Hz, 1H), 5.91 (d, 8.5 Hz, 1H), 5.59 (m, 1H), 4.53 (d, 17.0 Hz, 1H), 4.49-4.38 (m, 3H), 4.22-4.07 (m, 3H), 3.93 (s, 3H), 2.40 (s, 3H), 0.64 (d, 6.5 Hz, 3H). RTA IC$_{50}$: 10 nM.

Example 38

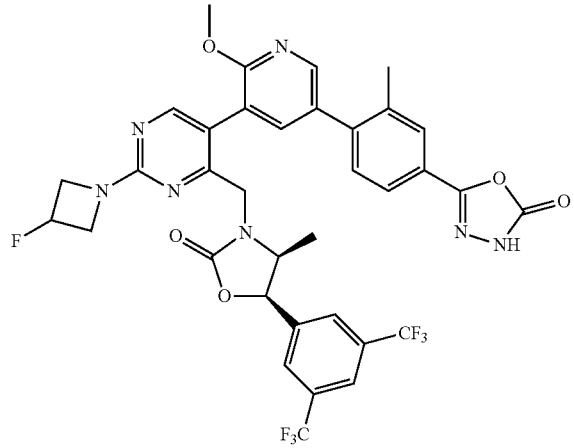 [SMILES: COc1ncc(-c2ccc(-c3n[nH]c(=O)o3)cc2C)cc1-c1cnc(N2CC(F)C2)nc1CN1C(=O)O[C@H](c2cc(C(F)(F)F)cc(C(F)(F)F)c2)[C@@H]1C]

5-(4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3-methylphenyl)-1,3,4-oxadiazol-2(3H)-one Step A: 4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3-methylbenzohydrazide Methyl 4-{5-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3-methylbenzoate (EXAMPLE 36 Step A, 0.091 g, 0.122 mmol) was dissolved in ethanol (0.83 mL). Added hydrazine (0.117 mL, 3.65 mmol) and stirred at 85° C. in a screw cap vial (with a pressure relief cap) under a nitrogen blanket. The reaction was monitored by LCMS. Once complete, the reaction was cooled to room temperature. The solvent was removed by rotary evaporation, and the crude isolate was partitioned between ethyl acetate and water. Washed the organic twice more with water, then once with brine, dried over sodium sulfate, filtered and evaporated to give an off-white foam as the product. The compound was used without further purification. $^1$H NMR (CDCl$_3$, 500 MHz): δ 8.19 (d, 1H), 8.17 (s, 1H), 7.89 (s, 1H), 7.74 (s, 2H), 7.71 (s, 1H), 7.61 (dd, 1H), 7.46 (d, 1H), 7.36 (s, 1H), 7.32 (d, 1H), 5.67 (d, 1H), 5.51 (m, 0.5H), 5.40 (m, 0.5H), 4.71 (d, 1H), 4.44 (m, 3H), 4.31 (m, 2H), 4.00 (m, s, 4H), 2.37 (s, 3H), 1.59 (br, 2H+water), 0.74 (d, 3H).

Step B: 5-(4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3-methylphenyl)-1,3,4-oxadiazol-2(3H)-one A solution of 4-{5-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-6-methoxypyridin-3-yl}-3-methylbenzohydrazide (Step A, 108 mg, 0.147 mmol) in THF (1.5 mL) was treated with N,N-carbonyldiimidazole (71.6 mg, 0.442 mmol). The reaction was stirred at room temperature overnight. The reaction was purified directly by silica gel chromatography, eluting with a gradient of 25-100% ethyl acetate/hexanes to give the titled compound. LCMS (M+H)$^+$: 760.5. $^1$H NMR (CDCl$_3$, 500 MHz): δ 9.08 (br, 1H), 8.22 (d, 1H), 8.18 (s, 1H), 7.89 (s, 1H), 7.78 (s, 1H), 7.74 (s, s, 3H), 7.49 (d, 1H), 7.36 (d, 1H), 5.68 (d, 1H), 5.51 (m, 0.5H), 5.40 (m, 0.5H), 4.73 (d, 1H), 4.47 (m, 3H), 4.31 (m, 2H), 4.01 (m, s, 4H), 2.38 (s, 3H), 0.76 (d, 3H). RTA IC$_{50}$: 12 nM.

Example 39

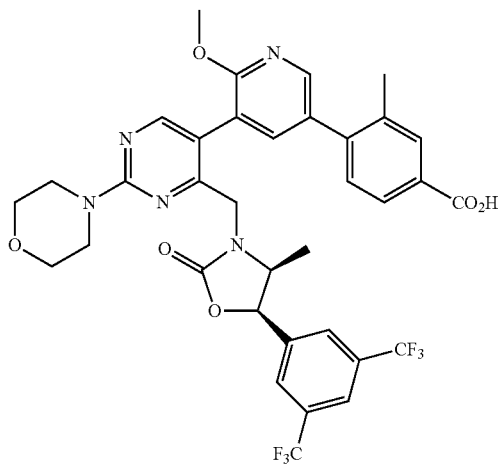 [SMILES: COc1ncc(-c2ccc(C(=O)O)cc2C)cc1-c1cnc(N2CCOCC2)nc1CN1C(=O)O[C@H](c2cc(C(F)(F)F)cc(C(F)(F)F)c2)[C@@H]1C]

4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3-methylbenzoic acid Step A: Methyl 4-{5-[4-({(4S,5R)-5-[3,5-bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3-methylbenzoate Morpholine (207 μl, 2.369 mmol), methyl 4-{5-[4-({(4S,5R)-5-[3,5-bis(trifluoromethyl)phenyl]-4- methyl-2-oxo-1, 3-oxazolidin-3-yl}methyl)-2-(methylsulfonyl)pyrimidin-5-yl]-6-methoxypyridin-3-yl}-3-methylbenzoate (INTERMEDIATE 46, 350 mg, 0.474 mmol), and THF (2.4 mL) were stirred at 100° C. for 10 minutes in the microwave reactor, at which time LCMS shows complete conversion to target. The reaction was partitioned between water and ethyl acetate. The organic was then washed with brine, dried over sodium sulfate, filtered and evaporated. The crude isolate was purified by silica gel chromatography, eluting with 25-100% ethyl acetate/hexanes to give the titled compound. $^1$H NMR (CDCl$_3$, 500 MHz): δ 8.20 (d, 1H), 8.18 (s, 1H), 7.98 (s, 1H), 7.92 (d, 1H), 7.88 (s, 1H), 7.72 (s, 2H), 7.46 (d, 1H), 7.31 (d, 1H), 5.63 (d, 1H), 4.74 (d, 1H), 4.31 (m, 1H), 4.00 (m, s, 4H), 3.94 (s, 3H), 3.86 (m, 4H), 3.80 (m, 4H), 2.37 (s, 3H), 0.72 (d, 3H).

Step B: 4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3-methylbenzoic acid Methyl 4-{5-[4-({(4S,5R)-5-[3,5-bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3-methylbenzoate (Step A, 200 mg, 0.268 mmol) was dissolved in 1,4-dioxane (5.0 mL). Lithium hydroxide (0.5M, 2.4 mL, 1.20 mmol) was added, and the reaction was stirred at room temperature for 2 hours. The reaction was quenched by adding 1.20 mL of 1N HCl, followed by water. The aqueous reaction mixture was extracted with ethyl acetate, then dried over sodium sulfate, filtered and evaporated. Purified on BIOTAGE SNAP C$_{18}$ column, eluting with 40-100% CH$_3$CN/water (0.05% TFA) and recovering purified fractions by partitioning them between pH 7 phosphate buffer and ethyl acetate. Extracted the aqueous a second time with ethyl acetate, then washed the combined organics with pH 7.0 buffer and brine. The organic was dried over sodium sulfate, filtered and evaporated to give the titled compound. LCMS (M+H)$^+$: 732.5. $^1$H NMR (CDCl$_3$, 500 MHz): δ 8.22 (d, 1H), 8.20 (s, 1H), 8.03 (s, 1H), 7.99 (d, 1H), 7.88 (s, 1H), 7.72 (s, 2H), 7.48 (d, 1H), 7.35 (d, 1H), 5.64 (d, 1H), 4.76 (d, 1H), 4.32 (m, 1H), 4.00 (m, s, 4H), 3.86 (m, 4H), 3.81 (m, 4H), 2.39 (s, 3H), 0.72 (d, 3H). RTA IC$_{50}$: 13 nM.

Example 40

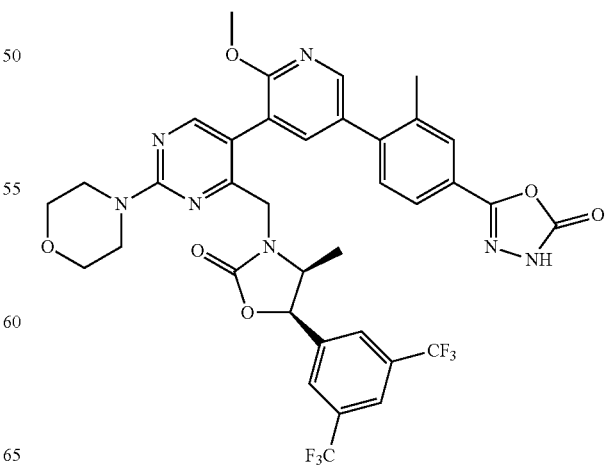

5-(4-{5-[4-({(4S,5R)-5-[3,5-Bis(trifluoromethyl) phenyl]-4-methyl-2-oxo-1,3-oxazolidin-3-yl}methyl)-2-(morpholin-4-yl)pyrimidin-5-yl]-6-methoxypyridin-3-yl}-3-methylphenyl)-1,3,4-oxadiazol-2(3H)-one Step A: 4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3-methylbenzohydrazide Methyl 4-{5-[4-({(4S,5R)-5-[3,5-bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3-methylbenzoate (EXAMPLE 39 Step A, 0.114 g, 0.153 mmol) was dissolved in ethanol (1.0 mL). Added hydrazine (0.144 mL, 4.59 mmol), and stirred at 85° C. in a screw cap vial (Pressure type) under a nitrogen blanket. Once complete, the solvent was removed by rotary evaporation and the crude isolate was partitioned between ethyl acetate and water. Washed the organic twice more with water, then once with brine, dried over sodium sulfate, filtered and evaporated to give an off-white foam as the product. The compound was used without further purification. $^1$H NMR (CDCl$_3$, 500 MHz): δ 8.18 (m, 2H), 7.88 (s, 1H), 7.71 (m, 3H), 7.61 (d, 1H), 7.45 (d, 1H), 7.35 (s, 1H), 7.31 (d, 1H), 5.63 (d, 1H), 4.74 (d, 1H), 4.33 (m, 1H), 4.10 (m, 2H), 4.00 (m, s, 4H), 3.86 (m, 4H), 3.80 (m, 4H), 2.37 (s, 3H), 0.72 (d, 3H).

Step B: 5-(4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3-methylphenyl)-1,3,4-oxadiazol-2(3H)-one 4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3-methylbenzohydrazide (Step A, 108 mg, 0.145 mmol) was dissolved in THF (1.5 mL) and treated with N,N-carbonyldiimidazole (70.5 mg, 0.435 mmol). The reaction was stirred at room temperature overnight. The reaction was purified directly by silica gel chromatography, eluting with a gradient of 25-100% ethyl acetate/hexanes to give the title compound. LCMS (M+H)$^+$: 772.5. $^1$H NMR (CDCl$_3$, 500 MHz): δ 9.09 (s, 1H), 8.22 (m, 2H), 7.88 (s, 1H), 7.78 (s, 1H), 7.72 (s+d, 3H), 7.48 (d, 1H), 7.35 (d, 1H), 5.63 (d, 1H), 4.75 (d, 1H), 4.33 (m, 1H), 4.01 (m, s, 4H), 3.86 (m, 4H), 3.81 (m, 4H), 2.38 (s, 3H), 0.73 (d, 3H). RTA IC$_{50}$: 29 nM.

Example 41

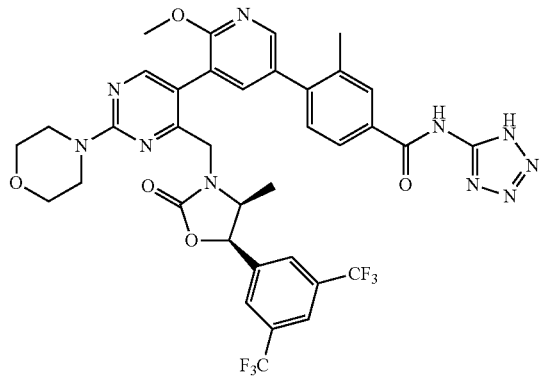 [SMILES: COc1ncc(-c2ccc(C(=O)Nc3nnn[nH]3)cc2C)cc1-c1cnc(N2CCOCC2)nc1CN1C(=O)O[C@H](c2cc(C(F)(F)F)cc(C(F)(F)F)c2)[C@@H]1C]

4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3-methyl-N-(1H-tetrazol-5-yl)benzamide To a solution of 4-{5-[4-({(4S,5R)-5-[3,5-bis(trifluoromethyl)phenyl]-4-methyl-2-oxo-1,3-oxazolidin-3-yl}methyl)-2-(morpholin-4-yl)pyrimidin-5-yl]-6-methoxypyridin-3-yl}-3-methylbenzoic acid (EXAMPLE 39, 195 mg, 0.276 mmol), EDC (106 mg, 0.55 mmol), HOBt (56 mg, 0.42 mmol), and DIEA (96 μl, 0.55 mmol) in DMF (2 mL) was added 5-aminotetrazole monohydrate (144 mg, 1.38 mmol). After stirring at 40° C. for 8 hours, the reaction mixture was directly applied to reverse phase HPLC, eluting with 10% to 100% acetonitrile in water, to obtain the title compound (160 mg, 57% yield), as a white solid after lyophilization. LCMS (M+H)$^+$: 799.1. $^1$H NMR (DMSO-d6, 500 MHz): δ 12.44 (s, 1H), 8.31 (s, 1H), 8.28 (d, J=2.5 Hz, 1H), 8.13 (s, 1H), 8.08 (s, 1H), 7.99 (m, 1H), 7.98 (s, 2H), 7.82 (d, J=2.0 Hz, 1H), 7.50 (d, J=8.0 Hz, 1H), 5.89 (d, J=8.5 Hz, 1H), 4.54 (d, J=17.0 Hz, 1H), 4.34 (m, 1H), 4.05 (d, J=17.0 Hz, 1H), 3.93 (s, 3H), 3.76 (m, 4H), 3.70 (m, 4H), 2.40 (s, 3H), 0.62 (d, J=6.5 Hz, 3H). RTA IC$_{50}$: 11 nM Example 42

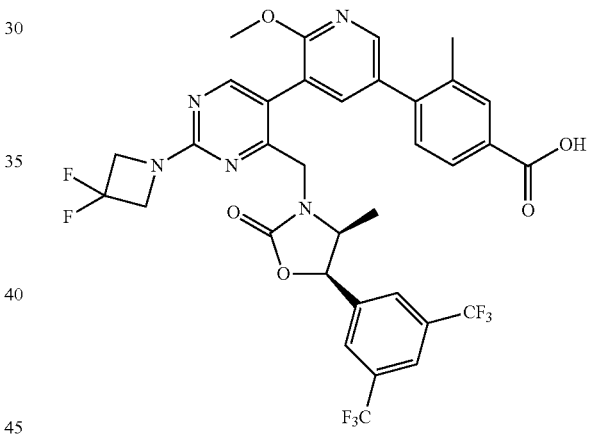

4-{5-[4-({(4S,5R)-5-[3,5-Bis(trifluoromethyl)phenyl]-4-methyl-2-oxo-1,3-oxazolidin-3-yl}methyl)-2-(3,3-difluoroazetidin-1-yl)pyrimidin-5-yl]-6-methoxypyridin-3-yl}-3-methylbenzoic acid Step A: tert-Butyl 4-{5-[4-({(4S,5R)-5-[3,5-bis(trifluoromethyl)phenyl]-4-methyl-2-oxo-1,3-oxazolidin-3-yl}methyl)-2-(3,3-difluoroazetidin-1-yl)pyrimidin-5-yl]-6-methoxypyridin-3-yl}-3-methylbenzoate A solution of (4S,5R)-5-[3,5-bis(trifluoromethyl)phenyl]-3-{[5-bromo-2-(3,3-difluoroazetidin-1-yl)pyrimidin-4-yl]methyl}-4-methyl-1,3-oxazolidin-2-one (INTERMEDIATE 13, 200 mg, 0.348 mmol), tert-butyl 4-[6-methoxy-5-(4,4,5,5-tetramethyl-1,3,2-dioxaborolan-2-yl)pyridin-3-yl]-3-methylbenzoate (INTERMEDIATE 31, 173 mg, 0.452 mmol) and potassium carbonate (144 mg, 1.04 mmol), in 1,4-dioxane (2 mL) and water (2.000 mL) was degassed, and refilled with nitrogen. Then, 1,1'-bis(di-tert-butylphosphino)ferrocene palladium dichloride (11.3 mg, 0.017 mmol) was added, and the reaction was stirred at 45° C. for 2 hours. It was directly applied to preparative reverse phase HPLC, eluting with 10% to 100% acetonitrile in water, to give the title compound for step A as a white solid after lyophilization. LCMS (M+H)+: 794.05.

Step B: 4-{5-[4-({(4S,5R)-5-[3,5-Bis(trifluoromethyl)phenyl]-4-methyl-2-oxo-1,3-oxazolidin-3-yl}methyl)-2-(3,3-difluoroazetidin-1-yl)pyrimidin-5-yl]-6-methoxypyridin-3-yl}-3-methylbenzoic acid tert-Butyl 4-{5-[4-({(4S,5R)-5-[3,5-bis(trifluoromethyl)phenyl]-4-methyl-2-oxo-1,3-oxazolidin-3-yl}methyl)-2-(3,3-difluoroazetidin-1-yl)pyrimidin-5-yl]-6-methoxypyridin-3-yl}-3-methylbenzoate (Step A, 639 mg, 0.805 mmol) was treated with 20 mL of a mixture of dichloromethane and trifluoroacetic acid (2 to 1 by volume) at room temperature for 0.5 hour, and purified on reverse phase HPLC to give the title compound as a white solid, after lyophilization. LCMS (M+H)+: 738.0. $^1$H NMR (CD$_3$OD, 500 MHz): δ 8.26 (s, 1H), 8.22 (d, J=2.0 Hz, 1H), 8.00 (s, 1H), 7.96 (s, 1H), 7.93 (s, 2H), 7.90 (dd, J=1.5 Hz, 8.0 Hz, 1H), 7.71 (d, J=2.5 Hz, 1H), 7.38 (d, J=8.0 Hz, 1H), 5.87 (d, J=9.0 Hz, 1H), 4.69 (d, J=16.0 Hz, 1H), 4.45 (m, 4H), 4.43 (m, 1H), 4.15 (d, J=16.0 Hz, 1H), 4.00 (s, 3H), 2.38 (s, 3H), 0.73 (d, J=6.5 Hz, 3H). RTA IC$_{50}$: 9 nM Example 43

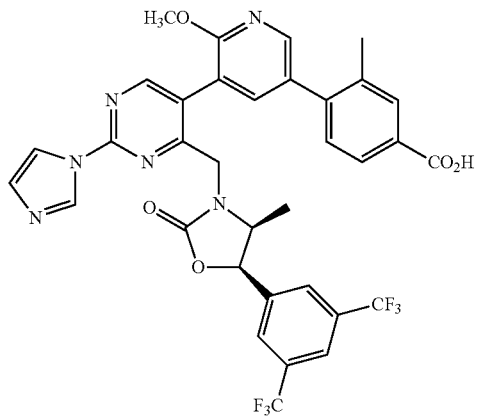 [SMILES: COc1ncc(-c2ccc(C(=O)O)cc2C)cc1-c1cnc(-n2ccnc2)nc1CN1C(=O)O[C@H](c2cc(C(F)(F)F)cc(C(F)(F)F)c2)[C@@H]1C]

4-{5-[4-({(4S,5R)-5-[3,5-Bis(trifluoromethyl)phenyl]-4-methyl-2-oxo-1,3-oxazolidin-3-yl}methyl)-2-(1H-imidazol-1-yl)pyrimidin-5-yl]-6-methoxypyridin-3-yl}-3-methylbenzoic acid Step A: Methyl 4-{5-[4-({(4S,5R)-5-[3,5-bis(trifluoromethyl)phenyl]-4-methyl-2-oxo-1,3-oxazolidin-3-yl}methyl)-2-(1H-imidazol-1-yl)pyrimidin-5-yl]-6-methoxypyridin-3-yl}-3-methylbenzoate Methyl 4-{5-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3-methylbenzoate (INTERMEDIATE 46, 125 mg, 0.169 mmol), 1,4-dioxane (1.1 mL) and imidazole (57.6 mg, 0.846 mmol) were stirred at 80° C. for 20 minutes in a 1 dram vial. LCMS shows about 2/3 conversion to target. Dropped temperature to 40° C., and stirred overnight, at which time LCMS showed reaction is complete. The reaction was directly purified by silica gel chromatography, eluting with 20-100% ethyl acetate/hexanes to give the titled compound. $^1$H NMR (CDCl$_3$, 500 MHz): δ 8.64 (s, 1H), 8.56 (s, 1H), 8.30 (d, 1H), 8.00 (s, 1H), 7.94 (d, 1H), 7.90 (s, 2H), 7.75 (s, 2H), 7.57 (d, 1H), 7.33 (d, 1H), 7.22 (s, 1H), 5.75 (d, 1H), 4.91 (d, 1H), 4.46 (m, 1H), 4.20 (d, 1H), 4.03 (s, 3H), 3.94 (s, 3H), 2.39 (s, 3H), 0.81 (d, 3H).

Step B: 4-{5-[4-({(4S,5R)-5-[3,5-Bis(trifluoromethyl)phenyl]-4-methyl-2-oxo-1,3-oxazolidin-3-yl}methyl)-2-(1H-imidazol-1-yl)pyrimidin-5-yl]-6-methoxypyridin-3-yl}-3-methylbenzoic acid Methyl 4-{5-[4-({(4S,5R)-5-[3,5-bis(trifluoromethyl)phenyl]-4-methyl-2-oxo-1,3-oxazolidin-3-yl}methyl)-2-(1H-imidazol-1-yl)pyrimidin-5-yl]-6-methoxypyridin-3-yl}-3-methylbenzoate (Step A, 99 mg, 0.136 mmol) was dissolved in 1,4-dioxane (2.4 mL). Added 0.5N LiOH (1.20 mL, 0.600 mmol), and stirred at room temperature for 2.5 hrs, at which time LCMS indicates the reaction was complete, but not clean. The reaction was quenched with 0.6 mL of 1N HCl, then diluted with pH 7 buffer and extracted twice with ethyl acetate. The organic was washed again with buffer, dried over sodium sulfate filtered and the filtrate evaporated. The crude was taken up in 1.5-2 mL of acetonitrile, and after about 15 minutes white solid came out of solution. The suspension was filtered and a second crystallization set up from the mother liquor. The combined solid recovery was 51 mg of ≥95% pure product. LCMS (M+H)+: 713.1. $^1$H NMR (CDCl$_3$, 500 MHz): δ 8.75 (br s, 1H), 8.57 (s, 1H), 8.32 (d, 1H), 8.04 (s, 1H), 7.99 (d, 1H), 7.93 (br s, 1H), 7.90 (s, 1H), 7.77 (s, 2H), 7.59 (d, 1H), 7.36 (d, 1H), 7.26 (s, 1H, (under CHCl3)), 5.82 (d, 1H), 4.93 (d, 1H), 4.48 (m, 1H), 4.21 (d, 1H), 4.04 (s, 3H), 2.40 (s, 3H), 0.81 (d, 3H). RTA IC$_{50}$: 109 nM Example 44

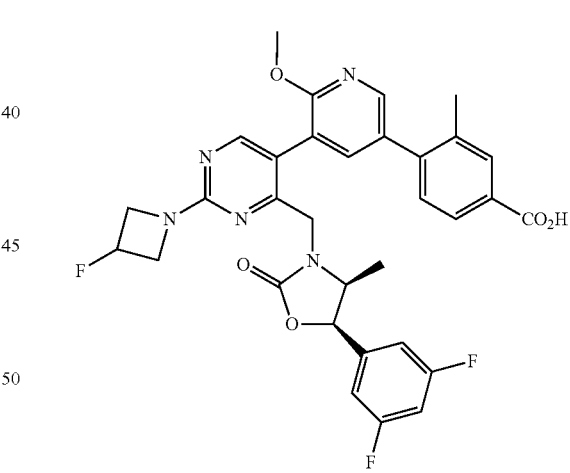

4-{5-[4-{[(4S,5R)-5-(3,5-Difluorophenyl)-4-methyl-2-oxo-1,3-oxazolidin-3-yl]methyl}-2-(3-fluoroazetidin-1-yl)pyrimidin-5-yl]-6-methoxypyridin-3-yl}-3-methylbenzoic acid Step A: Methyl 4-{5-[4-{[(4S,5R)-5-(3,5-difluorophenyl)-4-methyl-2-oxo-1,3-oxazolidin-3-yl]methyl}-2-(3-fluoroazetidin-1-yl)pyrimidin-5-yl]-6-methoxypyridin-3-yl}-3-methylbenzoate A 10 mL flask charged with (4S,5R)-3-{[5-(5-chloro-2-methoxypyridin-3-yl)-2-(3-fluoroazetidin-1-yl)pyrimidin-4- yl]methyl}-5-(3,5-difluorophenyl)-4-methyl-1,3-oxazolidin-2-one (EXAMPLE 13, 0.055 g, 0.106 mmol), methyl 3-methyl-4-(4,4,5,5-tetramethyl-1,3,2-dioxaboran-2-yl)benzoate (0.044 g, 0.159 mmol) and (2-dicyclohexylphosphino-2',4',6'-triisopropyl-1,1'-biphenyl)[2-(2-aminoethyl)phenyl)] palladium(II) chloride (XPHOS Biphenyl Precatalyst) (8.32 mg, 10.58 µmol) was evacuated and charged with nitrogen. Added 1,4-dioxane (0.705 mL) and 2N tribasic potassium phosphate (0.159 mL, 0.317 mmol), degassed, added nitrogen, then stirred at 80° C. for 1 hour. LCMS shows significant amounts of product. The reaction was purified directly by silica gel chromatography, eluting with 5-65% ethyl acetate/hexanes to give the title compound. $^1$H NMR (CDCl$_3$, 500 MHz): δ 8.20 (d, 1H), 8.16 (s, 1H), 7.98 (s, 1H), 7.92 (d, 1H), 7.46 (d, 1H), 7.31 (d, 1H), 6.82 (m, 3H), 5.51 (d, 1.5H), 5.40 (m, 0.5H), 4.67 (d, 1H), 4.47 (m, 2H), 4.30 (m, 3H), 4.00 (d, s, 4H), 3.93 (s, 3H), 2.37 (s, 3H), 0.77 (d, 3H).

Step B: 4-{5-[4-{[(4S,5R)-5-(3,5-Difluorophenyl)-4-methyl-2-oxo-1,3-oxazolidin-3-yl]methyl}-2-(3-fluoroazetidin-1-yl)pyrimidin-5-yl]-6-methoxypyridin-3-yl}-3-methylbenzoic acid Methyl 4-{5-[4-{[(4S,5R)-5-(3,5-difluorophenyl)-4-methyl-2-oxo-1,3-oxazolidin-3-yl]methyl}-2-(3-fluoroazetidin-1-yl)pyrimidin-5-yl]-6-methoxypyridin-3-yl}-3-methylbenzoate (Step A, 65 mg, 0.103 mmol) was dissolved in 1,4-dioxane (2 mL). Added 0.5N lithium hydroxide (1.0 mL, 0.50 mmol) and stirred at room temperature for 2.5 hours at which time LCMS shows complete hydrolysis. The reaction was quenched by adding 0.50 mL of 1N HCl, followed by water. The reaction was extracted with ethyl acetate. The ethyl acetate layer was dried over sodium sulfate, filtered and evaporated. The crude isolate was purified on a BIOTAGE SNAP C$_{18}$ column, eluting with 40-100% CH$_3$CN/water (0.05% TFA). The purified fractions were partitioned between pH 7 phosphate buffer and ethyl acetate. The aqueous was extracted a second time with ethyl acetate, then washed with pH 7.0 buffer and brine. The organic was dried over sodium sulfate, filtered and evaporated to give the title compound. LCMS (M+H)$^+$: 620.2. $^1$H NMR (CDCl$_3$, 500 MHz): δ 8.21 (br, 1H), 8.20 (s, 1H), 8.02 (s, 1H), 7.97 (d, 1H), 7.47 (s, 1H), 7.33 (d, 1H), 6.81 (m, 3H), 5.50 (d, 1.5H), 5.40 (m, 0.5H), 4.69 (d, 1H), 4.47 (m, 2H), 4.33 (m, 3H), 4.00 (d, s, 4H), 2.38 (s, 3H), 0.76 (d, 3H). RTA IC$_{50}$: 35 nM Example 45

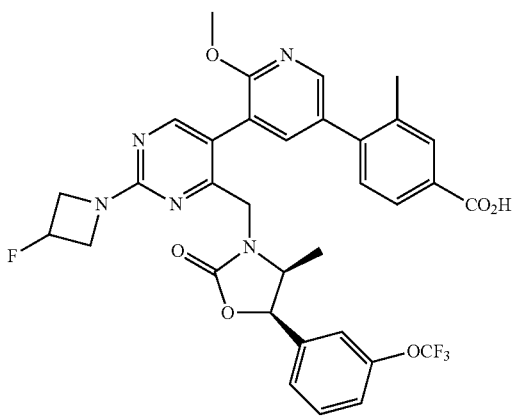 [SMILES: COc1ncc(-c2ccc(C(=O)O)cc2C)cc1-c1cnc(N2CC(F)C2)nc1CN1C(=O)O[C@H](c2cccc(OC(F)(F)F)c2)[C@@H]1C]

4-{5-[2-(3-Fluoroazetidin-1-yl)-4-({(4S,5R)-4-methyl-2-oxo-5-[3-(trifluoromethoxy)phenyl]-1,3-oxazolidin-3-yl}methyl)pyrimidin-5-yl]-6-methoxypyridin-3-yl}-3-methylbenzoic acid Step A: Methyl 4-{5-[2-(3-fluoroazetidin-1-yl)-4-({(4S,5R)-4-methyl-2-oxo-5-[3-(trifluoromethoxy)phenyl]-1,3-oxazolidin-3-yl}methyl)pyrimidin-5-yl]-6-methoxypyridin-3-yl}-3-methylbenzoate A 10 mL flask charged with (4S,5R)-3-{[5-(5-chloro-2-methoxypyridin-3-yl)-2-(3-fluoroazetidin-1-yl)pyrimidin-4-yl]methyl}-4-methyl-5-[3-(trifluoromethoxy)phenyl]-1,3-oxazolidin-2-one (INTERMEDIATE 20, 0.040 g, 0.070 mmol), methyl 3-methyl-4-(4,4,5,5-tetramethyl-1,3,2-dioxaboran-2-yl)benzoate (0.029 g, 0.106 mmol) and (2-dicyclohexyl phosphino-2',4',6'-triisopropyl-1,1'-biphenyl)[2-(2-aminoethyl)phenyl)]palladium(II) chloride (XPHOS Biphenyl Precatalyst) (5.5 mg, 7.04 µmol) was evacuated and charged with nitrogen. Added 1,4-dioxane (0.470 mL) and 2N tribasic potassium phosphate (0.106 mL, 0.211 mmol), degassed, added nitrogen, then stirred at 80° C. for 1 hour. LCMS shows significant amounts of product. The reaction was purified directly by silica gel chromatography, eluting with 5-50% ethyl acetate/hexanes to give the title compound. $^1$H NMR (CDCl$_3$, 500 MHz): δ 8.20 (d, 1H), 8.16 (s, 1H), 7.98 (s, 1H), 7.92 (d, 1H), 7.46 (d, 1H), 7.41 (t, 1H), 7.32 (d, 1H), 7.21 (m, 2H), 7.13 (s, 1H), 5.55 (d, 1H), 5.51 (m, 0.5H), 5.40 (m, 0.5H), 4.69 (d, 1H), 4.48 (m, 2H), 4.30 (m, 3H), 4.00 (d, s, 4H), 3.93 (s, 3H), 2.37 (s, 3H), 0.73 (d, 3H).

Step B: 4-{5-[2-(3-Fluoroazetidin-1-yl)-4-({(4S,5R)-4-methyl-2-oxo-5-[3-(trifluoromethoxy)phenyl]-1,3-oxazolidin-3-yl}methyl)pyrimidin-5-yl]-6-methoxypyridin-3-yl}-3-methylbenzoic acid Methyl 4-{5-[2-(3-fluoroazetidin-1-yl)-4-({(4S,5R)-4-methyl-2-oxo-5-[3-(trifluoromethoxy)phenyl]-1,3-oxazolidin-3-yl}methyl)pyrimidin-5-yl]-6-methoxypyridin-3-yl}-3-methylbenzoate (31.4 mg, 0.046 mmol) was dissolved in 1,4-dioxane (2 mL). Added 0.5N lithium hydroxide (0.50 mL, 0.25 mmol) and stirred at room temperature for 2.5 hours at which time LCMS shows complete hydrolysis. The reaction was quenched by adding 0.25 mL of 1N HCl, followed by water. The reaction was extracted with ethyl acetate. The ethyl acetate layer was dried over sodium sulfate, filtered and evaporated. The crude isolate was purified on a BIOTAGE SNAP C$_{18}$ column, eluting with 40-100% CH$_3$CN/water (0.05% TFA). The purified fractions were partitioned between pH 7 phosphate buffer and ethyl acetate. The aqueous was extracted a second time with ethyl acetate, then washed with pH 7.0 buffer and brine. The organic was dried over sodium sulfate, filtered and evaporated to give the title compound. LCMS (M+H)$^+$: 668.2. $^1$H NMR (CDCl$_3$, 500 MHz): δ 8.21 (br, 1H), 8.18 (s, 1H), 8.02 (s, 1H), 7.97 (br d, 1H), 7.47 (s, 1H), 7.41 (t, 1H), 7.33 (m, 1H), 7.21 (m, 2H), 7.13 (s, 1H), 5.55 (d, 1H), 5.51 (m, 0.5H), 5.40 (m, 0.5H), 4.71 (d, 1H), 4.48 (m, 2H), 4.30 (m, 3H), 4.00 (d, s, 4H), 2.37 (s, 3H), 0.73 (d, 3H). RTA IC$_{50}$: 50 nM Example 46

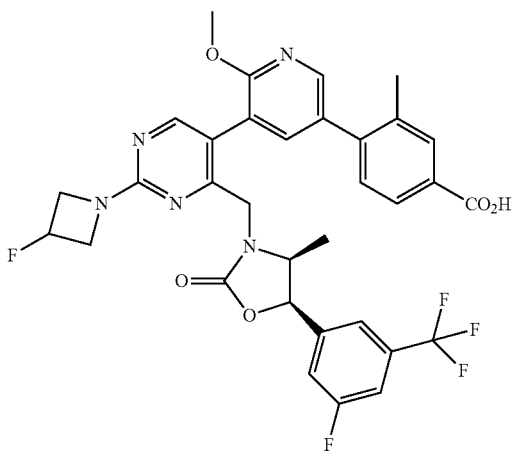 [SMILES: COc1ncc(-c2ccc(C(=O)O)cc2C)cc1-c1cnc(N2CC(F)C2)nc1CN1C(=O)O[C@H](c2cc(F)cc(C(F)(F)F)c2)[C@@H]1C]

4-{5-[2-(3-Fluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3-methylbenzoic acid Step A: tert-Butyl 4-{5-[2-(3-fluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3-methylbenzoate To a solution of tert-butyl 4-{5-[4-({(4S,5R)-5-[3-fluoro-5-(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3-methylbenzoate (INTERMEDIATE 48, 96 mg, 0.131 mmol) in THF (1.5 mL) was added 3-fluoroazetidine hydrochloride (44 mg, 0.394 mmol) and triethylamine (0.082 mL, 0.591 mmol). The resulting mixture was subjected to microwave irradiation at 120° C. for 20 minutes. The reaction mixture was diluted with ethyl acetate, washed with water, brine, dried (sodium sulfate), filtered and concentrated to give crude tert-butyl 4-{5-[2-(3-fluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3-methylbenzoate (95 mg, 0.131 mmol). LCMS (M+H)$^+$: 726.2.

Step B: 4-{5-[2-(3-Fluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3-methylbenzoic acid To a 0° C. solution of tert-butyl 4-{5-[2-(3-fluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3-methylbenzoate (Step A, 95 mg, 0.131 mmol) in dichloromethane (0.700 mL) was added TFA (0.700 mL). The ice bath was removed, and the reaction mixture was stirred for 1 hour. Upon completion, the solvent was removed under reduced pressure, and the resultant residue was dissolved in acetonitrile:water (1:1) for direct purification by reverse phase HPLC (C$_{18}$) followed by lyophilization of appropriate fractions to yield 4-{5-[2-(3-fluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3-methylbenzoic acid (62 mg, 0.078 mmol) as a white fluffy solid. LCMS (M+H)$^+$: 670.2. $^1$H NMR (500 MHz, CD$_3$OD): δ 8.22 (m, 2H), 7.98 (s, 1H), 7.91 (d, 1H, J=8.7 Hz), 7.70 (s, 1H), 7.50 (m, 2H), 7.40 (m, 2H), 5.76 (d, 1H, J=8.7 Hz), 5.54 (br s, 0.5H), 5.43 (br s, 0.5H), 4.62 (d, 1H, J=17.1 Hz), 4.50 (m, 2H), 4.40 (m, 1H), 4.24 (m, 2H), 4.14 (d, 1H, J=17.0 Hz), 4.02 (s, 3H), 2.39 (s, 3H), 0.75 (d, 3H, J=6.5 Hz). RTA IC$_{50}$: 12 nM.

Example 47

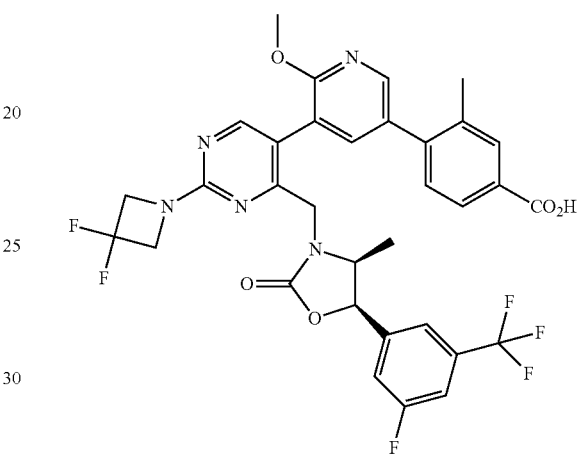

4-{5-[2-(3,3-Difluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3-methylbenzoic acid Step A: tert-Butyl 4-{5-[2-(3,3-difluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3-methylbenzoate To a solution of tert-butyl 4-{5-[4-({(4S,5R)-5-[3-fluoro-5-(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3-methylbenzoate (INTERMEDIATE 48, 96 mg, 0.131 mmol) in THF (1.5 mL) was added 3,3-difluoroazetidine hydrochloride (51.1 mg, 0.394 mmol) and triethylamine (0.082 mL, 0.591 mmol). The resulting mixture was subjected to microwave irradiation at 135° C. for 40 minutes. The reaction mixture was diluted with ethyl acetate, washed with water, brine, dried (sodium sulfate), filtered and concentrated to give crude tert-butyl 4-{5-[2-(3,3-difluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3-methylbenzoate (98 mg, 0.131 mmol). LCMS (M+H)$^+$: 744.2.

Step B: 4-{5-[2-(3,3-Difluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3-methylbenzoic acid To a solution of tert-butyl 4-{5-[2-(3,3-difluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3-methylbenzoate (Step A, 98 mg, 0.132 mmol) in dichloromethane (0.700 mL), cooled to 0° C. was added TFA (0.700 mL). The ice bath was removed and the reaction mixture was stirred for 1 hour. Upon completion the solvent was removed under reduced pressure and the resultant residue was dissolved in acetonitrile:water (1:1) for direct purification by reverse phase HPLC ($C_{18}$) followed by lyophilization of appropriate fractions to yield 4-{5-[2-(3,3-difluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3-methylbenzoic acid (50.4 mg, 0.063 mmol) as a white fluffy solid. LCMS (M+H)$^+$: 688.1. $^1$H NMR (500 MHz, CD$_3$OD) δ 8.27 (s, 1H), 8.23 (s, 1H), 7.97 (s, 1H), 7.91 (d, 1H, J=7.8 Hz), 7.71 (s, 1H), 7.50 (m, 2H), 7.39 (m, 2H), 5.76 (d, 1H, J=8.6 Hz), 4.67 (d, 1H, J=17.0 Hz), 4.53 (m, 4H), 4.38 (m, 1H), 4.16 (d, 1H, J=17.0 Hz), 4.01 (s, 3H), 2.39 (s, 3H), 0.75 (d, 3H, J=6.5 Hz). RTA IC$_{50}$: 9 nM.

Example 48

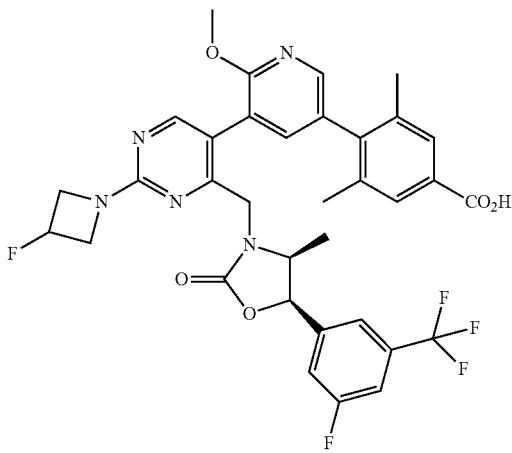 [SMILES: COc1ncc(-c2c(C)cc(C(=O)O)cc2C)cc1-c1cnc(N2CC(F)C2)nc1CN1C(=O)O[C@H](c2cc(F)cc(C(F)(F)F)c2)[C@@H]1C]

4-{5-[2-(3-Fluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3,5-dimethylbenzoic acid Step A: Methyl 4-{5-[2-(3-fluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3,5-dimethylbenzoate To a solution of methyl 4-{5-[4-({(4S,5R)-5-[3-fluoro-5-(trifluoromethyl)phenyl]-4-methyl-2-oxo-1,3-oxazolidin-3-yl}methyl)-2-(methylsulfonyl)pyrimidin-5-yl]-6-methoxypyridin-3-yl}-3,5-dimethylbenzoate (INTERMEDIATE 50, 82 mg, 0.117 mmol) in THF (1.5 mL) was added 3-fluoroazetidine hydrochloride (39.2 mg, 0.351 mmol) and triethylamine (0.074 mL, 0.5927 mmol). The resulting mixture was subjected to microwave irradiation at 120° C. for 20 minutes (BIOTAGE microwave). The reaction mixture was diluted with ethyl acetate, washed with water, brine, dried (sodium sulfate), filtered and concentrated to give crude methyl 4-{5-[2-(3-fluoroazetidin-1-yl)-4-({(4S,5R)-5-[3-fluoro-5-(trifluoromethyl)phenyl]-4-methyl-2-oxo-1,3-  oxazolidin-3-yl}methyl)pyrimidin-5-yl]-6-methoxypyridin-3-yl}-3,5-dimethylbenzoate (82 mg, 0.118 mmol). LCMS (M+H)$^+$: 698.2.

Step B: 4-{5-[2-(3-Fluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3,5-dimethylbenzoic acid To a stirred solution of methyl 4-{5-[2-(3-fluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3,5-dimethylbenzoate (Step A, 82 mg, 0.118 mmol) in dioxane (2.4 mL) was added an aqueous solution of lithium hydroxide (1.2 mL, 0.5 M). The mixture was heated at 60° C. for one hour. The reaction mixture was cooled and acidified by the addition of TFA (0.090 mL, 1.17 mmol). Volatiles were removed under reduced pressure and the residue was purified by preparative HPLC reverse phase (C-18) to give 4-{5-[2-(3-fluoroazetidin-1-yl)-4-({(4S,5R)-5-[3-fluoro-5-(trifluoromethyl)phenyl]-4-methyl-2-oxo-1,3-oxazolidin-3-yl}methyl)pyrimidin-5-yl]-6-methoxypyridin-3-yl}-3,5-dimethylbenzoic acid (60.7 mg, 0.089 mmol) as a white solid following lyophilization. LCMS (M+H)$^+$: 684.1. $^1$H NMR (500 MHz, CD$_3$OD): δ 8.19 (s, 1H), 8.03 (s, 1H), 7.80 (s, 2H), 7.50 (m, 3H), 7.40 (m, 1H), 5.80 (d, 1H, J=8.4 Hz), 5.49 (br s, 0.5H), 5.42 (br s, 0.5H), 4.64 (d, 1H, J=16.9 Hz), 4.50 (m, 2H), 4.40 (m, 1H), 4.24 (m, 2H), 4.14 (d, 1H, J=16.9 Hz), 4.02 (s, 3H) 2.17 (s, 3H), 2.16 (s, 3H), 0.76 (d, 3H, J=6.6 Hz). RTA IC$_{50}$: 15 nM.

Example 49

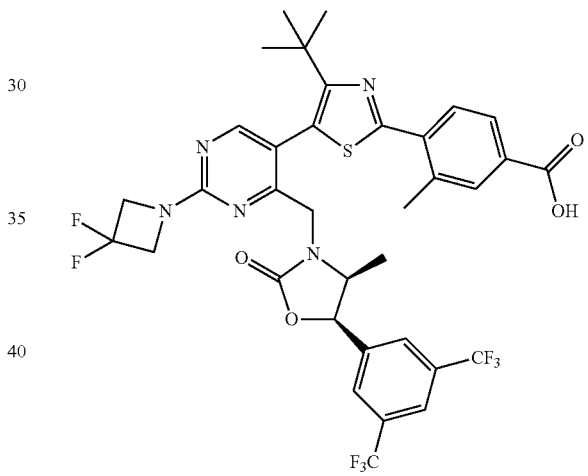

4-{5-[4-({(4S,5R)-5-[3,5-Bis(trifluoromethyl)phenyl]-4-methyl-2-oxo-1,3-oxazolidin-3-yl}methyl)-2-(3,3-difluoroazetidin-1-yl)pyrimidin-5-yl]-4-tert-butyl-1,3-thiazol-2-yl}-3-methylbenzoic acid To a solution of 4-{5-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-4-tert-butyl-1,3-thiazol-2-yl}-3-methylbenzoic acid (INTERMEDIATE 52, 80 mg, 0.106 mmol) in THF (5 mL) was added 3,3-difluoroazetidine hydrochloride (41.1 mg, 0.317 mmol) and DIEA (0.092 mL, 0.529 mmol). The reaction mixture was stirred at 60° C. for 15 minutes to see complete conversion by LCMS. The solvent was evaporated, and the residue was purified on reverse phase HPLC, eluting with water and acetonitrile (10% to 100%), to give the title compound as a yellowish solid after lyophilization (72 mg, 88% yield). LCMS (M+H)$^+$: 770.1. $^1$H NMR (CDCl$_3$, 500 MHz): δ 8.35 (s, 1H), 8.08 (s, 1H), 8.00 (s, 1H), 7.93 (s, 1H), 7.87 (m, 1H), 7.79 (s, 2H), 5.82 (d, 9.0 Hz, 1H), 5.50 (m, 1H), 4.75 (m, 1H), 4.58-4.34 (m, 4H), 4.09 (m, 1H), 3.75 (s, 3H), 1.33 (s, 9H), 0.81 (d, 7.0 Hz, 3H). RTA IC$_{50}$: 800 nM.

Example 50

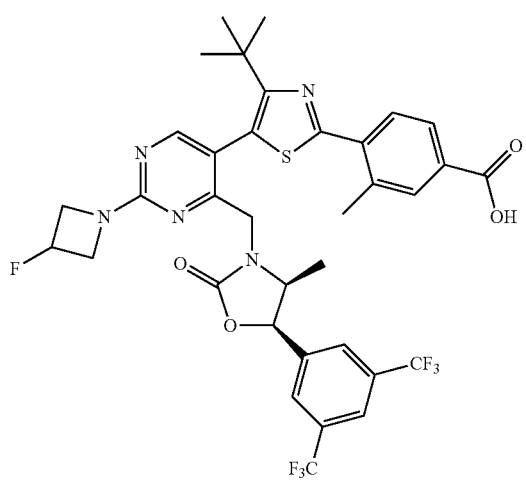 [SMILES: Cc1cc(C(=O)O)ccc1-c1nc(C(C)(C)C)c(-c2cnc(N3CC(F)C3)nc2CN2C(=O)O[C@H](c3cc(C(F)(F)F)cc(C(F)(F)F)c3)[C@@H]2C)s1]

4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-4-tert-butyl-1,3-thiazol-2-yl}-3-methylbenzoic acid To a solution of 4-{5-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-4-tert-butyl-1,3-thiazol-2-yl}-3-methylbenzoic acid (INTERMEDIATE 52, 180 mg, 0.106 mmol) in THF (5 mL) was added 3-fluoroazetidine hydrochloride (35.4 mg, 0.317 mmol) and DIEA (0.092 mL, 0.529 mmol). It was stirred at 60° C. for 15 minutes to see complete conversion by LCMS. The solvent was evaporated, and the residue was purified on reverse phase HPLC, eluting with water and acetonitrile (10% to 100%), to give the title compound as a yellowish solid after lyophilization (74 mg, 93% yield). LCMS (M+H)$^+$: 752.05. $^1$H NMR (CDCl$_3$, 500 MHz): δ 8.36 (s, 1H), 8.08 (s, 1H), 8.00 (s, 1H), 7.93 (s, 1H), 7.87 (m, 1H), 7.79 (s, 2H), 5.80 (d, 9.0 Hz, 1H), 4.75 (m, 4H), 4.61-4.53 (m, 4H), 4.47 (m, 1H), 4.09 (m, 1H), 3.76 (s, 3H), 1.33 (s, 9H), 0.82 (d, 7.0 Hz, 3H). RTA IC$_{50}$: 197 nM.

Example 51

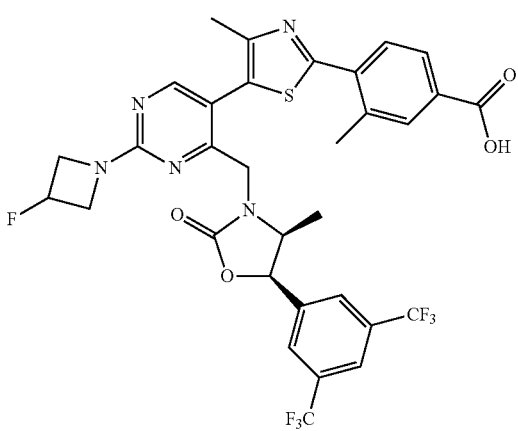 [SMILES: Cc1cc(C(=O)O)ccc1-c1nc(C)c(-c2cnc(N3CC(F)C3)nc2CN2C(=O)O[C@H](c3cc(C(F)(F)F)cc(C(F)(F)F)c3)[C@@H]2C)s1]

4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-4-methyl-1,3-thiazol-2-yl}-3-methylbenzoic acid To a solution of 4-{5-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-4-methyl-1,3-thiazol-2-yl}-3-methylbenzoic acid (INTERMEDIATE 54, 200 mg, 0.280 mmol) in THF (5 mL) was added 3-fluorazetidine hydrochloride (94 mg, 0.840 mmol) and DIEA (0.244 mL, 1.399 mmol). The reaction mixture was stirred at 60° C. for 15 minutes to see complete conversion by LCMS. The solvent was evaporated, and the residue was purified on reverse phase HPLC, eluting with 10%-100% acetonitrile in water, to give the title compound (167 mg, 84% yield) as a slightly yellow solid. LCMS (M+H)$^+$: 710.1. $^1$H NMR (CDCl$_3$, 500 MHz): δ 8.36 (s, 1H), 8.08 (s, 1H), 8.02 (d, J=8.5 Hz, 1H), 7.93 (s, 1H), 7.89 (d, J=8.5 Hz, 1H), 7.78 (s, 2H), 5.79 (d, J=8.5 Hz, 1H), 5.50 (m, 1H), 4.77 (d, J=17.0 Hz, 1H), 4.56 (m, 2H), 4.46-4.34 (m, 3H), 4.08 (d, J=17.0 Hz, 1H), 2.71 (s, 3H), 2.43 (s, 3H), 0.80 (d, J=7.0 Hz, 3H). RTA IC$_{50}$: 33 nM.

Example 52

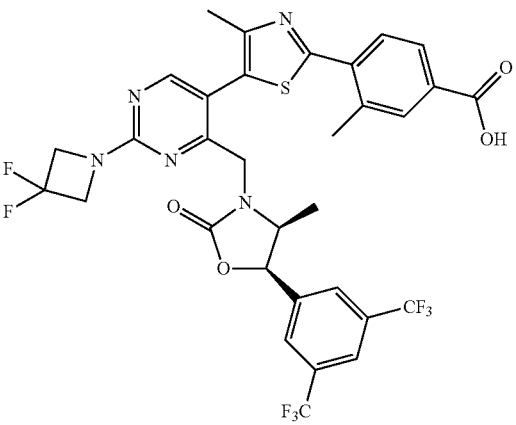 [SMILES: Cc1cc(C(=O)O)ccc1-c1nc(C)c(-c2cnc(N3CC(F)(F)C3)nc2CN2C(=O)O[C@H](c3cc(C(F)(F)F)cc(C(F)(F)F)c3)[C@@H]2C)s1]

4-{5-[4-({(4S,5R)-5-[3,5-Bis(trifluoromethyl)phenyl]-4-methyl-2-oxo-1,3-oxazolidin-3-yl}methyl)-2-(3,3-difluoroazetidin-1-yl)pyrimidin-5-yl]-4-methyl-1,3-thiazol-2-yl}-3-methylbenzoic acid To a solution of 4-{5-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-4-methyl-1,3-thiazol-2-yl}-3-methylbenzoic acid (INTERMEDIATE 54, 200 mg, 0.280 mmol) in THF (5 mL) was added 3,3-difluoroazetidine (129.5 mg, 0.840 mmol) and DIEA (0.244 mL, 1.399 mmol). The reaction mixture was stirred at 60° C. for 15 minutes to see complete conversion by LCMS. The solvent was evaporated, and the residue was purified on reverse phase HPLC, eluting with 10%-100% acetonitrile in water, to give title compound as a slightly yellow solid. LCMS (M+H)$^+$: 728.1. $^1$H NMR (CDCl$_3$, 500 MHz): δ 8.37 (s, 1H), 8.08 (s, 1H), 8.02 (d, J=8.5 Hz, 1H), 7.93 (s, 1H), 7.90 (d, J=8.5 Hz, 1H), 7.78 (s, 2H), 5.79 (d, J=8.5 Hz, 1H), 4.78 (d, J=17.0 Hz, 1H), 4.58 (m, 4H), 4.42 (m, 3H), 4.08 (d, J=17.0 Hz, 1H), 2.72 (s, 3H), 2.43 (s, 3H), 0.80 (d, J=7.0 Hz, 3H). RTA IC$_{50}$: 61 nM.

Example 53

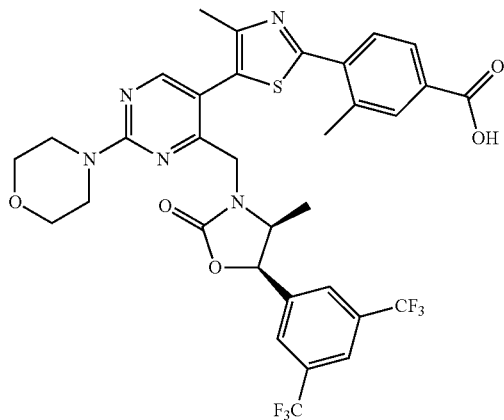 [SMILES: Cc1cc(C(=O)O)ccc1-c1nc(C)c(-c2cnc(N3CCOCC3)nc2CN2C(=O)O[C@H](c3cc(C(F)(F)F)cc(C(F)(F)F)c3)[C@@H]2C)s1]

4-{5-[4-({(4S,5R)-5-[3,5-Bis(trifluoromethyl)phenyl]-4-methyl-2-oxo-1,3-oxazolidin-3-yl}methyl)-2-(morpholin-4-yl)pyrimidin-5-yl]-4-methyl-1,3-thiazol-2-yl}-3-methylbenzoic acid To a solution of 4-{5-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-4-methyl-1,3-thiazol-2-yl}-3-methylbenzoic acid (INTERMEDIATE 54, 200 mg, 0.280 mmol) in THF (5 mL) was added morpholine (73.1 mg, 0.840 mmol) and DIEA (0.244 mL, 1.399 mmol). It was stirred at 60° C. for 15 minutes to see complete conversion by LCMS. The solvent was evaporated and the residue was purified on reverse phase HPLC, eluting with 10%-100% acetonitrile in water to give the title compound as a white solid. LCMS (M+H)⁺: 728.1. ¹H NMR (CDCl₃, 500 MHz): δ 8.33 (s, 1H), 8.08 (s, 1H), 8.02 (d, J=8.5 Hz, 1H), 7.92 (s, 1H), 7.88 (d, J=8.5 Hz, 1H), 7.77 (s, 2H), 5.75 (d, J=8.5 Hz, 1H), 4.77 (d, J=17.0 Hz, 1H), 4.36 (m, 1H), 4.086 (d, J=17.0 Hz, 1H), 3.92 (m, 4H), 3.85 (m, 4H), 2.71 (s, 3H), 2.44 (s, 3H), 0.78 (d, J=7.0 Hz, 3H). RTA IC₅₀: 82 nM.

Example 54

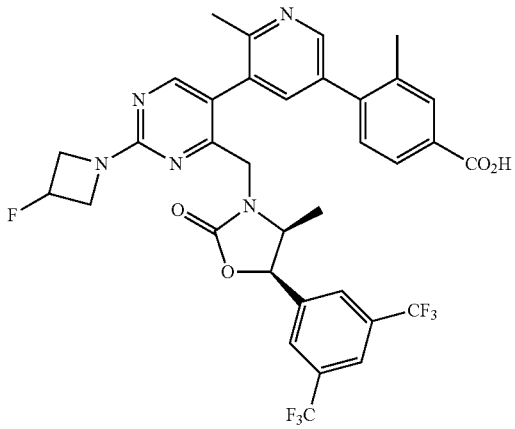 [SMILES: Cc1cc(C(=O)O)ccc1-c1cnc(C)c(-c2cnc(N3CC(F)C3)nc2CN2C(=O)O[C@H](c3cc(C(F)(F)F)cc(C(F)(F)F)c3)[C@@H]2C)c1]

4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methylpyridin-3-yl}-3-methylbenzoic acid Step A: tert-Butyl 4-{5-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-6-methylpyridin-3-yl}-3-methylbenzoate To a 10 mL microwave tube was added (4S,5R)-5-[3,5-bis(trifluoromethyl)phenyl]-3-{[2-(3-fluoroazetidin-1-yl)-5-(4,4,5,5-tetramethyl-1,3,2-dioxaborolan-2-yl)pyrimidin-4-yl]methyl}-4-methyl-1,3-oxazolidin-2-one (INTERMEDIATE 22, 86 mg, 0.142 mmol), tert-butyl 4-(5-chloro-6-methylpyridin-3-yl)-3-methylbenzoate (INTERMEDIATE 39, 41 mg, 0.129 mmol), potassium phosphate (41 mg, 0.194 mmol), (2-dicyclohexylphosphino-2',4',6'-triisopropyl-1,1'-biphenyl)[2-(2-aminoethyl)phenyl)]palladium(II) chloride (XPHOS Biphenyl Precatalyst) (20.3 mg, 0.026 mmol), followed by dioxane (2 mL) and water (0.1 mL). The tube was sealed and stirred at 180° C. in the microwave reactor for 10 minutes. After cooling down, the solvent was evaporated. The residue was purified by silica gel chromatography (0 to 100% Ethyl acetate/hexane) and afforded the title compound as a white solid in 46% yield. LCMS (M+H)⁺: 760.2.

Step B: 4-{5-[4-({(4S,5R)-5-[3,5-Bis(trifluoromethyl)phenyl]-4-methyl-2-oxo-1,3-oxazolidin-3-yl}methyl)-2-(3-fluoroazetidin-1-yl)pyrimidin-5-yl]-6-methylpyridin-3-yl}-3-methylbenzoic acid To a 25 mL round bottom flask was added tert-butyl 4-{5-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-6-methylpyridin-3-yl}-3-methylbenzoate (Step A, 40 mg, 0.053 mmol) and TFA (4 mL). The mixture was stirred at room temperature for 10 minutes. Volatiles were removed. The residue was purified on silica gel chromatography (0 to 100% acetone/hexane), affording the title compound as white solid. LCMS (M+H)⁺: 704.1. RTA IC₅₀: 26 nM.

Example 55

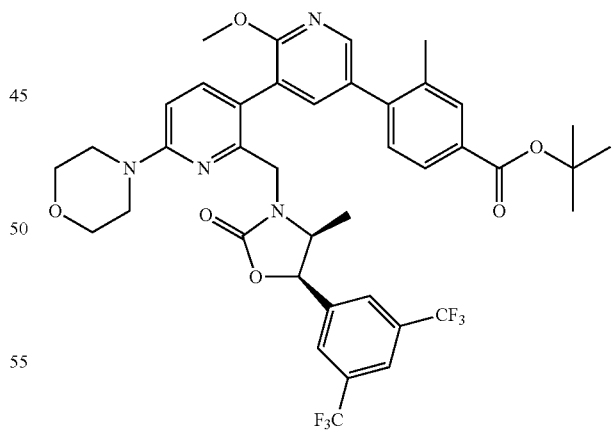

tert-Butyl 4-[2'4 {(4S,5R)-5-[3,5-bis(trifluoromethyl)phenyl]-4-methyl-2-oxo-1,3-oxazolidin-3-yl}methyl)-2-methoxy-6'-(morpholin-4-yl)-3,3'-bipyridin-5-yl]-3,5-dimethylbenzoate A mixture of (4S,5R)-5-[3,5-bis(trifluoromethyl)phenyl]-3-{[3-bromo-6-(morpholin-4-yl)pyridin-2-yl]methyl}-4-methyl-1,3-oxazolidin-2-one (INTERMEDIATE 27, 0.142 g, 0.25 mmol), tert-butyl 4-(6-methoxy-5-(4,4,5,5-tetramethyl-1,3,2-dioxaborolan-2-yl)pyridin-3-yl)-3-methylbenzoate (INTERMEDIATE 31, 0.117 g, 0.275 mmol), potassium carbonate (0.375 mL, 0.750 mmol, 2M aq.) and 1,1'-bis(di-tert-butylphoshino)ferrocene palladium dichloride (0.016 g, 0.025 mmol) in THF (1.25 mL) was de-gassed and refilled with nitrogen (3×), then was heated at 40° C. for 4 h. Monitoring by LCMS and TLC showed the reaction was complete; it was then diluted with ethyl acetate, washed with saturated aqueous $NaHCO_3$, water and brine. The organic phase was dried with $Na_2SO_4$, filtered and the filtrate concentrated. The crude was purified by silica gel chromatography, eluting with 25% ethyl acetate in hexanes to give the titled compound (0.167 g, 0.213 mmol, 85% yield) as light yellow solid. LCMS $(M+H)^+$: 787.3. $^1H$ NMR ($CDCl_3$, 500 MHz): δ 8.19 (d, 1H), 7.93 (s, 1H), 7.90 (s, 1H), 7.88 (s, 1H), 7.74 (s, 2H), 7.46 (d, 1H), 7.43 (d, 1H), 7.31 (d, 1H), 6.68 (d, 1H), 5.61 (d, 1H), 4.78-4.86 (m, 1H), 4.33-4.24 (m, 1H), 4.18-4.07 (m, 1H), 4.02 (s, 3H), 3.89-3.87 (t, 4H), 3.58-3.64 (m, 4H), 2.38 (s, 3H), 1.65 (s, 9H), 0.67 (brd, 3H). RTA $IC_{50}$: 22 nM.

Example 56

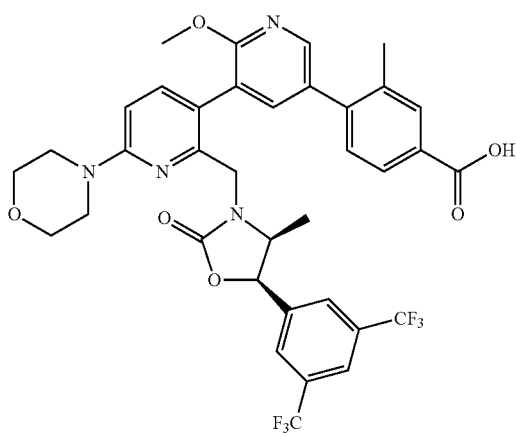 [SMILES: COc1ncc(-c2ccc(C(=O)O)cc2C)cc1-c1ccc(N2CCOCC2)nc1CN1C(=O)O[C@H](c2cc(C(F)(F)F)cc(C(F)(F)F)c2)[C@@H]1C]

4-[2'-({(4S,5R)-5-[3,5-Bis(trifluoromethyl)phenyl]-4-methyl-2-oxo-1,3-oxazolidin-3-yl}methyl)-2-methoxy-6'-(morpholin-4-yl)-3,3'-bipyridin-5-yl]-3,5-dimethylbenzoic acid A solution of TFA (0.095 mL, 1.240 mmol) and tert-butyl 4-[2'-({(4S,5R)-5-[3,5-bis(trifluoromethyl)phenyl]-4-methyl-2-oxo-1,3-oxazolidin-3-yl}methyl)-2-methoxy-6'-(morpholin-4-yl)-3,3'-bipyridin-5-yl]-3,5-dimethylbenzoate (EXAMPLE 55, 44 mg, 0.055 mmol) in $CH_2Cl_2$ (0.5 mL) was stirred at room temperature overnight, after which time TLC and LCMS showed the reaction to be complete. After solvent was removed in vacuo, the crude was dissolved in $CH_3CN$ and purified by reverse phase HPLC ($C_{18}$ stationary phase, using a gradient from 10-100% $CH_3CN$/water (modified with 0.05% TFA) to give the titled compound (33 mg, 0.038 mmol, 70% yield) as white solid after lyophilization. LCMS $(M+H)^+$: 731.0. $^1H$ NMR ($CD_3OD$, 500 MHz): δ 8.18 (d, 1H), 7.99 (s, 1H), 7.97 (s, 1H), 7.91 (d, 1H), 7.89 (s, 2H), 7.63 (d, 1H), 7.51 (d, 1H), 7.38 (d, 1H), 6.88 (d, 1H), 5.79 (d, 1H), 4.73 (d, 1H), 4.20-4.31 (m, 1H), 4.03-4.17 (m, 1H), 3.99 (s, 3H), 3.83 (t, 4H), 3.60 (t, 4H), 2.38 (s, 3H), 0.66 (brd, 3H). RTA $IC_{50}$: 9 nM.

Examples 57-63

(Table 7) were prepared in an analogous fashion to Examples 55 and 56 by utilizing advanced oxazolidinone intermediates 25, 26 and 30 plus biaryl boronic acid intermediates 31 and 38.

TABLE 7

| EXAMPLE | STRUCTURE | NMR/LCMS Data | CETP Inhibition |
|---|---|---|---|
| 57 | 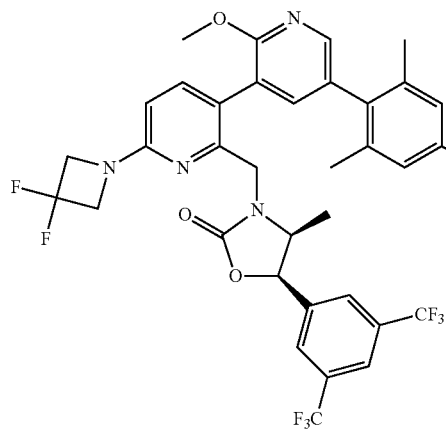 | LCMS $(M + H)^+$: 807.3 $^1H$ NMR ($CDCl_3$, 500 MHz) δ 8.03 (d, 1H), 7.91 (s, 1H), 7.77 (brd, 3H), 7.44 (d, 1H), 7.30 (d, 2H), 6.44 (d, 1H), 5.68 (d, 1H), 4.87-4.69 (m, 1H), 4.53-4.36 (m, 5H), 4.18-4.02 (m, 1H), .4.03 (s, 3H), 2.18 (brs, 3H), 2.16 (brs, 3H), 1.64 (s, 9H), 0.74 (brs, 3H). | RTA $IC_{50}$: 5 nM |

TABLE 7-continued

| EXAMPLE | STRUCTURE | NMR/LCMS Data | CETP Inhibition |
|---|---|---|---|
| 58 | 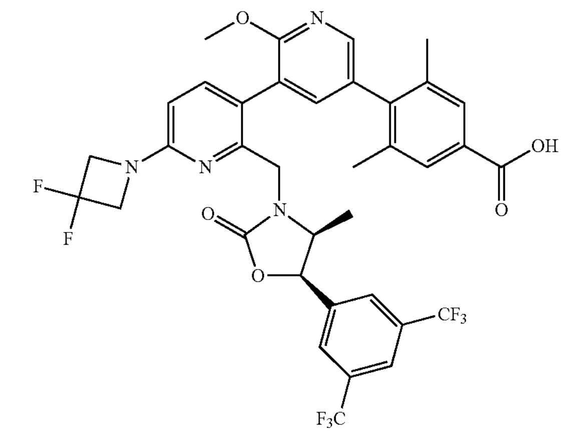 [SMILES: COc1ncc(-c2c(C)cc(C(=O)O)cc2C)cc1-c1ccc(N2CC(F)(F)C2)nc1CN1C(=O)O[C@H](c2cc(C(F)(F)F)cc(C(F)(F)F)c2)[C@@H]1C] | LCMS (M + H)+: 750.9 1H NMR (CD3OD, 500 MHz) δ 8.00 (d, 1H), 7.99 (d, 1H), 7.92 (s, 2H), 7.79 (s, 2H), 7.49 (d, 1H), 7.44 (d, 1H), 6.59 (d, 1H), 5.85 (d, 1H), 4.71 (d, 1H), 4.63-4.55 (m, 1H), 4.40 (t, 4H), 4.16-4.02 (m, 1H), .3.99 (s, 3H), 2.17 (s, 3H), 2.16 (s, 3H), 0.71 brd, 3H). | RTA IC50: 7 nM |
| 59 | 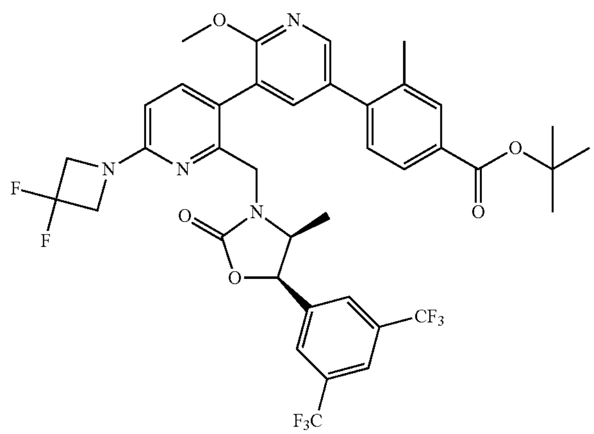 [SMILES: COc1ncc(-c2ccc(C(=O)OC(C)(C)C)cc2C)cc1-c1ccc(N2CC(F)(F)C2)nc1CN1C(=O)O[C@H](c2cc(C(F)(F)F)cc(C(F)(F)F)c2)[C@@H]1C] | LCMS (M + H)+: 793.3 1H NMR (CDCl3, 500 MHz) δ 8.21 (d, 1H), 7.94 (s, 1H), 7.90 (s, 1H), 7.88 (d, 1H), 7.75 (s, 2H), 7.48 (d, 1H), 7.46 (d, 1H), 7.32 (d, 1H), 6.45 (d, 1H), 5.65 (d, 1H), 4.71-4.93 (m, 1H), 4.37-4.54 (m, 4H), 4.15 (d, 1H), 4.06-4.18 (m, 1H), .4.02 (s, 3H), 2.39 (s, 3H), 1.64 (s, 9H), 0.75 (brs, 3H). | RTA IC50: 15 nM |
| 60 | 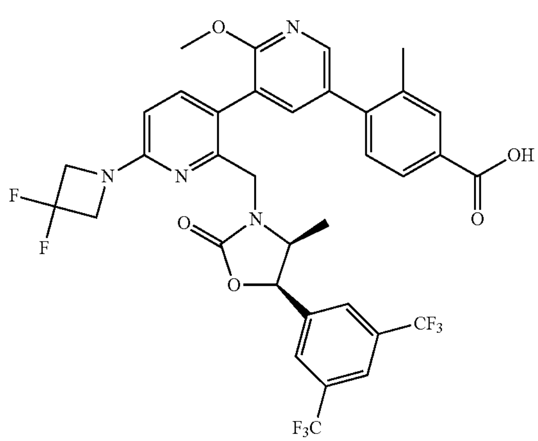 [SMILES: COc1ncc(-c2ccc(C(=O)O)cc2C)cc1-c1ccc(N2CC(F)(F)C2)nc1CN1C(=O)O[C@H](c2cc(C(F)(F)F)cc(C(F)(F)F)c2)[C@@H]1C] | LCMS (M + H)+: 736.9 1H NMR (CD3OD, 500 MHz) δ 8.18 (d, 1H), 7.99 (s, 1H), 7.96 (s, 1H), 7.91 (s, 2H), 7.89 (d, 1H), 7.63 (d, 1H), 7.50 (d, 1H), 7.38 (d, 1H), 6.59 (d, 1H), 5.81 (d, 1H), 4.72 (d, 1H), 4.61-4.56 (m, 1H), .4.41 (t, 4H), 4.17-4.03 (m, 1H), 3.98 (s, 3H), 2.38 (s, 3H), 0.70 (d, 3H). | RTA IC50: 5 nM |

TABLE 7-continued

| EXAMPLE | STRUCTURE | NMR/LCMS Data | CETP Inhibition |
|---|---|---|---|
| 61 | 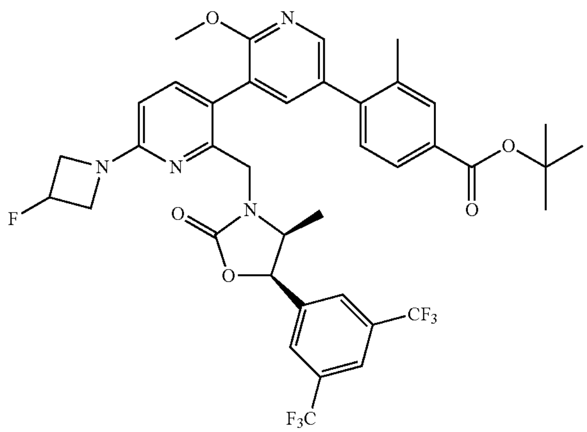 [SMILES: COc1ncc(-c2ccc(C(=O)OC(C)(C)C)cc2C)cc1-c1ccc(N2CC(F)C2)nc1CN1C(=O)O[C@H](c2cc(C(F)(F)F)cc(C(F)(F)F)c2)[C@@H]1C] | LCMS (M + H)+: 775.3 <br> 1H NMR (CDCl3, 500 MHz) δ 8.19 (d, 1H), 7.93 (s, 1H), 7.90 (s, 1H), 7.88 (d, 1H), 7.76 (s, 2H), 7.47 (d, 1H), 7.40 (d, 1H), 7.32 (d, 1H), 6.38 (d, 1H), 5.66 (d, 1H), 5.58-5.52 (m, 1/2H), 5.47-5.41 (m, 1/2H), 4.88-4.72 (m, 1H), 4.47-4.41 (m, 1H), 4.47-4.30 (m, 2H), 4.28-4.11 (m, 2H), 4.15-4.03 (m, 1H), .4.03 (s, 3H), 2.39 (s, 3H), 1.64 (s, 9H), 0.74 (brs, 3H). | RTA IC$_{50}$: 15 nM |
| 62 | 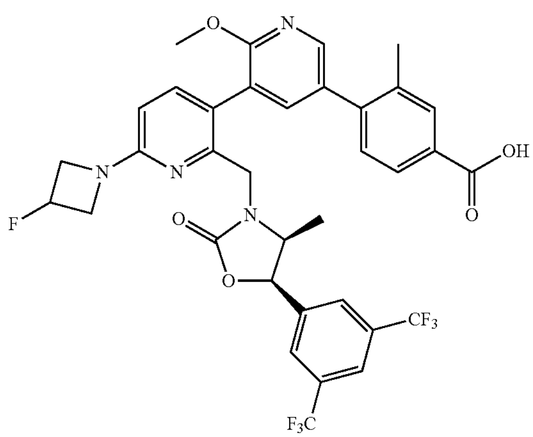 [SMILES: COc1ncc(-c2ccc(C(=O)O)cc2C)cc1-c1ccc(N2CC(F)C2)nc1CN1C(=O)O[C@H](c2cc(C(F)(F)F)cc(C(F)(F)F)c2)[C@@H]1C] | LCMS (M + H)+: 719.2 <br> 1H NMR (CD3OD, 500 MHz) δ 8.21 (d, 1H), 7.99 (s, 1H), 7.97 (s, 1H), 7.91 (d, 1H), 7.88 (s, 2H), 7.68 (s, 1H), 7.63 (s, 1H), 7.38 (d, 1H), 6.67 (d, 1H), 5.71 (d, 1H), 5.61-5.55 (m, 1/2H), 5.50-5.43 (m, 1/2H), 4.75 (d, 1H), 4.57-4.46 (m, 2H), 4.33-4.27 (m, 1H), 4.28-4.22 (m, 1H), 4.23-4.15 (m, 2H) .4.01 (s, 3H), 2.37 (s, 3H), 0.64 (brd, 3H). | RTA IC$_{50}$: 6 nM |
| 63 | 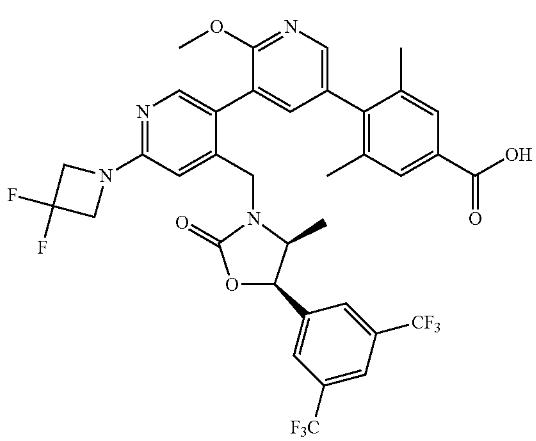 [SMILES: COc1ncc(-c2c(C)cc(C(=O)O)cc2C)cc1-c1cnc(N2CC(F)(F)C2)cc1CN1C(=O)O[C@H](c2cc(C(F)(F)F)cc(C(F)(F)F)c2)[C@@H]1C] | 1H NMR (500 MHz, CD3OD): δ 8.07 (d, J = 2.2 Hz, 1 H); 8.02 (s, 1 H); 7.97 (s, 1 H); 7.93 (s, 2 H); 7.80 (s, 2 H); 7.54 (s, 1 H); 6.84 (s, 1 H); 5.82 (bs, 1 H); 4.77 (d, J = 16.4 Hz, 1 H); 4.70-4.60 (m, 4 H); 4.21-4.12 (m, 2 H); 4.02 (s, 3 H); 2.18 (s, 6 H); 0.66 (d, J = 6.0 Hz, 3 H). | RTA IC$_{50}$: 52 nM |

Example 64

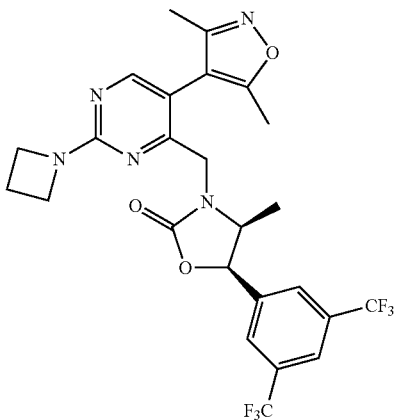 [SMILES: Cc1noc(C)c1-c1cnc(N2CCC2)nc1CN1C(=O)O[C@H](c2cc(C(F)(F)F)cc(C(F)(F)F)c2)[C@@H]1C]

(4S,5R)-3-{[2-(azetidin-1-yl)-5-(3,5-dimethylisoxazol-4-yl)pyrimidin-4-yl]methyl}-5-[3,5-bis(trifluoromethyl)phenyl]-4-methyl-1,3-oxazolidin-2-one Step A: (4S,5R)-5-[3,5-bis(trifluoromethyl)phenyl]-3-{[5-(3,5-dimethylisoxazol-4-yl)-2-(methylthio)pyrimidin-4-yl]methyl}-4-methyl-1,3-oxazolidin-2-one To a solution of (4S,5R)-5-[3,5-bis(trifluoromethyl)phenyl]-3-{[5-bromo-2-(methylsulfanyl)pyrimidin-4-yl]methyl}-4-methyl-1,3-oxazolidin-2-one (INTERMEDIATE 8, 500 mg, 0.943 mmole) and 3,5-dimethylisoxazole-4-boronic acid, pinacol ester (231 mg, 1.037 mmol) were treated in a similar fashion to INTERMEDIATE 17 Step A or EXAMPLE 64 Step A to give the title compound after filtration of the reaction mixture, evaporation and silica gel purification of the crude isolate. LCMS (M+H)$^+$: 547.2.

Step B: (4S,5R)-5-[3,5-bis(trifluoromethyl)phenyl]-3-{[5-(3,5-dimethylisoxazol-4-yl)-2-(methylsulfonyl)pyrimidin-4-yl]methyl}-4-methyl-1,3-oxazolidin-2-one To a solution of (4S,5R)-5-[3,5-bis(trifluoromethyl)phenyl]-3-{[5-(3,5-dimethylisoxazol-4-yl)-2-(methylthio)pyrimidin-4-yl]methyl}-4-methyl-1,3-oxazolidin-2-one (130 mg, 0.238 mmol) in dichloromethane (5 mL) was added 3-chloroperoxybenzoic acid (123 mg, 0.714 mmole). The mixture was stirred for 3 hours, then diluted with dichloromethane. It was then washed with saturated aqueous $Na_2S_2O_3$, saturated aqueous $NaHCO_3$, and brine. The organic layer was dried over $Na_2SO_4$, filtered and concentrated and used directly for next step without purification. LCMS (M+H)$^+$: 579.1.

Step C: (4S,5R)-3-{[2-(azetidin-1-yl)-5-(3,5-dimethylisoxazol-4-yl)pyrimidin-4-yl]methyl}-5-[3,5-bis(trifluoromethyl)phenyl]-4-methyl-1,3-oxazolidin-2-one (4S,5R)-5-[3,5-bis(trifluoromethyl)phenyl]-3-{[5-(3,5-dimethylisoxazol-4-yl)-2-(methylsulfonyl)pyrimidin-4-yl]methyl}-4-methyl-1,3-oxazolidin-2-one was dissolved in an excess amount of cyclobutylamine in THF, then heated to 150° C. for 2 hours in a microwave reactor. The reaction mixture was evaporated, then reconstituted in methanol and purified by preparative reverse phase HPLC to give the title compound. LCMS (M+H)$^+$: 556.1. $^1$H NMR (CDCl$_3$, 500 MHz): δ 8.15 (s, 1H), 7.91 (s, 1H), 7.74 (s, 2H), 5.77 (d, 1H), 4.50-4.30 (m, 6H), 3.92 (t, 1H), 2.53 (m, 2H), 2.32 (d, 3H), 2.16 (d, 3H), 0.77 (d, 3H). RTA IC$_{50}$: 271 nM.

What is claimed is:
1. A compound of Formula I, or a pharmaceutically acceptable salt thereof:

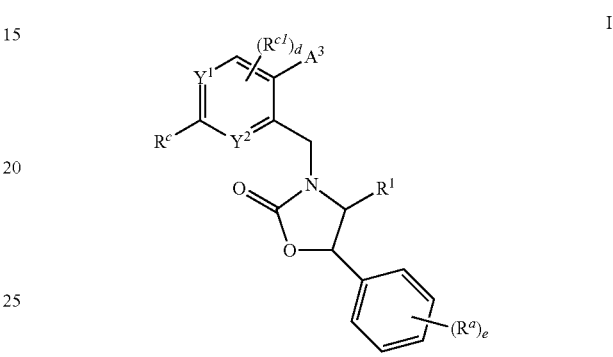

I wherein A$^3$ is represented by Formula II;
wherein Y$^1$ and Y$^2$ are each N;

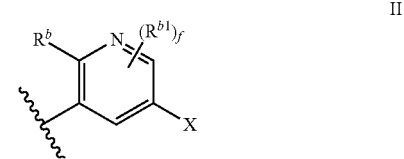

II

R$^1$ is H, CF$_3$, or C$_{1-3}$ alkyl;

Each R$^a$ is independently C$_{1-3}$ alkyl optionally substituted with 1-6 halogens; —OC$_{1-3}$ alkyl optionally substituted with 1-6 halogens; halogen; —CN; or C$_{3-4}$cycloalkyl optionally substituted with 1-3 halogens;

R$^c$ is (a) a 4-7 membered monocyclic heterocycle having one N which is bonded to the heteroaromatic ring to which R$^c$ is connected, wherein the monocyclic heterocycle optionally has 1-3 double bonds, one carbonyl, and 1-3 additional heteroatom groups which are each independently N, O, S, S(O), or S(O)$_2$; or (b) a 5-8 membered bicyclic heterocycle having one N which is bonded to the heteroaromatic ring to which R$^c$ is connected, wherein the bicyclic heterocycle optionally has 1-3 double bonds, one carbonyl, and 1-3 additional heteroatom groups which are each independently N, O, S, S(O), or S(O)$_2$, wherein R$^c$ as defined in (a) or (b) is optionally substituted with 1-3 substituent groups which are independently halogen, —OH, —CN, C$_{1-3}$ alkyl, or —OC$_{1-3}$ alkyl, wherein C$_{1-3}$ alkyl and —OC$_{1-3}$ alkyl are optionally substituted with 1-6 halogens;

Each R$^{c1}$ is independently C$_{1-3}$ alkyl, —OC$_{1-3}$ alkyl, or halogen, wherein alkyl in either case is optionally substituted with 1-6 halogens;

R$^b$ is H, C$_{1-4}$ alkyl, —OC$_{1-4}$ alkyl, —OC$_{3-6}$ cycloalkyl, halogen, —CN, —NO$_2$, or —OH, wherein C$_{1-4}$ alkyl and —$OC_{1-4}$ alkyl are optionally substituted with 1-6 halogens, and —$OC_{3-6}$ cycloalkyl is optionally substituted with 1-3 halogens;

Each $R^{b1}$ is independently $C_{1-3}$ alkyl, —$OC_{1-3}$ alkyl, or halogen, wherein $C_{1-3}$ alkyl and —$OC_{1-3}$ alkyl are optionally substituted with 1-6 halogens;

X is:
(a) (i) halogen, (ii) —$C_{1-4}$ alkyl, (iii) —$C_{3-6}$cycloalkyl-Y, or $C_{1-3}$alkyl-Y, wherein Y is —CN, —OH, or —$OCH_3$, (iv) —$C_{3-6}$ cycloalkyl, or (v) -phenyl which is optionally substituted with 1-3 groups which are independently halogen, —CN, —OH, —$C_{1-4}$alkyl, —$OC_{1-4}$alkyl, or —C(=O)$C_{1-2}$alkyl, and optionally one group —$C_{1-4}$ alkyl-OH, wherein alkyl in all uses is optionally substituted with 1-6 halogens, and cycloalkyl in all uses is optionally substituted with 1-3 groups which are independently halogen or —$C_{1-3}$ alkyl which are optionally substituted with 1-6 halogens;
(b) $D^1$, wherein $D^1$ is —$CO_2H$, —$CO_2C_{1-4}$alkyl, or —C(=O)$NR^2R^3$;
(c) —$C_{1-3}$alkyl-$D^1$, wherein —$C_{1-3}$alkyl is optionally substituted with 1-6 halogens;
(d) —$C_{3-6}$cycloalkyl-$D^1$, wherein cycloalkyl is optionally substituted with 1-2 groups which are independently —$C_{1-3}$ alkyl or halogen, wherein —$C_{1-3}$ alkyl is optionally substituted with 1-6 halogens;
(e) —$C_{3-6}$cycloalkyl-$CH_2$-$D^1$, wherein cycloalkyl is optionally substituted with 1-2 groups which are independently —$C_{1-3}$alkyl or halogen, wherein —$C_{1-3}$ alkyl is optionally substituted with 1-6 halogens;
(f) -phenyl-$D^2$, wherein $D^2$ is $D^1$, HET, or —C(=O)NH—HET, wherein phenyl is optionally substituted with 1-3 substituents which are independently halogen, —CN, —OH, —$C_{1-3}$ alkyl optionally substituted with 1-6 halogens, or —$OC_{1-3}$alkyl optionally substituted with 1-6 halogens;
(g) -HET-$D^1$, wherein HET is a 5-6-membered heteroaromatic ring having 1-4 heteroatom groups which are each independently N, O, S, S(O), S(O)$_2$, or C(=O), wherein HET is optionally substituted with 1-3 groups which are independently halogen, —$CH_3$, —$CF_3$, —$OCH_3$, or —$OCF_3$; or
(h) —($C_{1-2}$ alkyl)$_{0-2}$-HET, wherein HET is optionally substituted with 1-3 groups which are independently halogen, —OH, —$NH_2$, —$C_{1-4}$alkyl optionally substituted with 1-6 halogens, or —$OC_{1-3}$alkyl optionally substituted with 1-6 halogens, and optionally one group which is —$C_{1-3}$alkyl-CN or —$CH_2C$(=O) $NR^2R^3$;

$R^2$ and $R^3$ are each independently H or —$C_{1-3}$alkyl, or $R^2$ and $R^3$ are optionally joined to form a bridging group having 3-5 carbons, thereby yielding a 4-6 membered cyclic amide group;

d is an integer from 0-2;
e is an integer from 0-3; and
f is an integer from 0-2.

2. The compound of claim 1, wherein
$R^1$ is H or $C_{1-3}$ alkyl;
Each $R^a$ is independently $CF_3$, —$OCF_3$, $CH_3$, —$OCH_3$, halogen, —CN, or cyclopropyl which is optionally substituted with 1-3 halogens;
$R^c$ is (a) a 4-6 membered monocyclic amine having one N which is bonded to the heteroaromatic ring to which $R^c$ is connected, wherein the monocyclic amine optionally has one O in the ring and optionally 1-2 double bonds, wherein $R^c$ is optionally substituted with 1-2 groups which are each independently halogen, —OH, $CH_3$, —$OCH_3$, $CF_3$, or —$OCF_3$;

Each $R^{c1}$ is independently $CH_3$, $CF_3$, —$OCH_3$, —$OCF_3$ or halogen;

$R^b$ is H, $C_{1-4}$ alkyl, —$OC_{1-4}$ alkyl, —$OC_{3-6}$ cycloalkyl, or halogen, wherein $C_{1-4}$ alkyl and —$OC_{1-4}$ alkyl are optionally substituted with 1-6 halogens, and —$OC_{3-6}$ cycloalkyl is optionally substituted with 1-3 halogens;

Each $R^{b1}$ is independently halogen, $CF_3$, or $CH_3$;
d is 0 or 1;
e is an integer from 1-3; and
f is 0 or 1,
or a pharmaceutically acceptable salt thereof.

3. The compound of claim 2, wherein
$R^1$ is $CH_3$;
Each $R^a$ is independently F, —$CF_3$, or —$OCF_3$;
$R^c$ is (1) a 4-5 membered saturated monocyclic amine having one N which is bonded to the heteroaromatic ring to which $R^c$ is connected and which is optionally substituted with 1-2 groups which are independently F, $CH_3$, or —OH, (2) morpholino in which the N of the morpholino group is connected to the heteroaromatic ring to which $R^c$ is connected, or (3) imidazolyl in which the N of the imidazolyl group is connected to the heteroaromatic ring to which $R^c$ is connected;

Each $R^{c1}$ is independently —$CH_3$ or Br;
$R^b$ is $C_{1-4}$ alkyl or —$OC_{1-4}$ alkyl, wherein $C_{1-4}$ alkyl and —$OC_{1-4}$ alkyl are optionally substituted with 1-6 halogens; and
$R^{b1}$ is F,
or a pharmaceutically acceptable salt thereof.

4. The compound of claim 3 wherein
$R^b$ is —$C_{1-4}$ alkyl or —$OC_{1-2}$ alkyl, wherein —$C_{1-4}$ alkyl and —$OC_{1-2}$ alkyl are optionally substituted with 1-6 halogens;
d is 0;
e is an integer from 1-3; and
f is 0,
or a pharmaceutically acceptable salt thereof.

5. The compound of claim 4, wherein
e is an integer from 1-2,
or a pharmaceutically acceptable salt thereof.

6. The compound of claim 1, wherein
X is:
(a) (i) halogen; (ii) —$C_{1-4}$alkyl which is optionally substituted with 1-6 halogens; (iii) $C_{1-3}$ alkyl-Y, wherein $C_{1-3}$ alkyl is optionally substituted with 1-6 halogens and Y is —CN, —OH, or —$OCH_3$; or (iv) —$C_{3-6}$cycloalkyl optionally substituted with 1-3 groups independently selected from halogen and —$CH_3$;
(b) $D^1$, wherein $D^1$ is —$CO_2H$, —$CO_2C_{1-4}$alkyl, or —C(=O)$NR^2R^3$;
(c) —$C_{1-3}$ alkyl-$D^1$, wherein alkyl is optionally substituted with 1-6 halogens;
(d) —$C_{3-6}$cycloalkyl-$D^1$, wherein cycloalkyl is optionally substituted with 1-2 groups which are independently —$CH_3$, $CF_3$, or halogen;
(e) —$C_{3-6}$cycloalkyl-$CH_2$-$D^1$, wherein cycloalkyl is optionally substituted with 1-2 groups which are independently —$CH_3$, $CF_3$, or halogen;
(f) -phenyl-$D^2$, wherein $D^2$ is $D^1$, 1,3,4-oxadiazol-2(3H)-one, tetrazole, or —C(=O)NH-tetrazole, wherein phenyl is optionally substituted with 1-3 substituents which are independently halogen, —$CH_3$, —$CF_3$, —$OCH_3$, or —$OCF_3$; or
(g) HET, wherein HET is a 5-membered heteroaromatic ring having 1-3 heteroatoms groups which are each independently N, O, or S and is optionally substituted with 1-3 groups which are independently halogen, —C$_{1-3}$alkyl optionally substituted with 1-6 halogens, or —OC$_{1-3}$ alkyl optionally substituted with 1-6 halogens, and is optionally substituted with one group which is —C$_{1-3}$ alkyl-CN or —CH$_2$C(=O) NR$^2$R$^3$;

and R$^2$ and R$^3$ are independently H or —CH$_3$, or a pharmaceutically acceptable salt thereof.

7. The compound of claim 1, wherein

X is:

(a) (i) Cl; (ii) —C$_{1-4}$ alkyl which is optionally substituted with 1-6 halogens; (iii) C$_{1-3}$ alkyl-Y, wherein C$_{1-3}$ alkyl is optionally substituted with 1-6 halogens and Y is —OH;

or (iv) —C$_{3-6}$cycloalkyl;

(b) —C$_{1-3}$ alkyl-D$^1$, wherein D$^1$ is —CO$_2$H, —CO$_2$C$_{1-4}$alkyl, or —C(=O)NR$^2$R$^3$;

(c) -phenyl-D$^2$, wherein D$^2$ is D$^1$, 1,3,4-oxadiazol-2(3H)-one, tetrazole, or —C(=O)NH-tetrazole, wherein phenyl is optionally substituted with 1-3 substituents which are independently halogen, —CH$_3$, or —CF$_3$; or (g) HET, wherein HET is a 5-membered heteroaromatic ring having 1-3 heteroatoms which are each independently N, O, or S and is optionally substituted with 1-3 groups which are each independently halogen, —C$_{1-3}$ alkyl optionally substituted with 1-6 halogens, or —OC$_{1-3}$ alkyl optionally substituted with 1-6 halogens, and is optionally substituted with one group which is —C$_{1-3}$ alkyl-CN or —CH$_2$C(=O) NR$^2$R$^3$;

wherein R$^2$ and R$^3$ are independently H or —CH$_3$, or a pharmaceutically acceptable salt thereof.

8. The compound of claim 7, wherein HET is oxazole, isoxazole, thiazole, isothiazole, pyrazole, imidazole, thiophene, furan, pyrrole, triazole, tetrazole, or thiadiazole, or a pharmaceutically acceptable salt thereof.

9. The compound of claim 8, wherein HET is isoxazole, thiazole, or pyrazole, or a pharmaceutically acceptable salt thereof.

10. The compound of claim 1, or a pharmaceutically acceptable salt thereof, having the structure below:

117
-continued
5
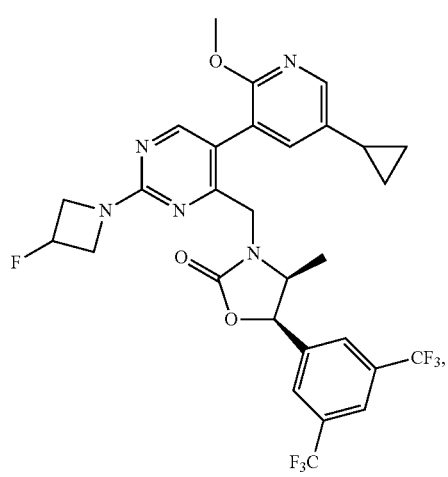
6
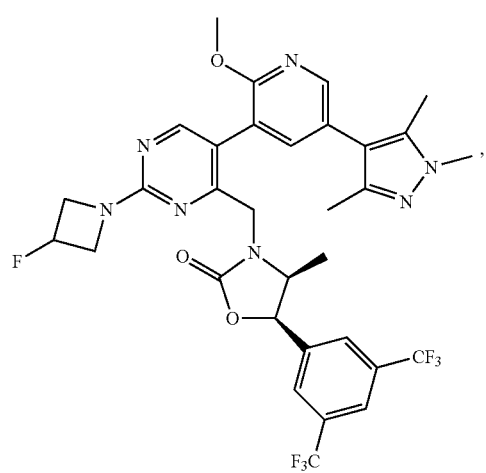
7
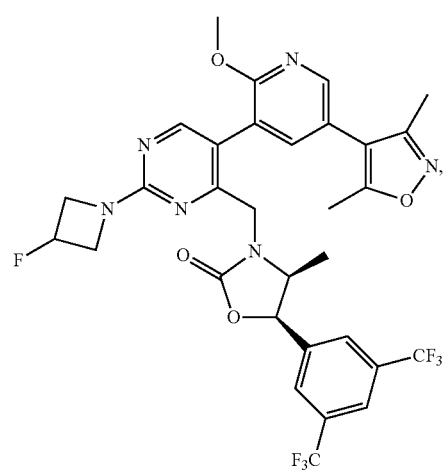
118
-continued
8
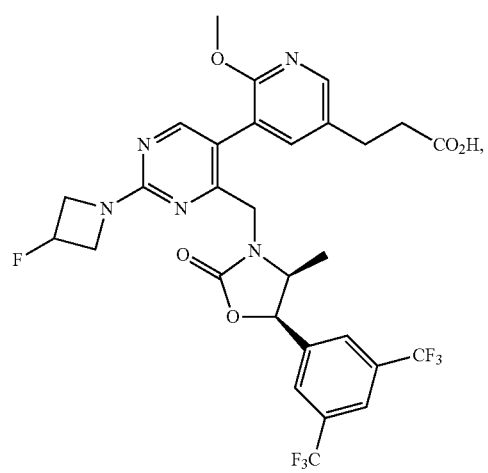
9
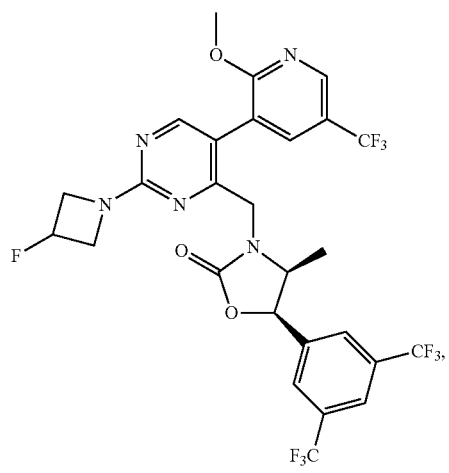
10
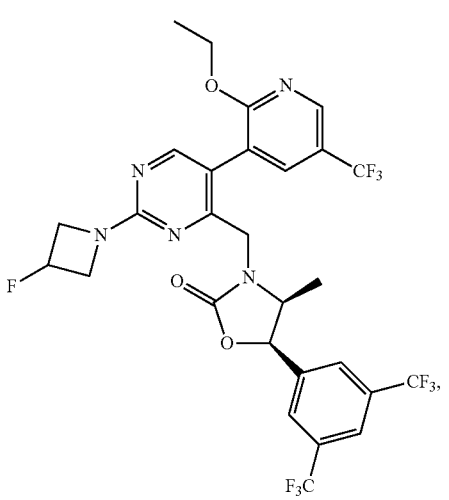

-continued
11
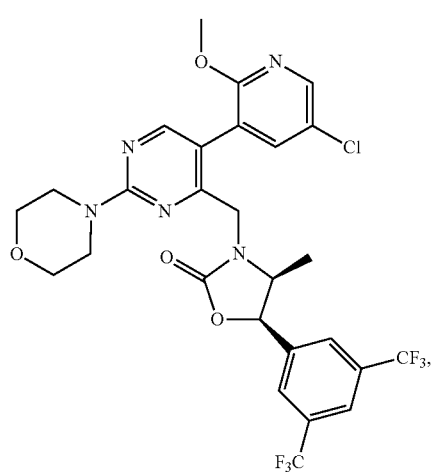
12
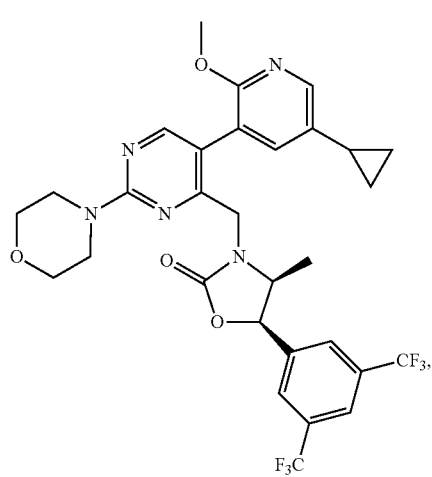
13
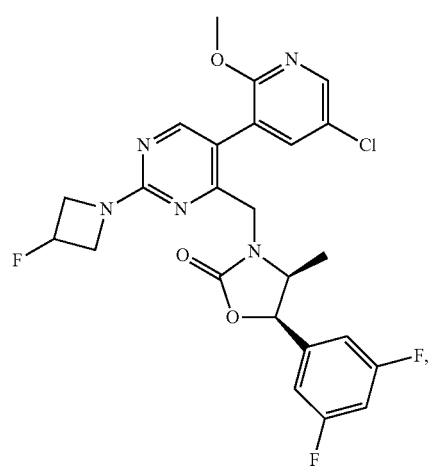
-continued
14
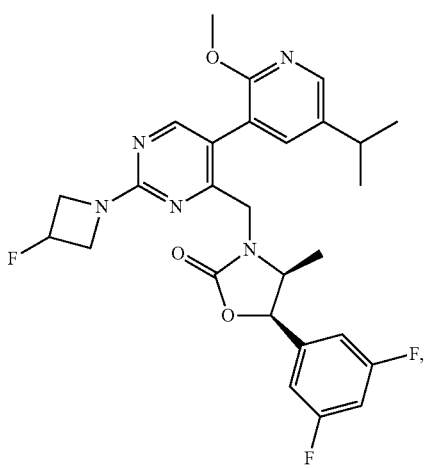
15
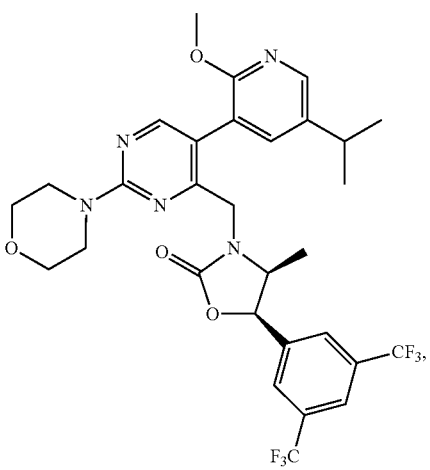
16
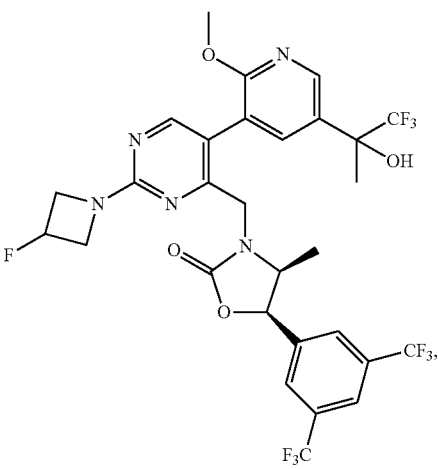

121
-continued
17
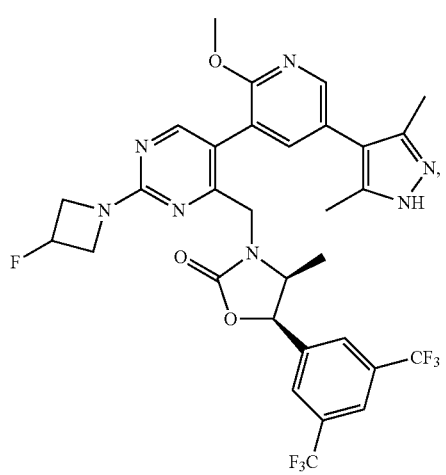
18
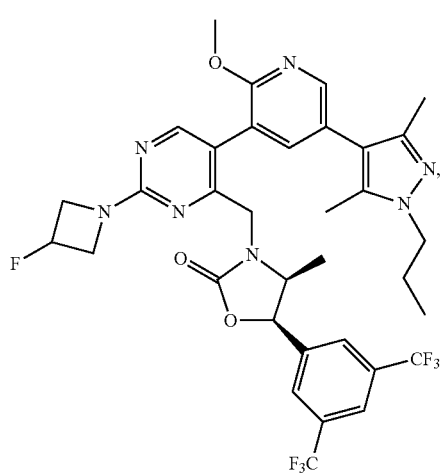
19
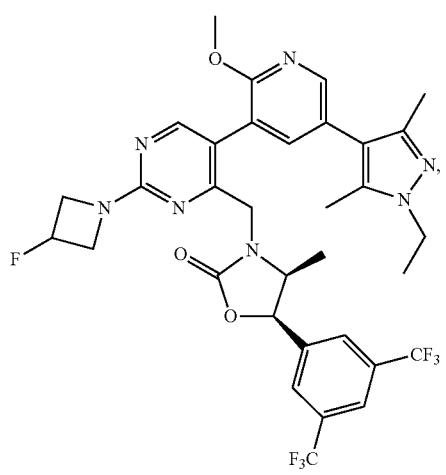
122
-continued
20
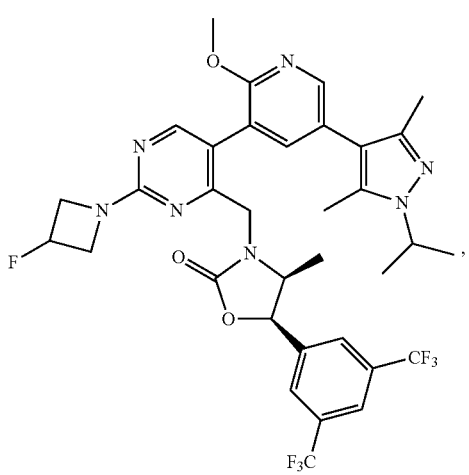
21
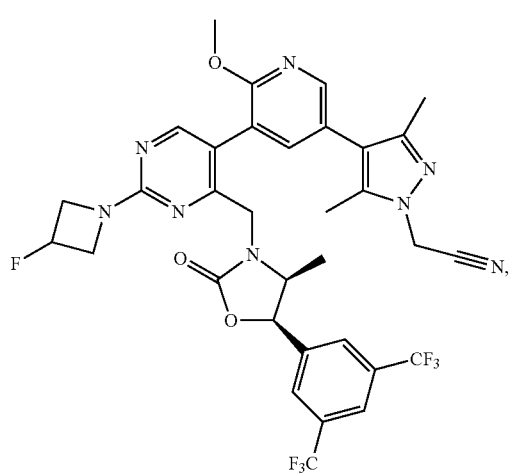
22
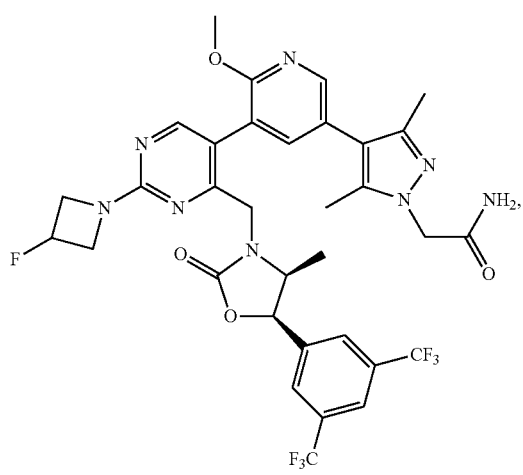

-continued
23
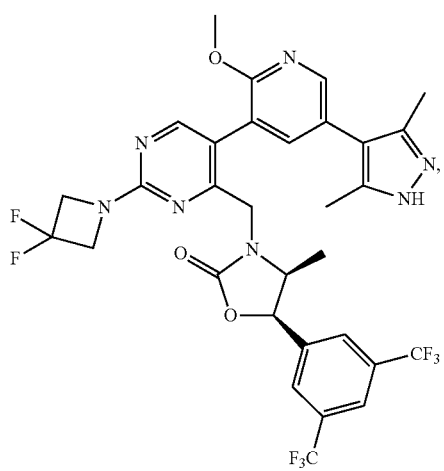
24
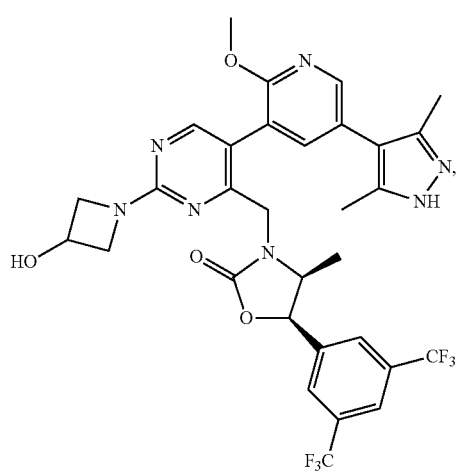
25
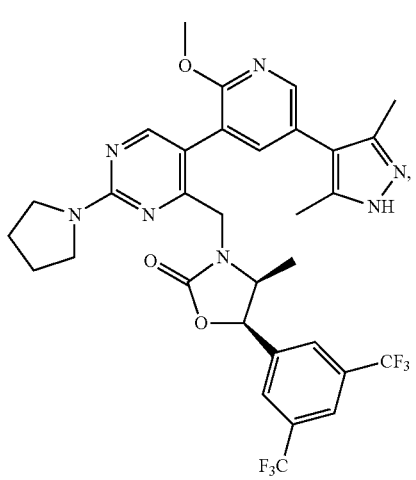
-continued
26
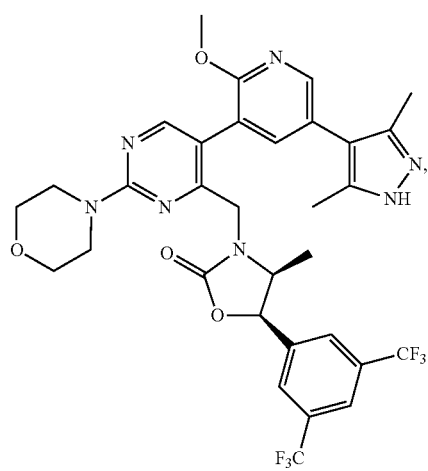
27
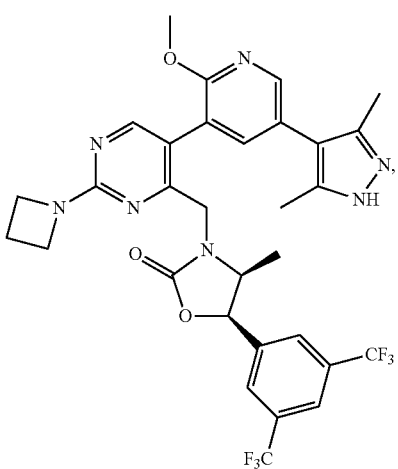
28
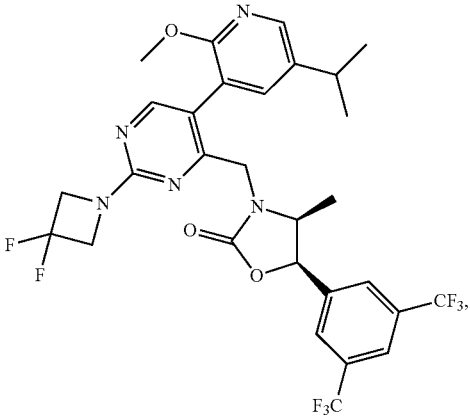

125
-continued
29
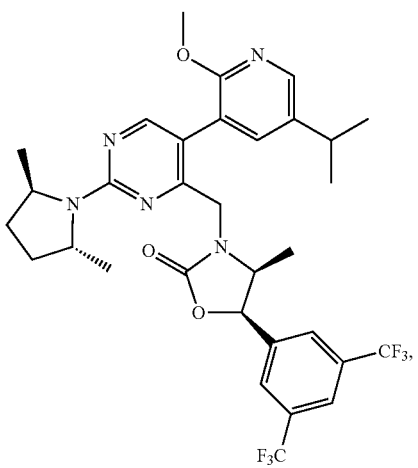
30
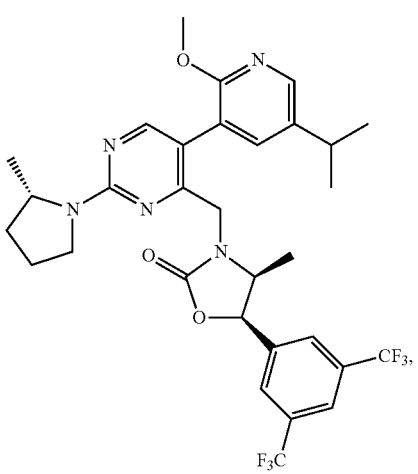
31
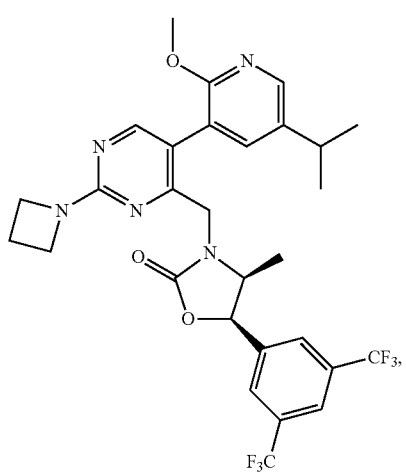
126
-continued
32
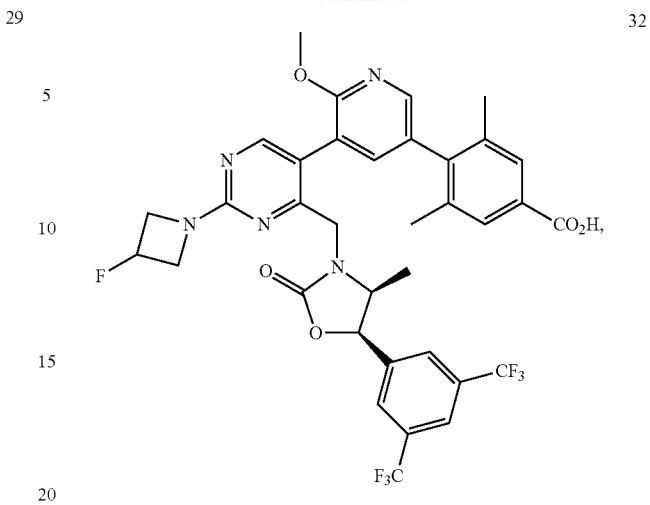
33
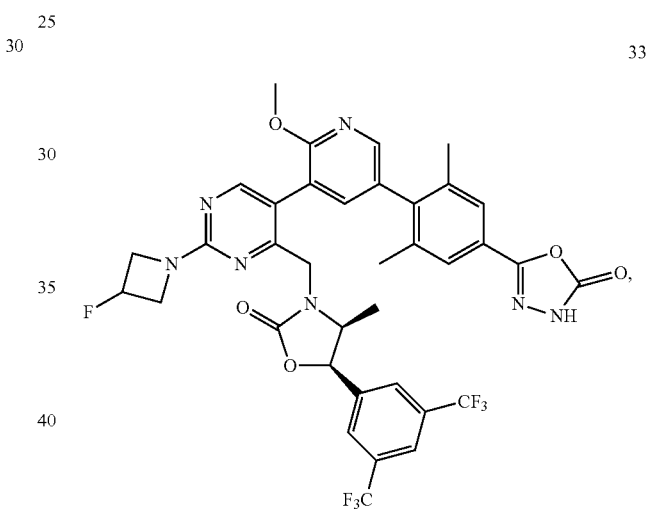
34
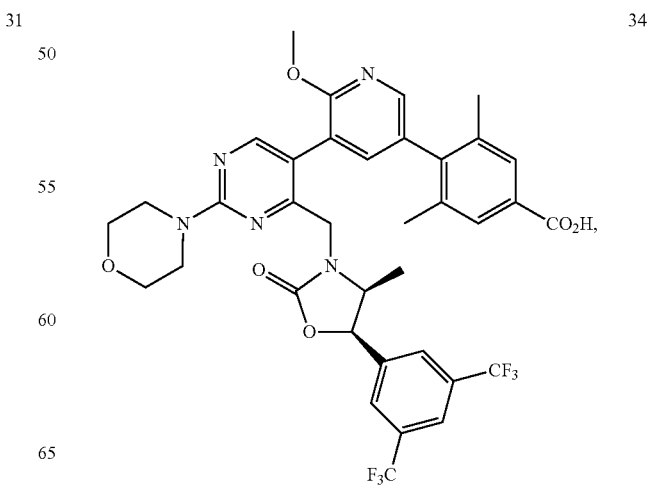

35
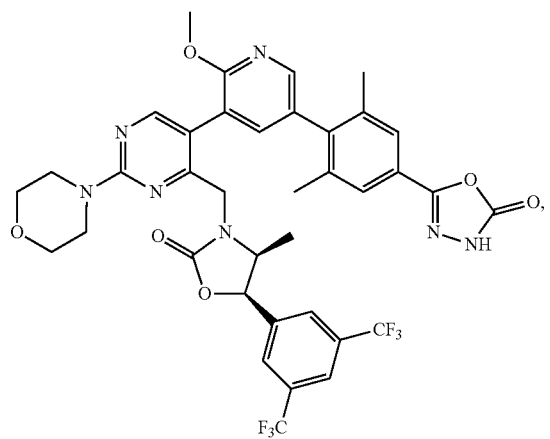
36
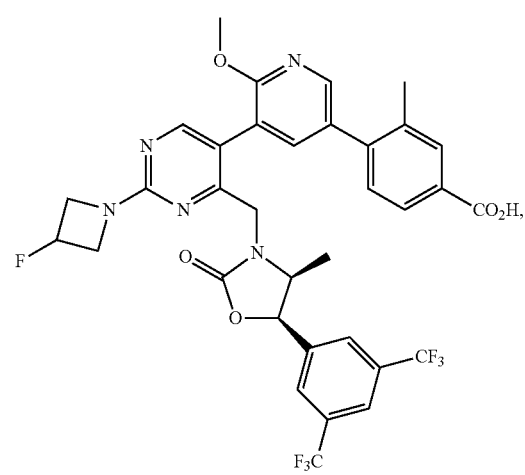
37
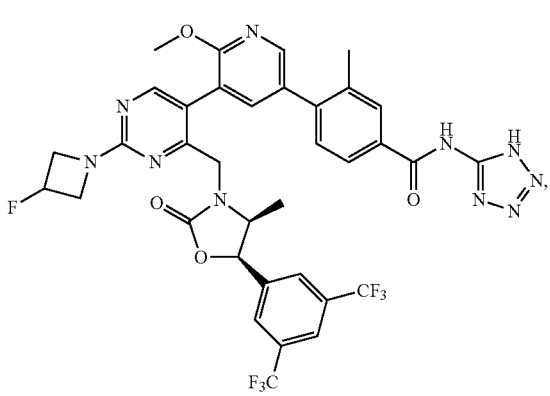
38
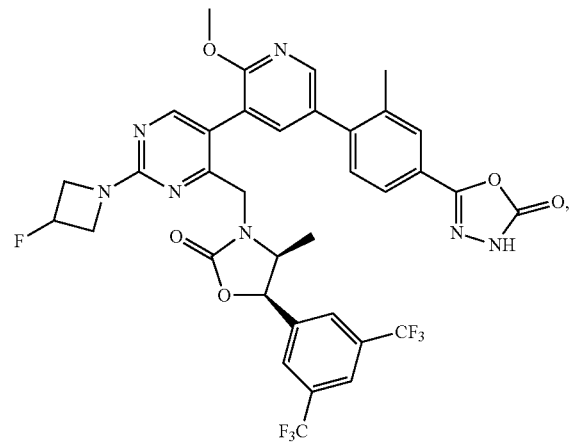
39
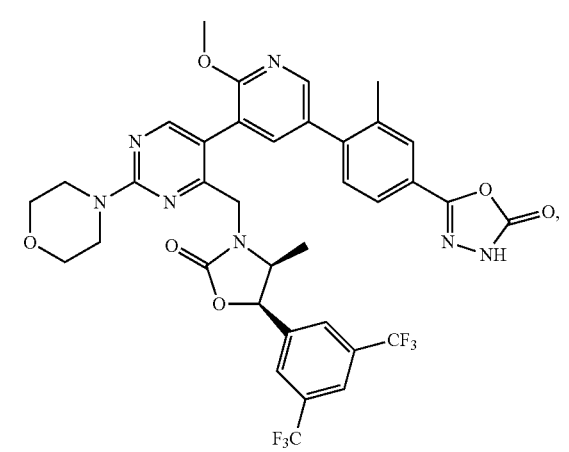
40

41
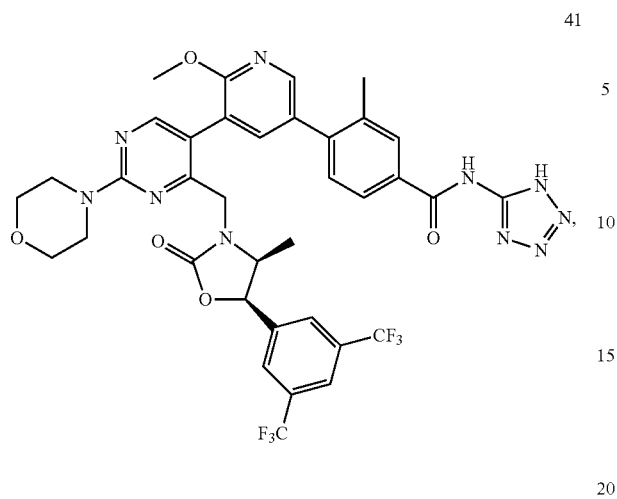
42
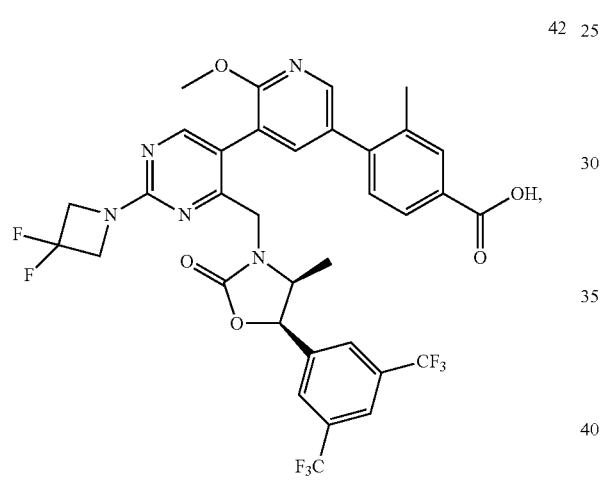
43
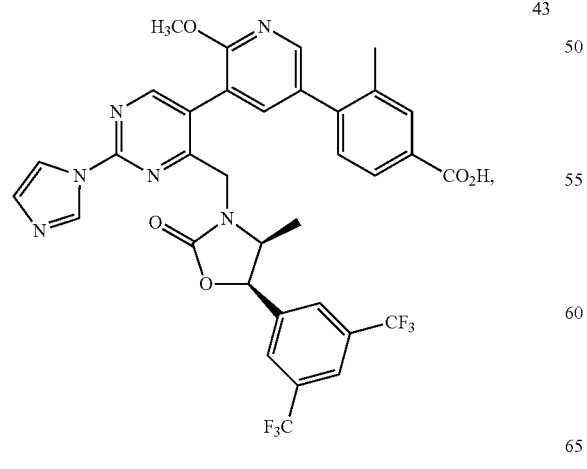
44
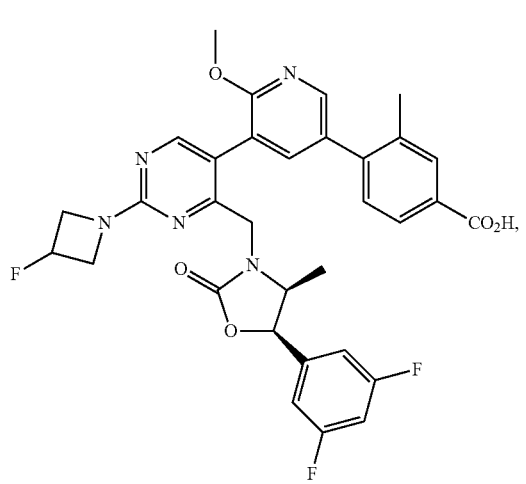
45
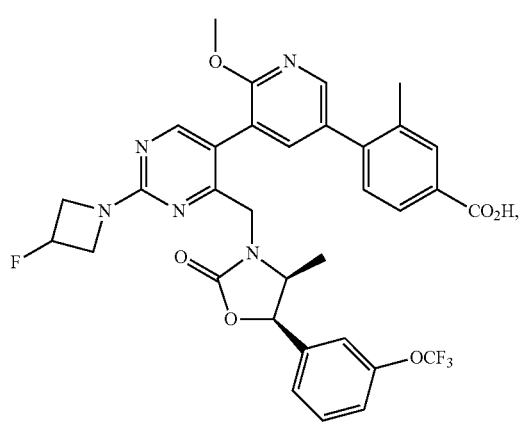
46
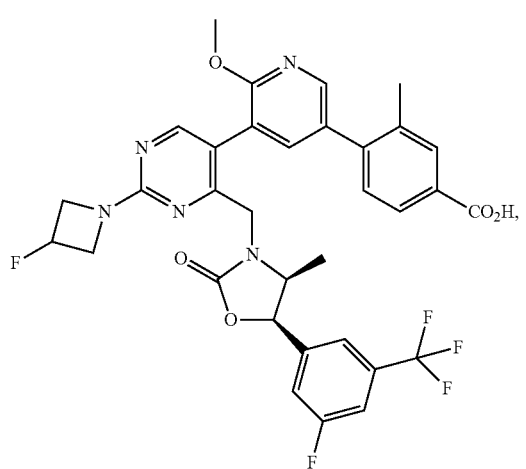

47
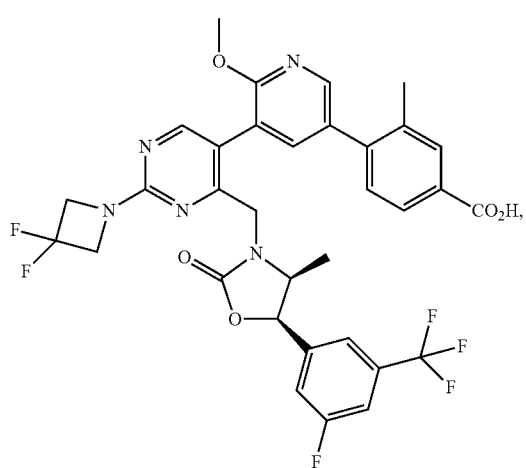
48
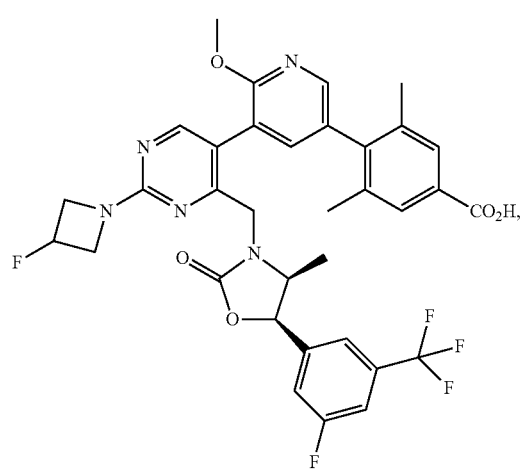
54
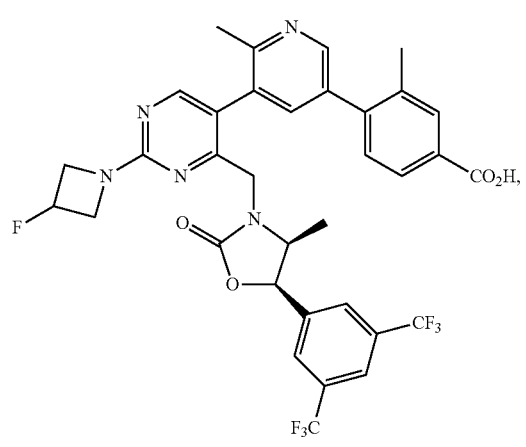
55
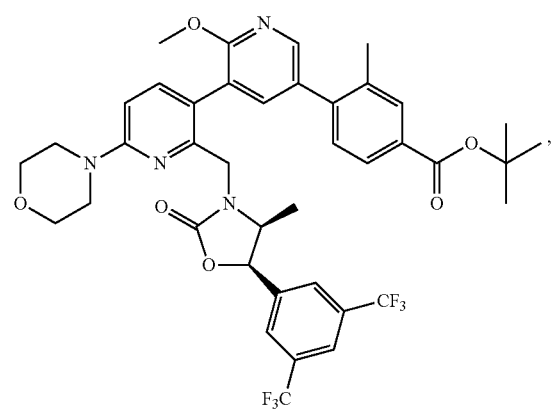
56
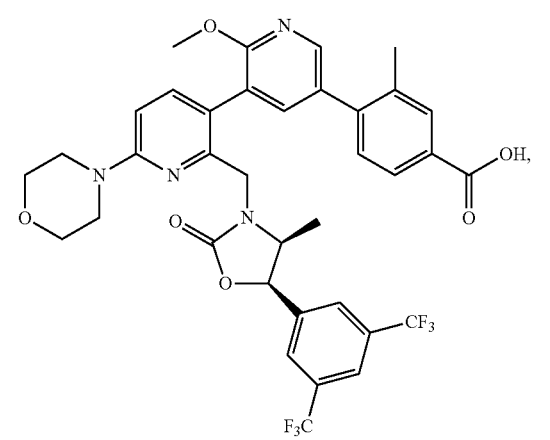
57
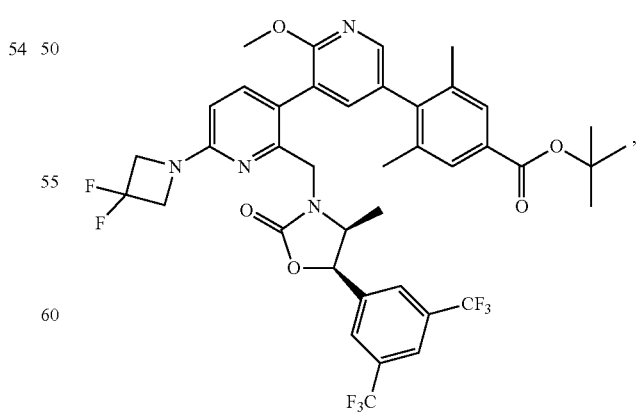

58
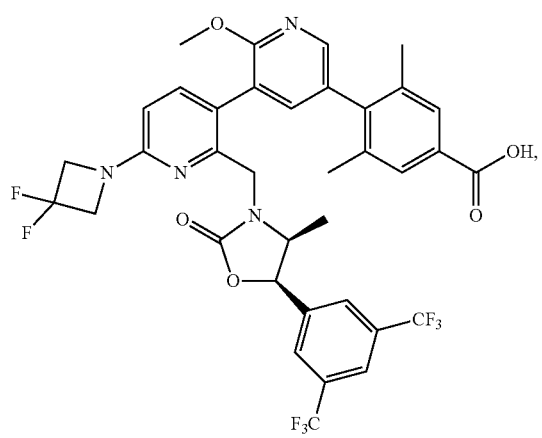
59
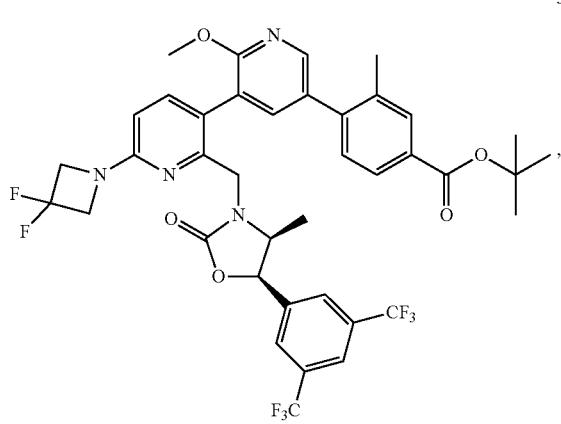
60
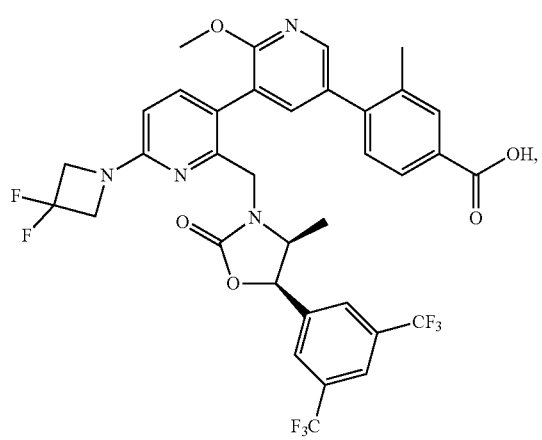
61
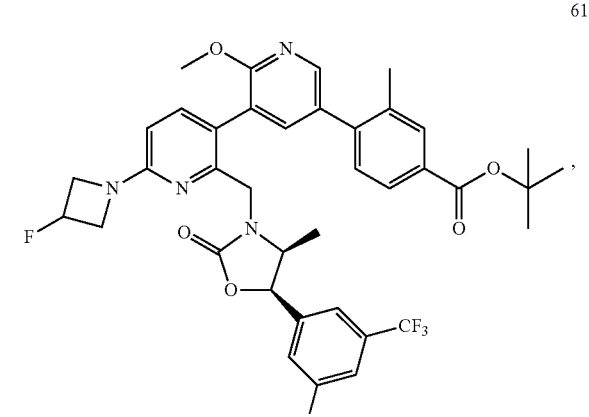
62
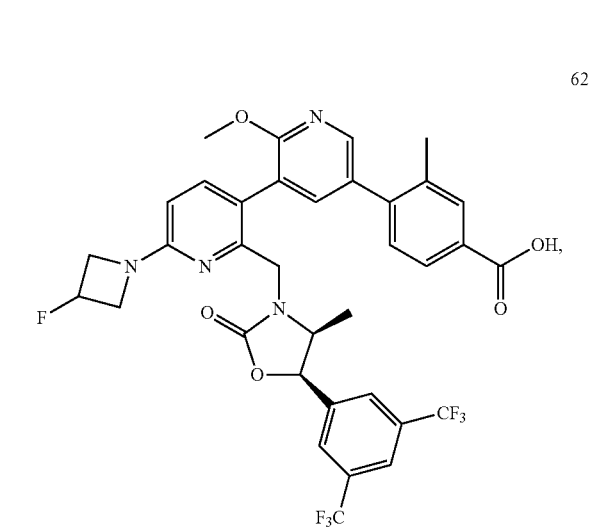
63
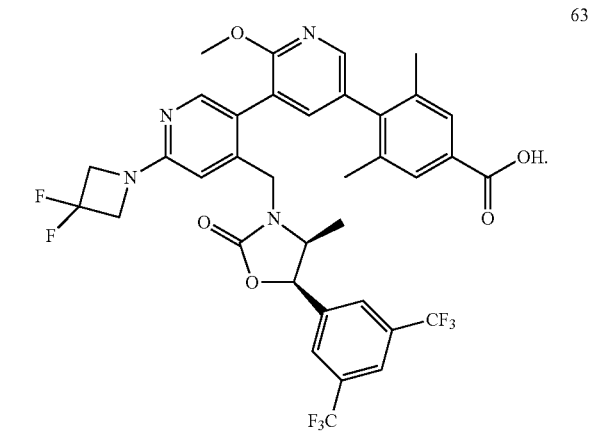
11. A pharmaceutical composition comprising the compound of claim 1 or a pharmaceutically acceptable salt thereof, and a pharmaceutically acceptable carrier.
12. The compound of claim 1 or a pharmaceutically acceptable salt thereof, wherein the compound has the structure below:

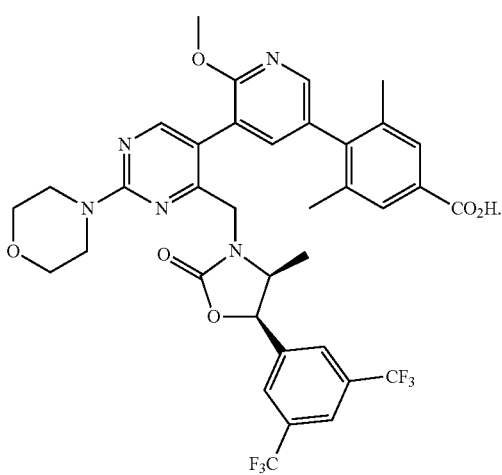 [SMILES: COc1ncc(-c2c(C)cc(C(=O)O)cc2C)cc1-c1cnc(N2CCOCC2)nc1CN1C(=O)O[C@H](c2cc(C(F)(F)F)cc(C(F)(F)F)c2)[C@@H]1C]

13. A method of treating atherosclerosis in a patient in need of treatment comprising the administration to said patient of a therapeutically effective amount of the compound of claim 1, or a pharmaceutically acceptable salt thereof.

14. A method of raising HDL-C in a patient in need of treatment comprising the administration to said patient of a therapeutically effective amount of the compound of claim 1, or a pharmaceutically acceptable salt thereof.

15. A method of lowering LDL-C in a patient in need of treatment comprising the administration to said patient of a therapeutically effective amount of the compound of claim 1, or a pharmaceutically acceptable salt thereof.

16. A method of treating dyslipidemia in a patient in need of treatment comprising the administration to said patient of a therapeutically effective amount of the compound of claim 1, or a pharmaceutically acceptable salt thereof.

17. A pharmaceutical composition comprising the compound of claim 1 or a pharmaceutically acceptable salt thereof, a pharmaceutically acceptable carrier, and one or more active ingredients selected from the group consisting of:
    (i) HMG-CoA reductase inhibitors;
    (ii) bile acid sequestrants;
    (iii) niacin and related compounds;
    (iv) PPARα agonists;
    (v) cholesterol absorption inhibitors;
    (vi) acyl CoA:cholesterol acyltransferase (ACAT) inhibitors;
    (vii) phenolic anti-oxidants;
    (viii) microsomal triglyceride transfer protein (MTP)/ApoB secretion inhibitors;
    (ix) anti-oxidant vitamins;
    (x) thyromimetics;
    (xi) LDL (low density lipoprotein) receptor inducers;
    (xii) platelet aggregation inhibitors;
    (xiii) vitamin B12 (also known as cyanocobalamin);
    (xiv) folic acid or a pharmaceutically acceptable salt or ester thereof;
    (xv) FXR and LXR ligands;
    (xvi) agents that enhance ABCA1 gene expression; and
    (xvii) ileal bile acid transporters.

\* \* \* \* \*